(12) United States Patent
Crawford et al.

(10) Patent No.: US 11,446,447 B2
(45) Date of Patent: Sep. 20, 2022

(54) SAFETY SYRINGE HAVING A MANUALLY ACTIVATED RETRACTABLE NEEDLE

(71) Applicant: Becton, Dickinson and Company, Franklin Lakes, NJ (US)

(72) Inventors: Jamieson W. Crawford, Hagersten (SE); Robert G. Ellis, Wayne, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 508 days.

(21) Appl. No.: 15/816,055

(22) Filed: Nov. 17, 2017

(65) Prior Publication Data

US 2018/0071461 A1 Mar. 15, 2018

Related U.S. Application Data

(63) Continuation of application No. 13/492,245, filed on Jun. 8, 2012, now Pat. No. 9,849,251.

(Continued)

(51) Int. Cl.
*A61M 5/32* (2006.01)
*A61B 5/15* (2006.01)
(Continued)

(52) U.S. Cl.
CPC ......... *A61M 5/322* (2013.01); *A61B 5/15003* (2013.01); *A61B 5/1535* (2013.01); *A61B 5/150236* (2013.01); *A61B 5/150244* (2013.01); *A61B 5/150251* (2013.01); *A61B 5/150259* (2013.01); *A61B 5/150396* (2013.01); *A61B 5/150404* (2013.01); *A61B 5/150519* (2013.01);

(Continued)

(58) Field of Classification Search
CPC ............... A61M 5/322; A61B 5/15003; A61B 5/150236; A61B 5/150244; A61B 5/150251; A61B 5/150259; A61B 5/150396; A61B 5/150404; A61B 5/150519; A61B 5/150641; A61B 5/150717; A61B 5/1535
USPC ........................................................ 600/576
See application file for complete search history.

(56) References Cited

U.S. PATENT DOCUMENTS

| 4,693,708 A | 9/1987 | Wanderer et al. |
| 5,059,185 A | 10/1991 | Ryan |

(Continued)

FOREIGN PATENT DOCUMENTS

EP 1911480 A1 4/2008

*Primary Examiner* — Daniel L Cerioni
(74) *Attorney, Agent, or Firm* — The Webb Law Firm

(57) ABSTRACT

A retractable needle assembly includes a housing having a sidewall defining a hollow bore, and an elongate plunger, the distal end of the plunger forming a reservoir within the hollow bore for containing a fluid therein. The plunger is adapted for slideable movement within the hollow bore. The assembly includes a hub disposed within the hollow bore and at least partially supporting a cannula therewith, and a needle retraction member engaged with the hub for manually selectable advancement with respect to a portion of the housing. The needle retraction member may be advanced from an initial position in which at least a portion of the needle is disposed outside the housing, to a retracted position in which the needle is fully surrounded by the housing. The elongate plunger may be advanced about the hub for extracting the fluid into the reservoir or expelling the fluid from the reservoir.

9 Claims, 42 Drawing Sheets

Related U.S. Application Data

(60) Provisional application No. 61/494,615, filed on Jun. 8, 2011.

(51) Int. Cl.
 *A61B 5/153* (2006.01)
 *A61M 5/315* (2006.01)
 *A61M 5/50* (2006.01)

(52) U.S. Cl.
 CPC .. *A61B 5/150641* (2013.01); *A61B 5/150717* (2013.01); *A61M 5/31511* (2013.01); *A61M 5/3291* (2013.01); *A61M 5/3293* (2013.01); *A61M 5/502* (2013.01); *A61M 2005/31508* (2013.01); *A61M 2005/3223* (2013.01); *A61M 2005/3228* (2013.01)

(56) References Cited

U.S. PATENT DOCUMENTS

| | | |
|---|---|---|
| 5,201,718 A | 4/1993 | Whisson |
| 5,338,311 A | 8/1994 | Mahurkar |
| 5,374,250 A | 12/1994 | Dixon |
| 5,501,672 A | 3/1996 | Firth et al. |
| 5,531,706 A * | 7/1996 | de la Fuente ....... A61M 5/3271 604/110 |
| 5,656,031 A | 8/1997 | Thorne et al. |
| 5,782,804 A | 7/1998 | McMahon |
| 5,810,775 A | 9/1998 | Shaw |
| 5,836,921 A | 11/1998 | Mahurkar |
| 5,931,813 A | 8/1999 | Liu |
| 5,964,735 A | 10/1999 | Alexander |
| 6,063,040 A | 5/2000 | Owen et al. |
| 6,074,370 A | 6/2000 | Pressly, Sr. et al. |
| 6,117,107 A | 9/2000 | Chen |
| 6,156,013 A | 12/2000 | Mahurkar |
| 6,162,197 A | 12/2000 | Mohammad |
| 6,302,868 B1 | 10/2001 | Mohammad |
| 6,530,903 B2 | 3/2003 | Wang et al. |
| 6,669,671 B1 | 12/2003 | Mohammad |
| 6,767,335 B1 | 7/2004 | Helg |
| 6,776,775 B1 | 8/2004 | Mohammad |
| 7,056,306 B1 | 6/2006 | Halseth et al. |
| 2002/0107488 A1 | 8/2002 | Ranford |
| 2004/0249309 A1 | 12/2004 | Yang et al. |
| 2008/0097242 A1 | 4/2008 | Cai |

\* cited by examiner

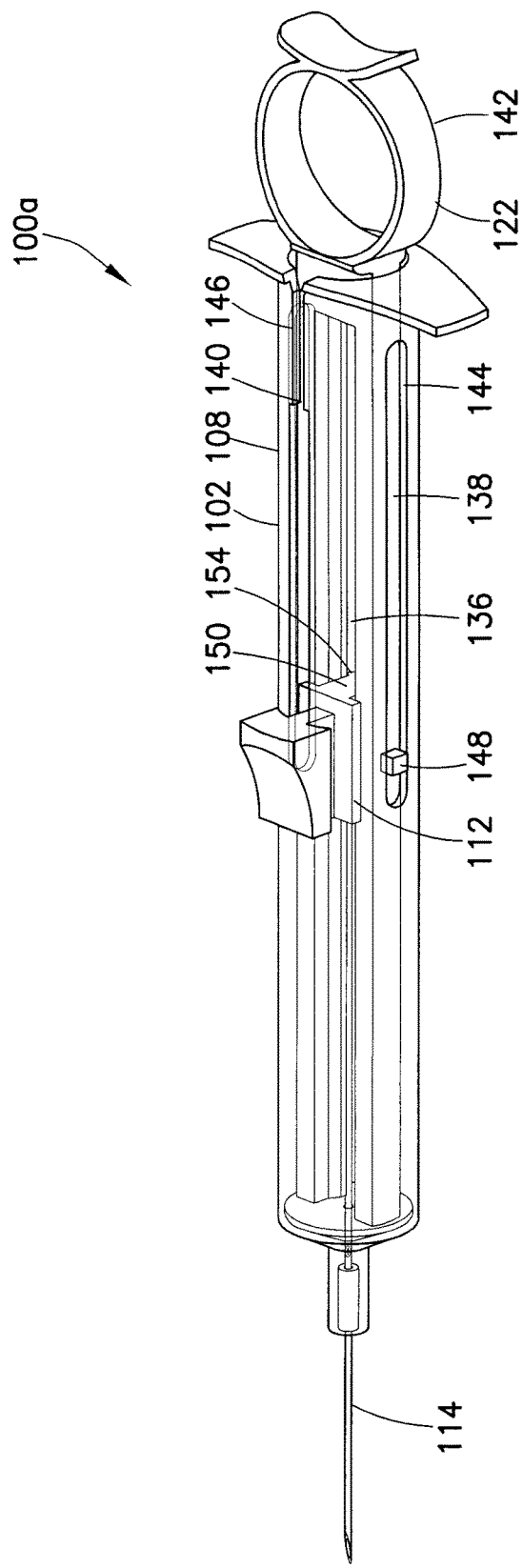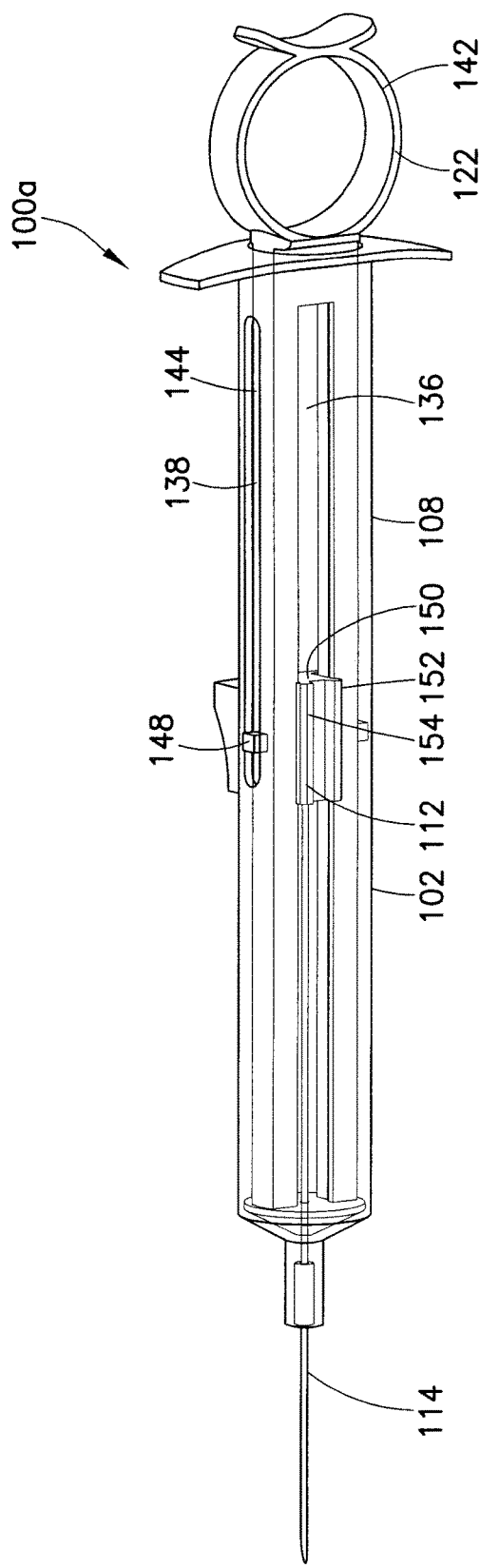
FIG.4
FIG.5

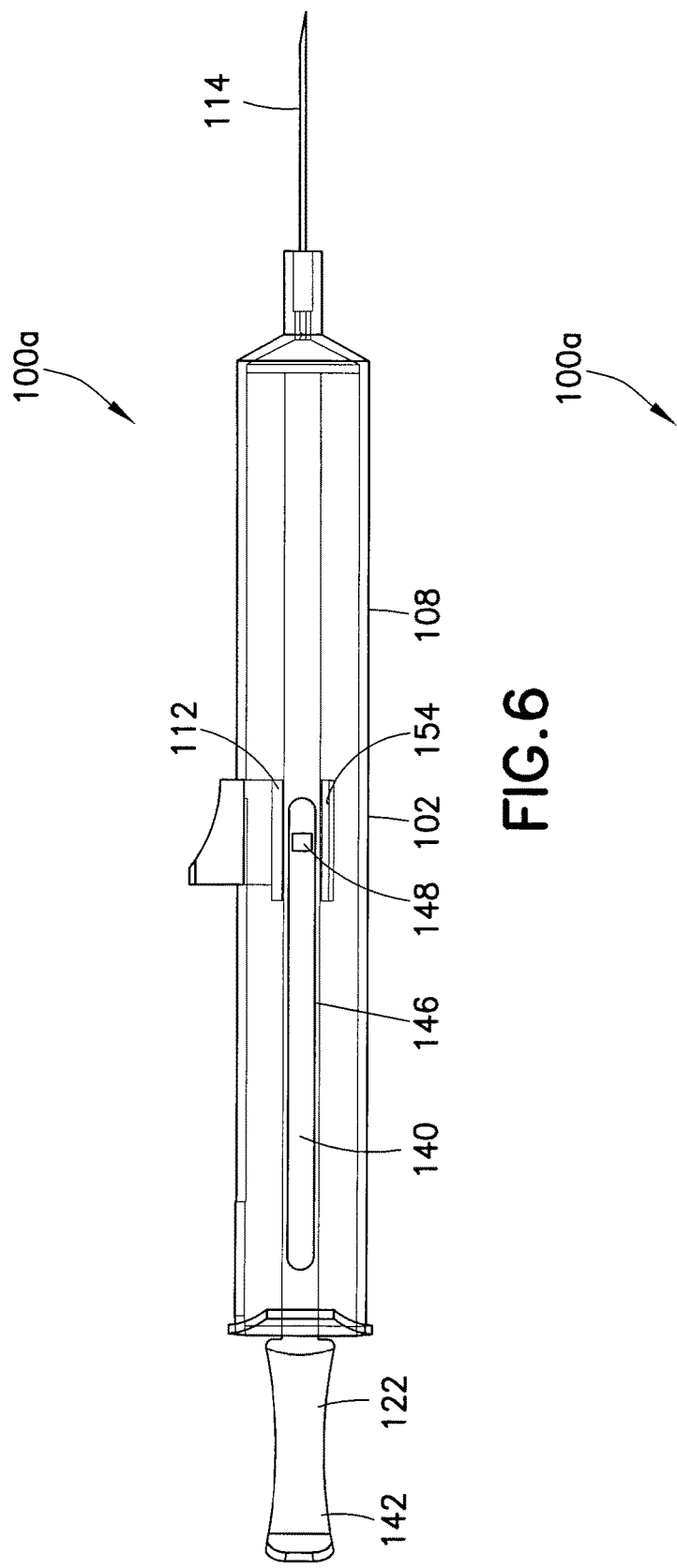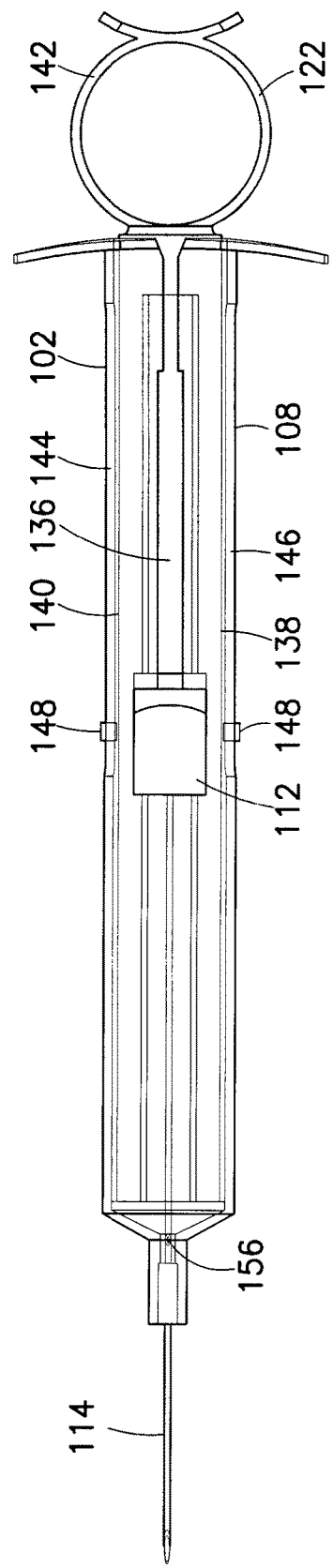

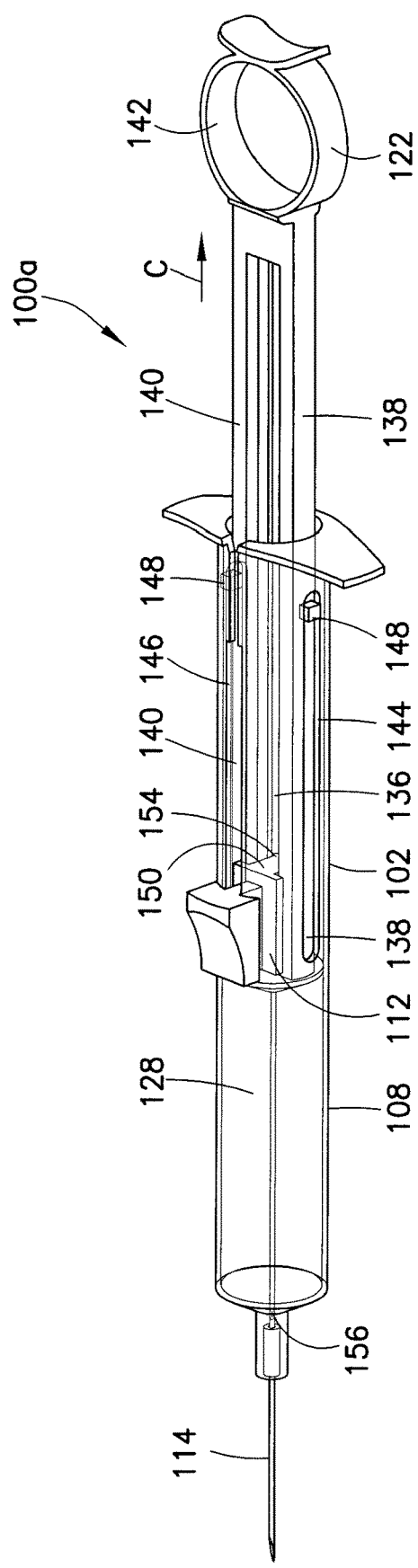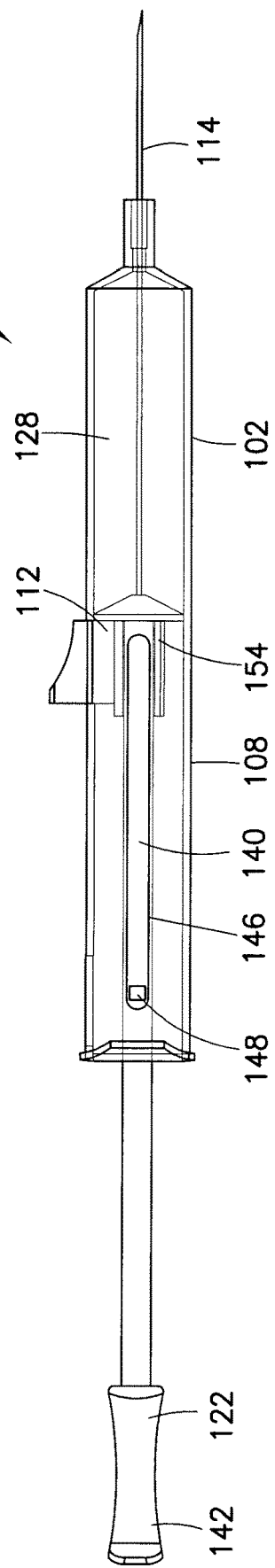
FIG.10
FIG.11

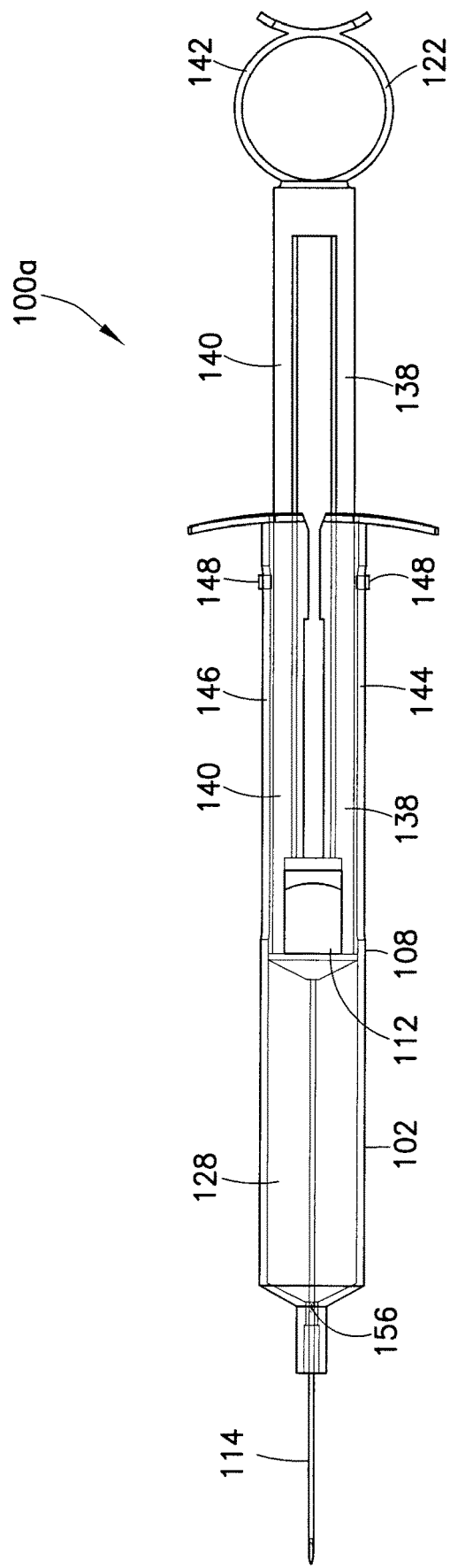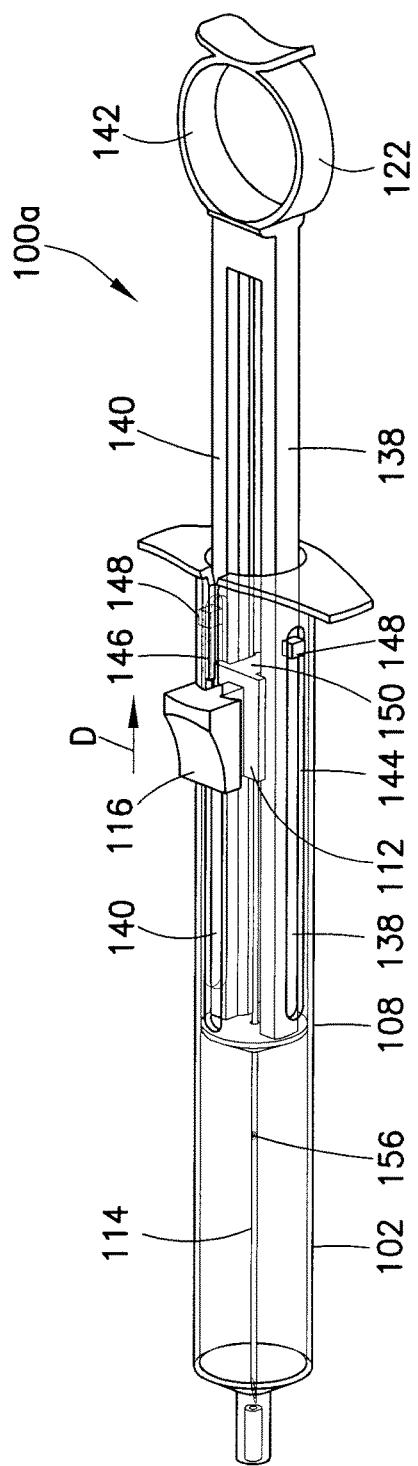
FIG.12
FIG.13

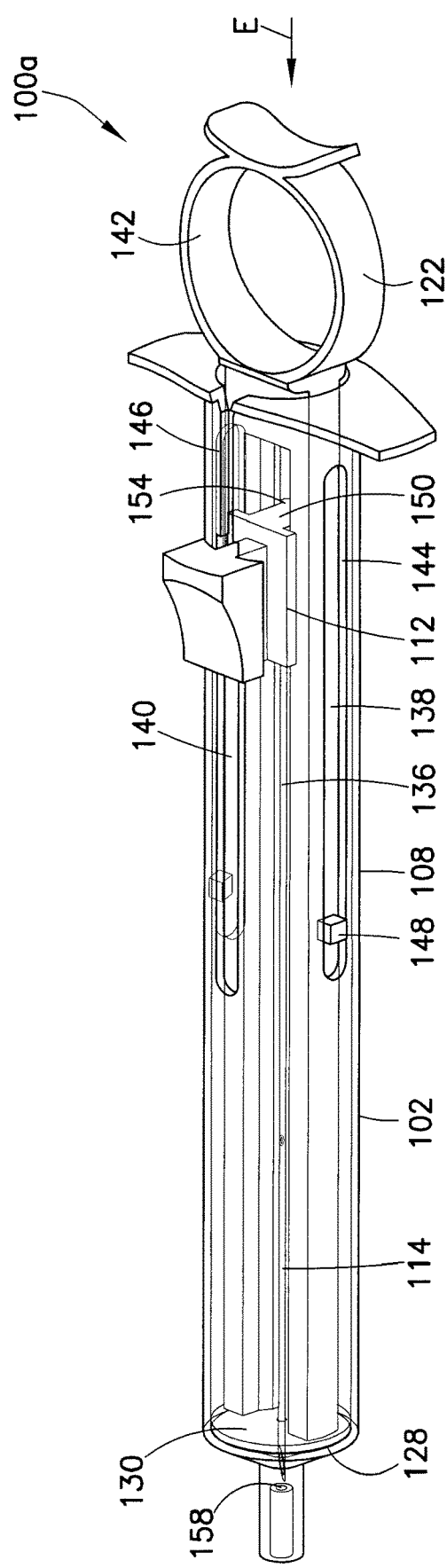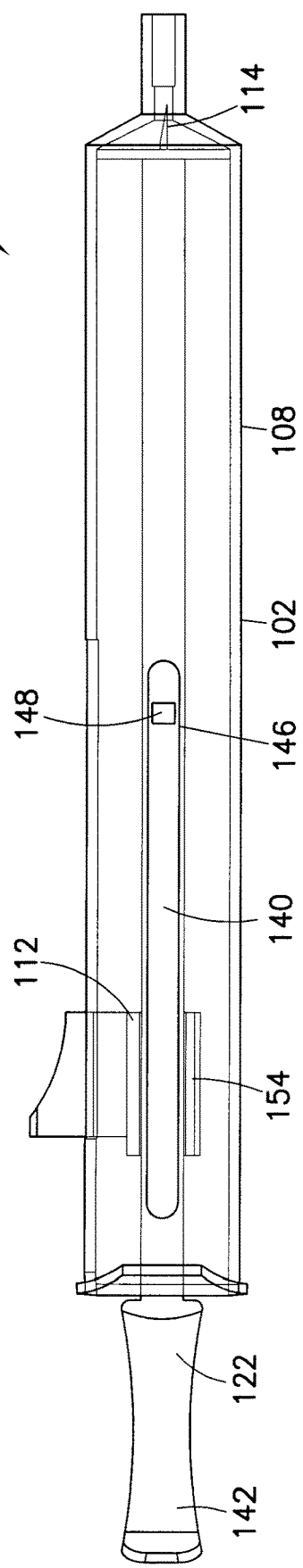

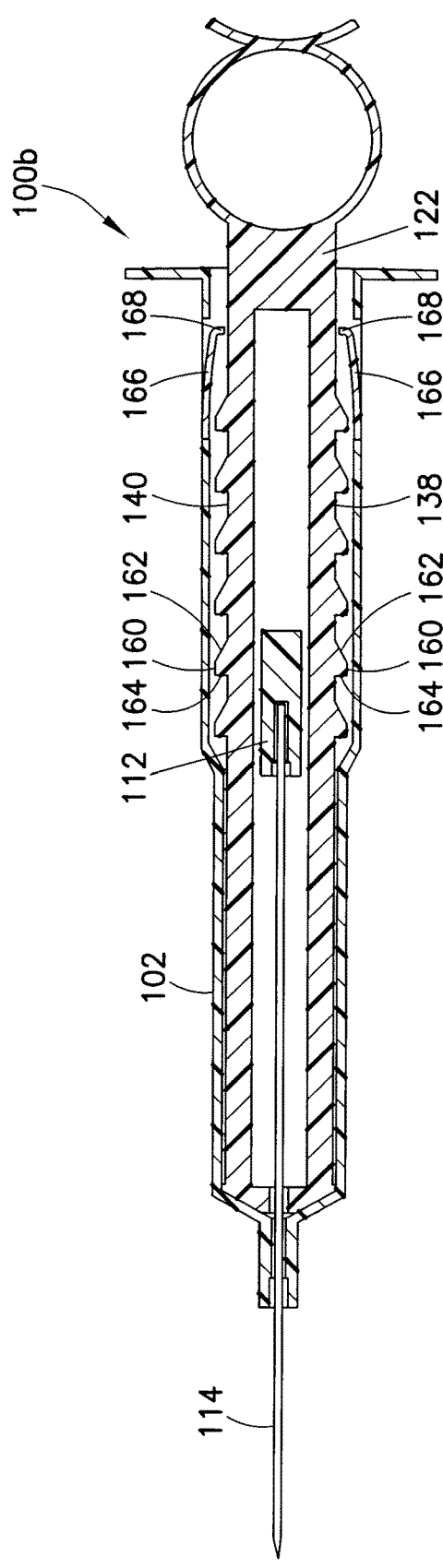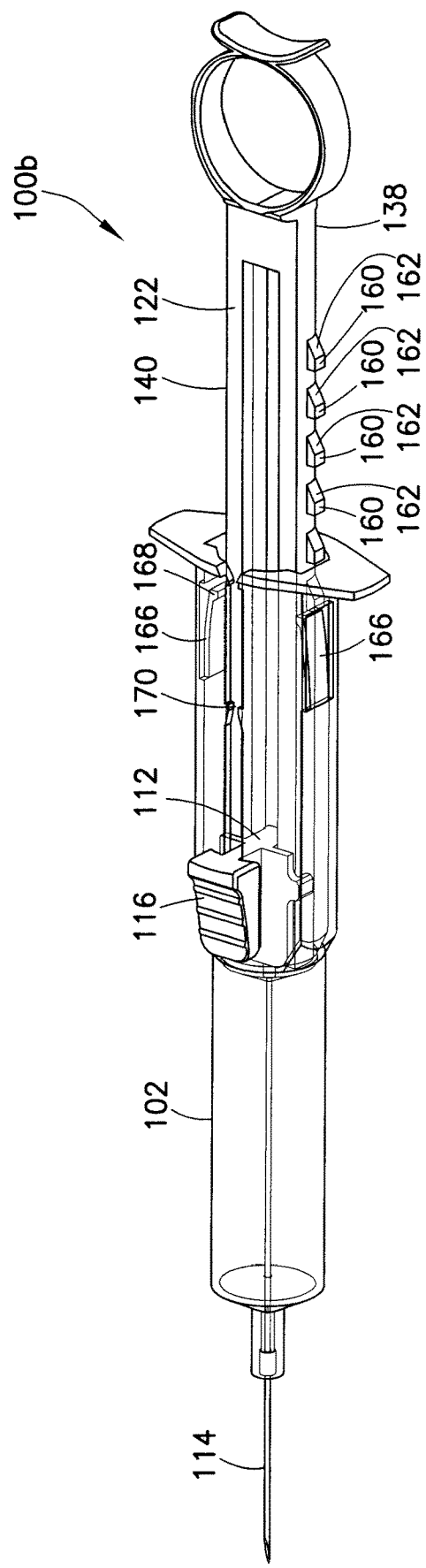
FIG.22
FIG.23

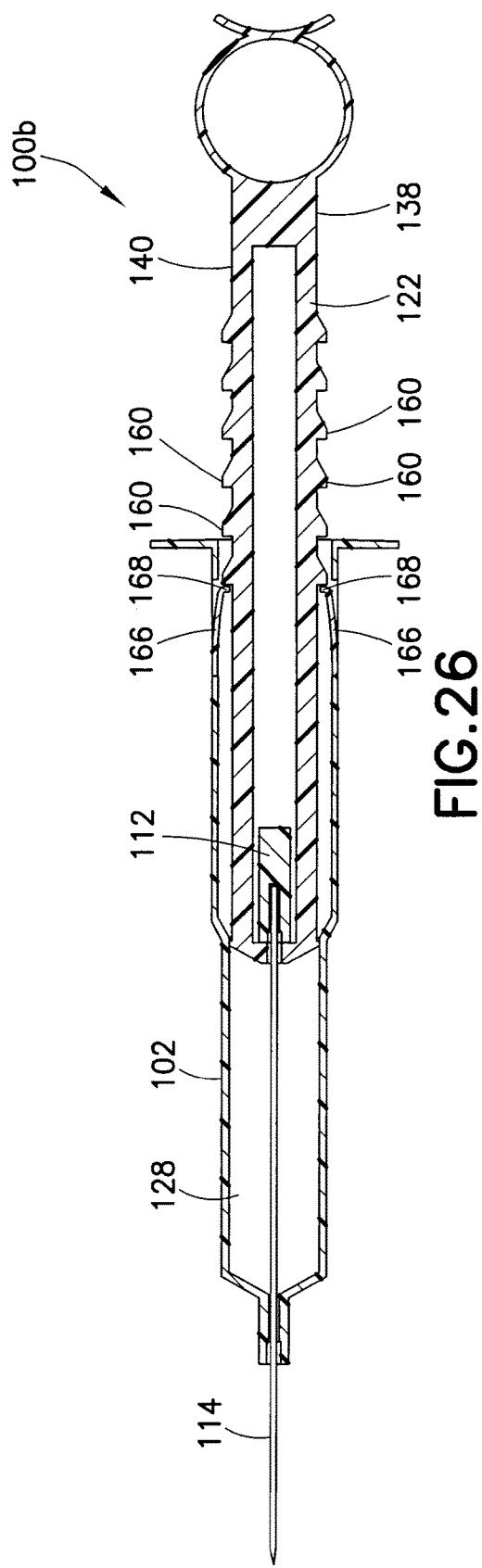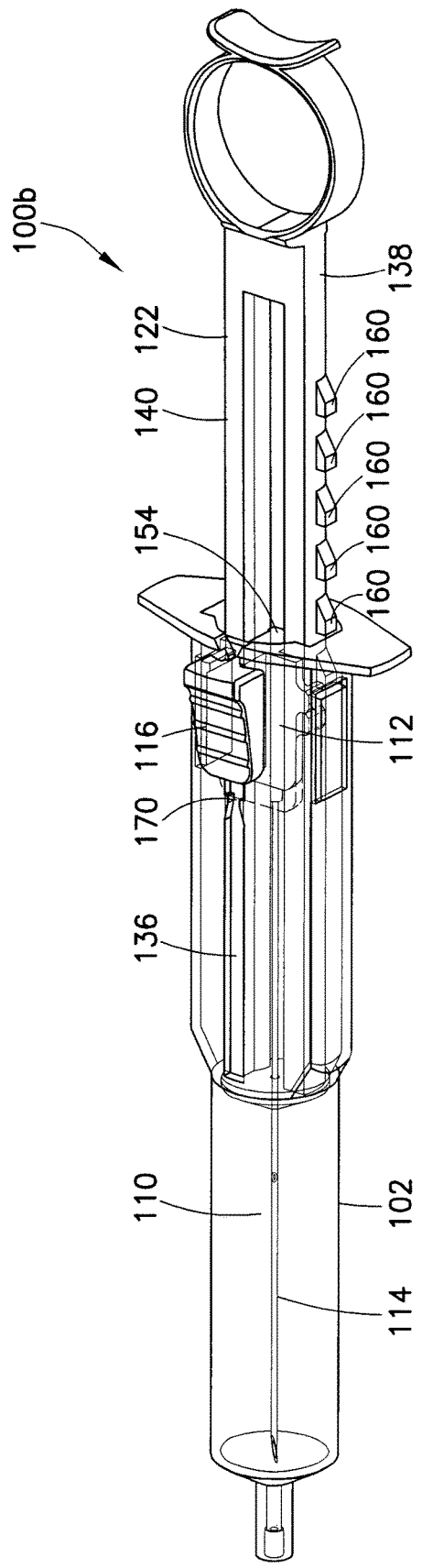

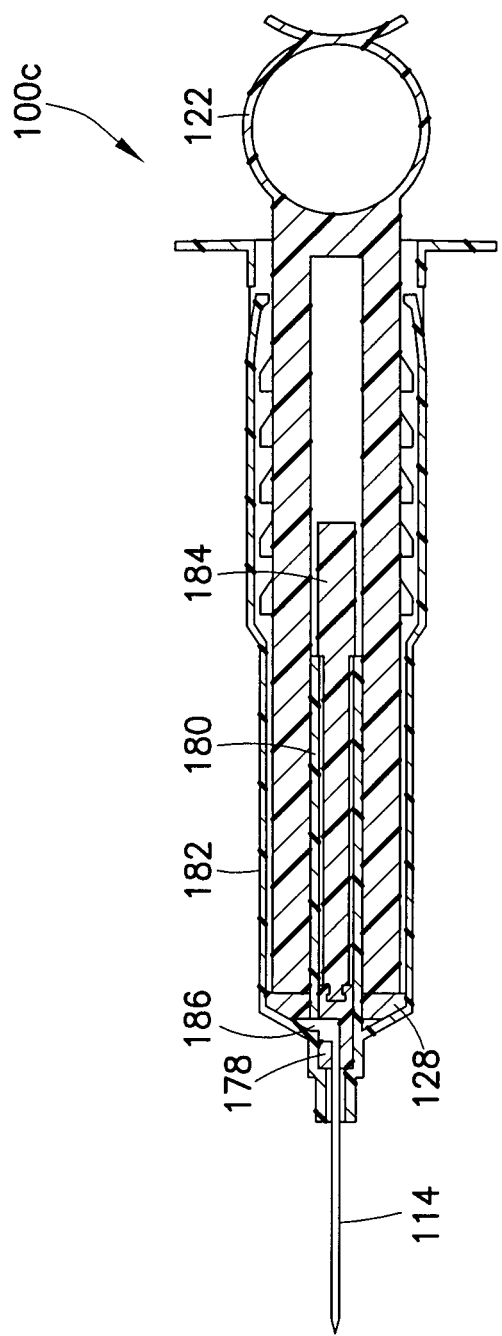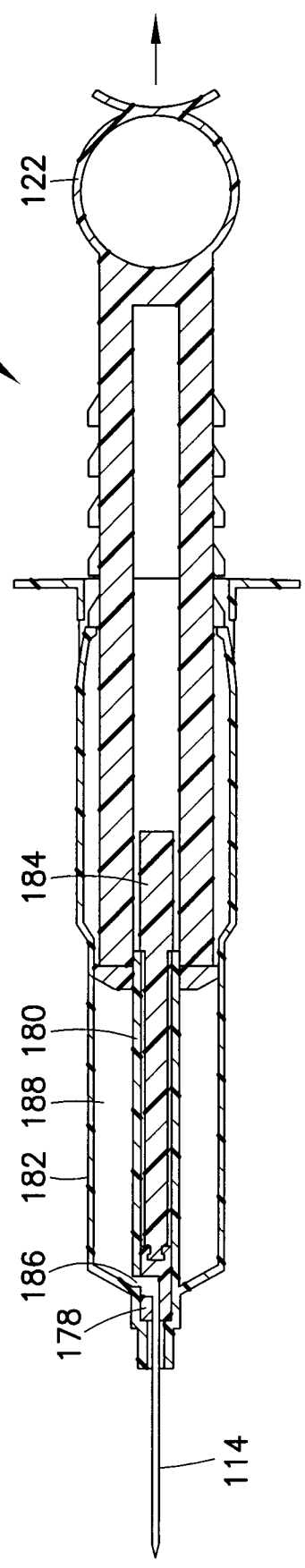

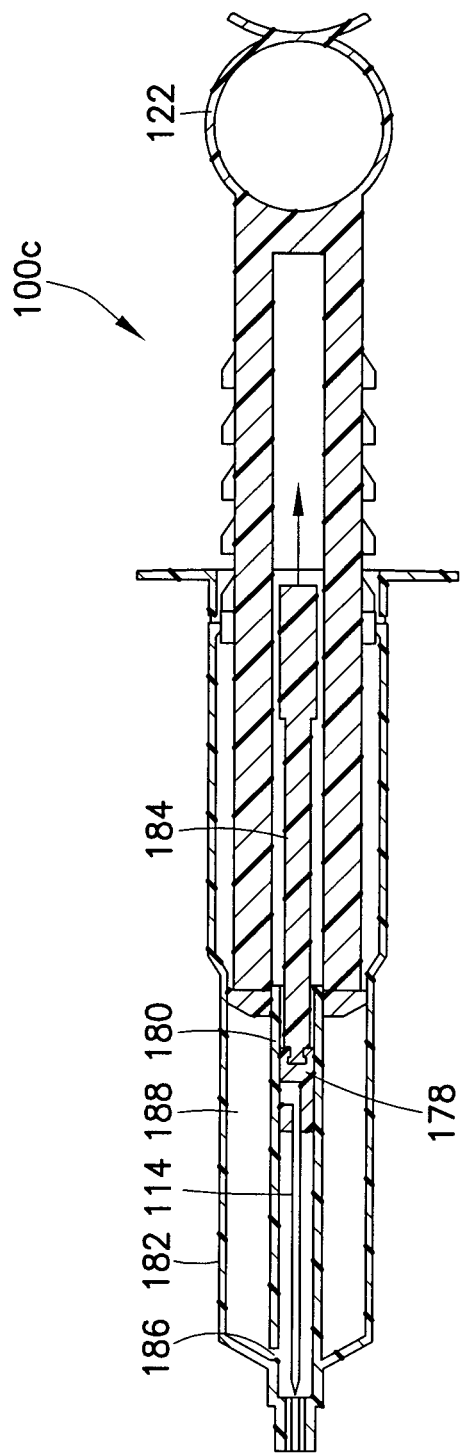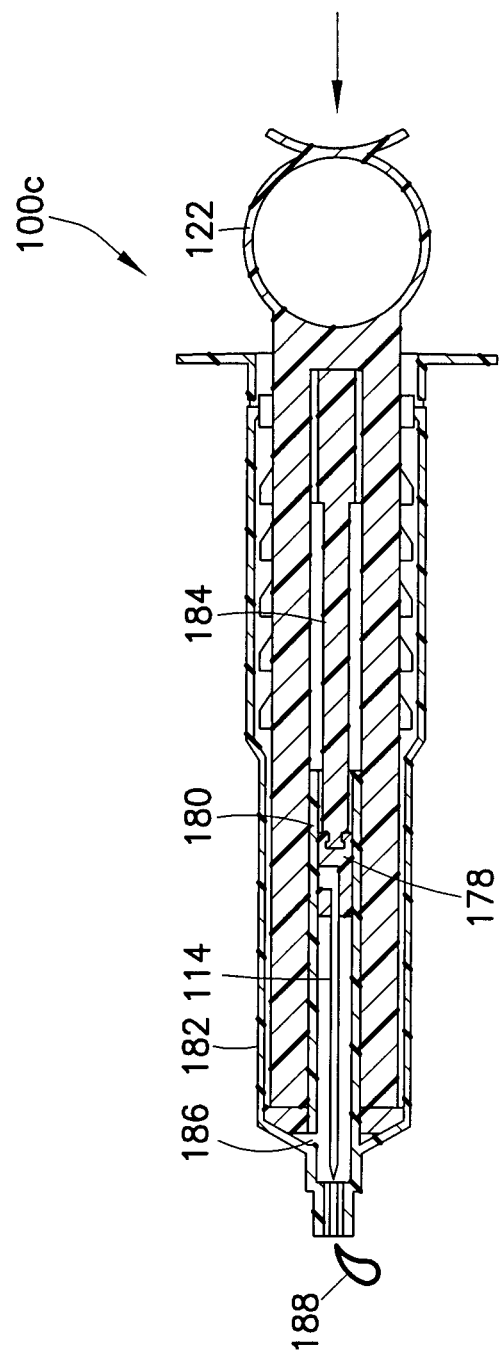
FIG.38
FIG.39

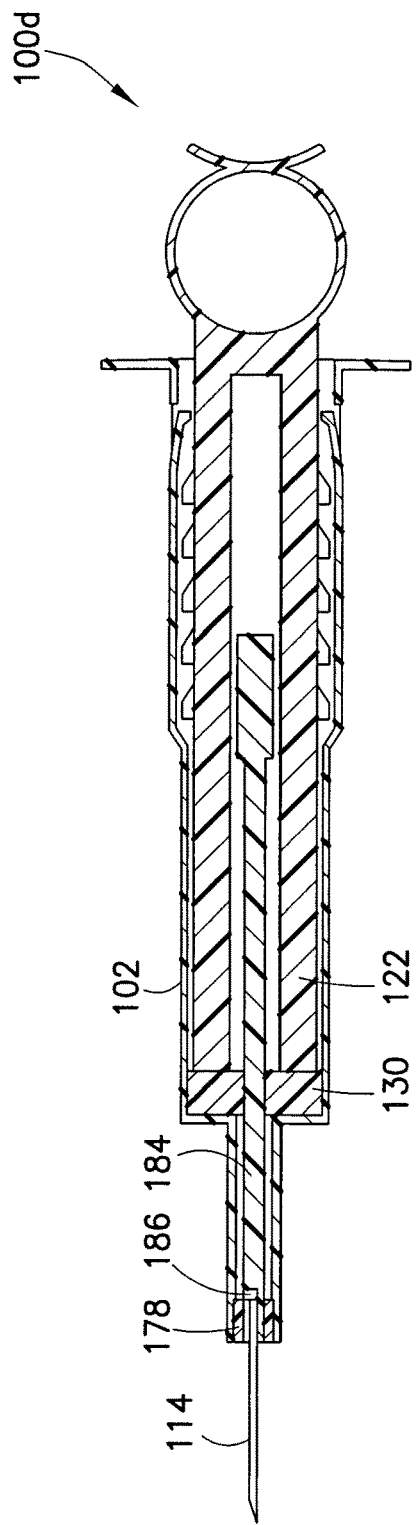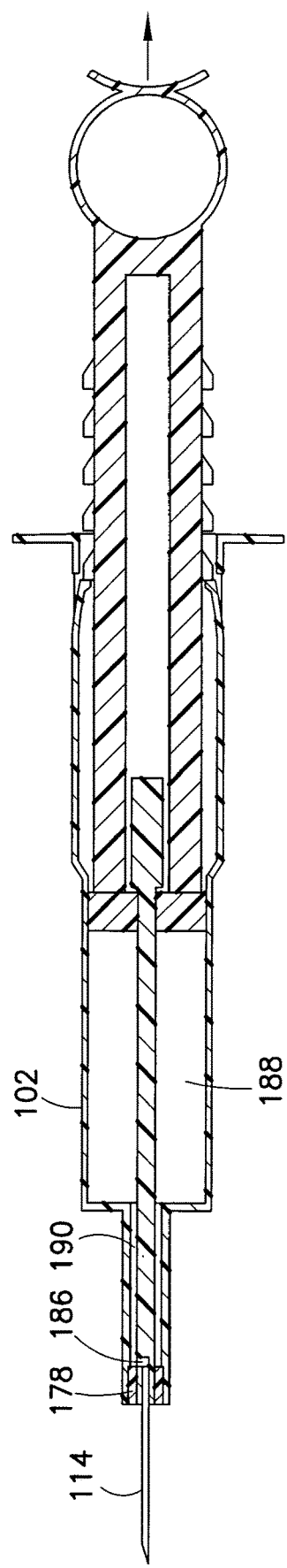
FIG. 42
FIG. 43

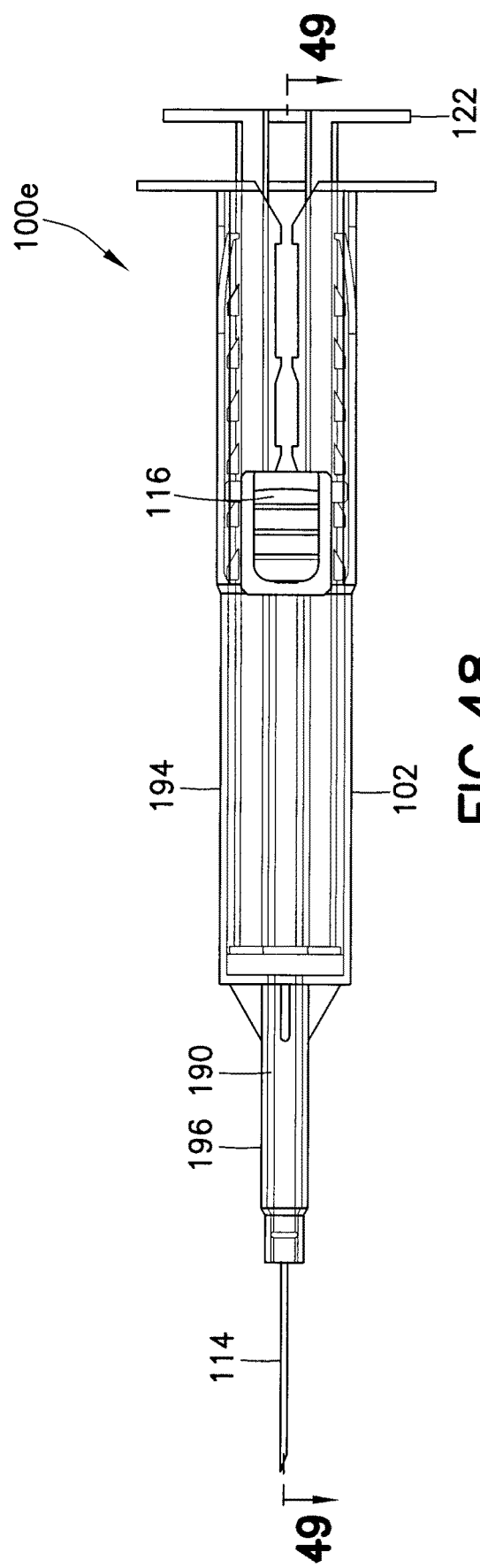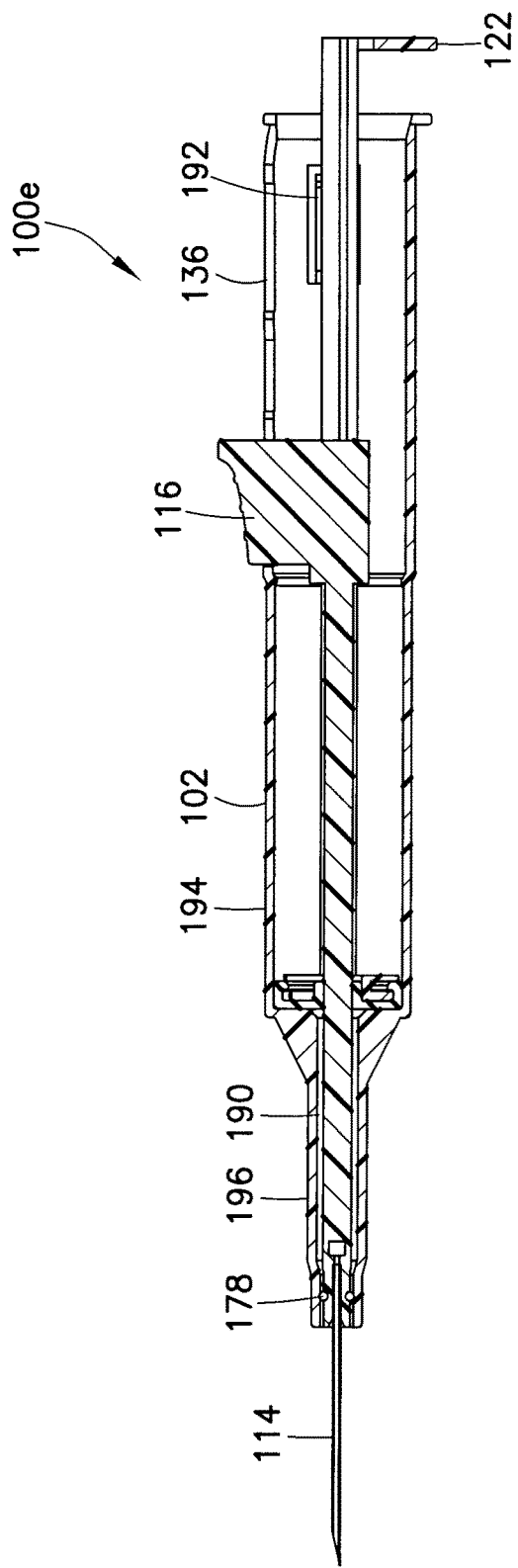
FIG. 48
FIG. 49

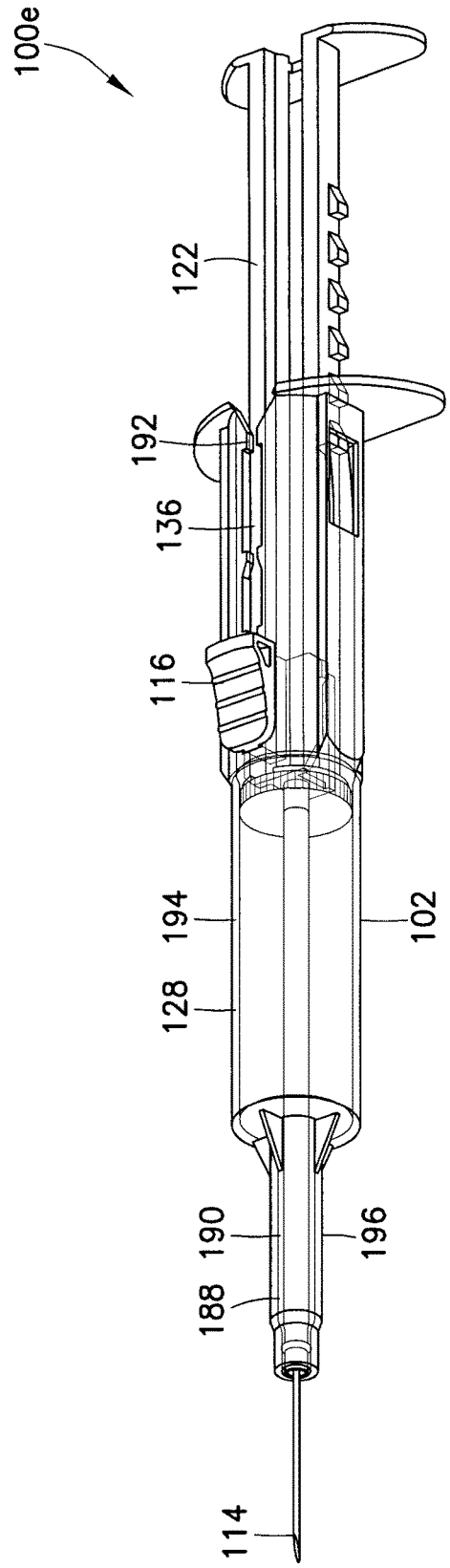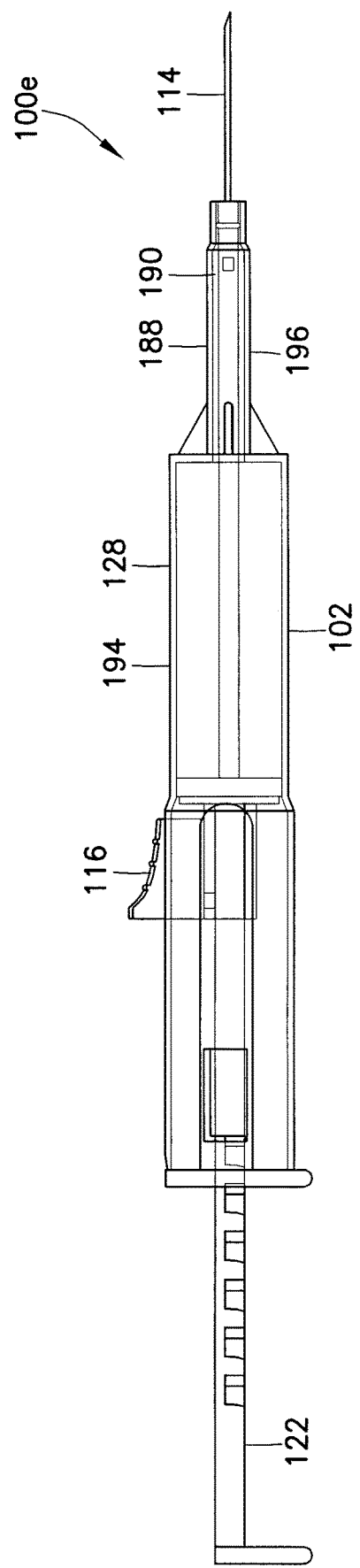
FIG.50
FIG.51

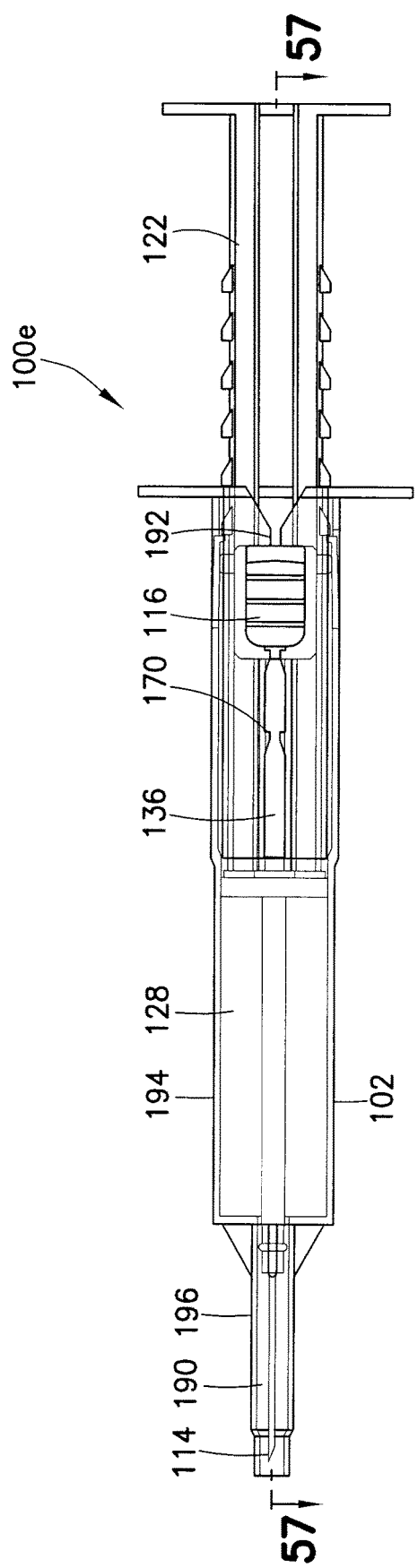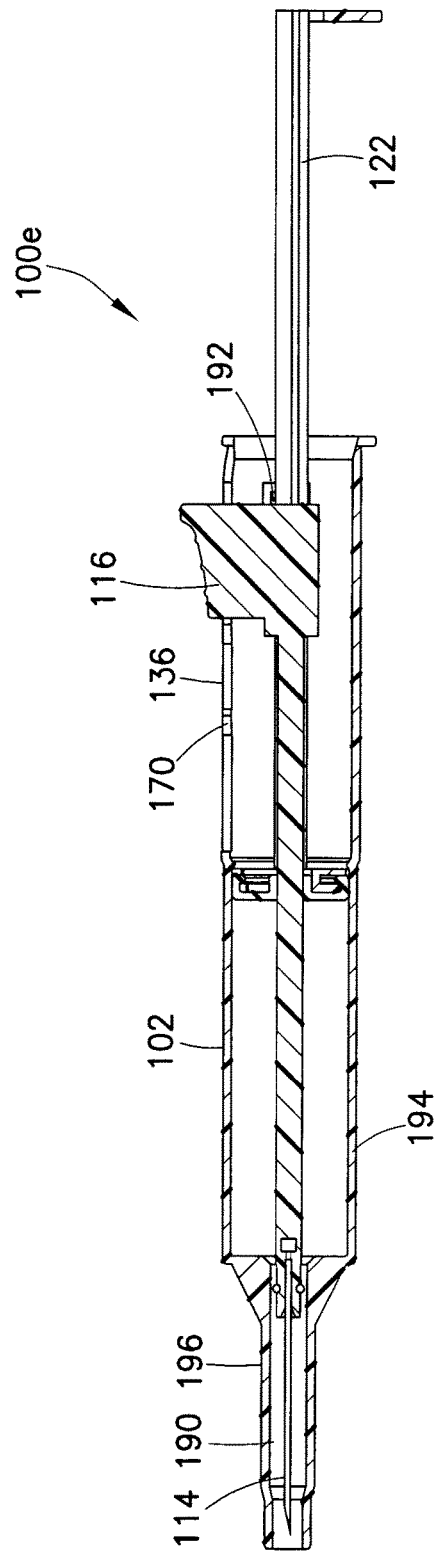
FIG.56
FIG.57

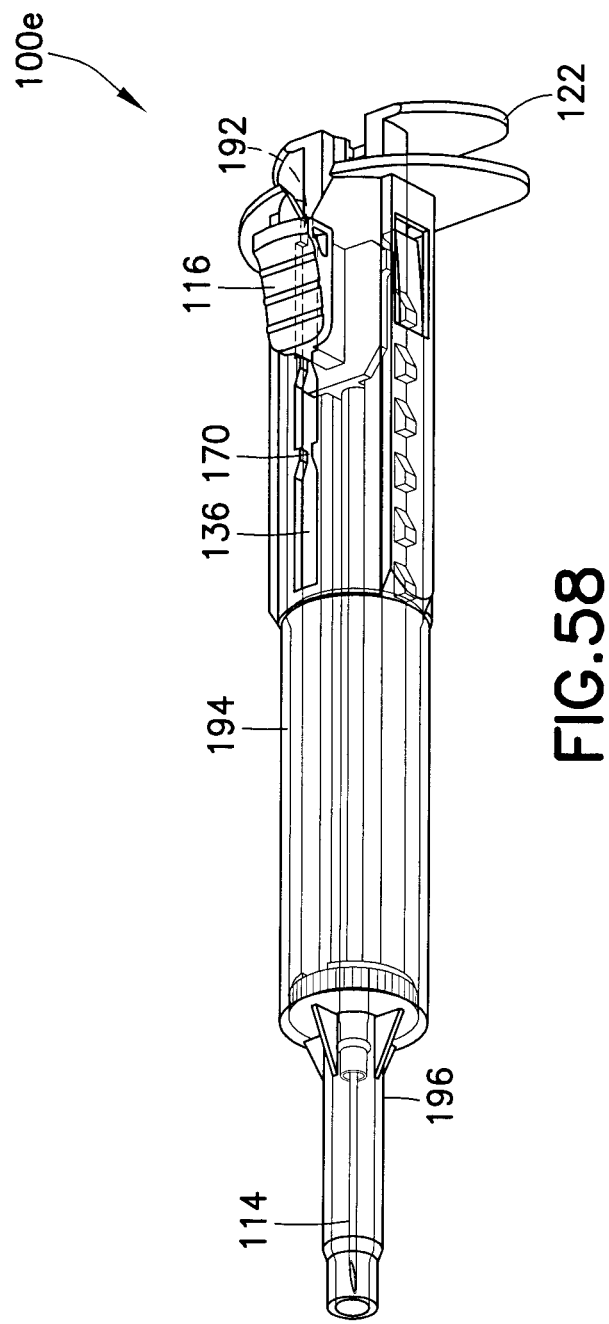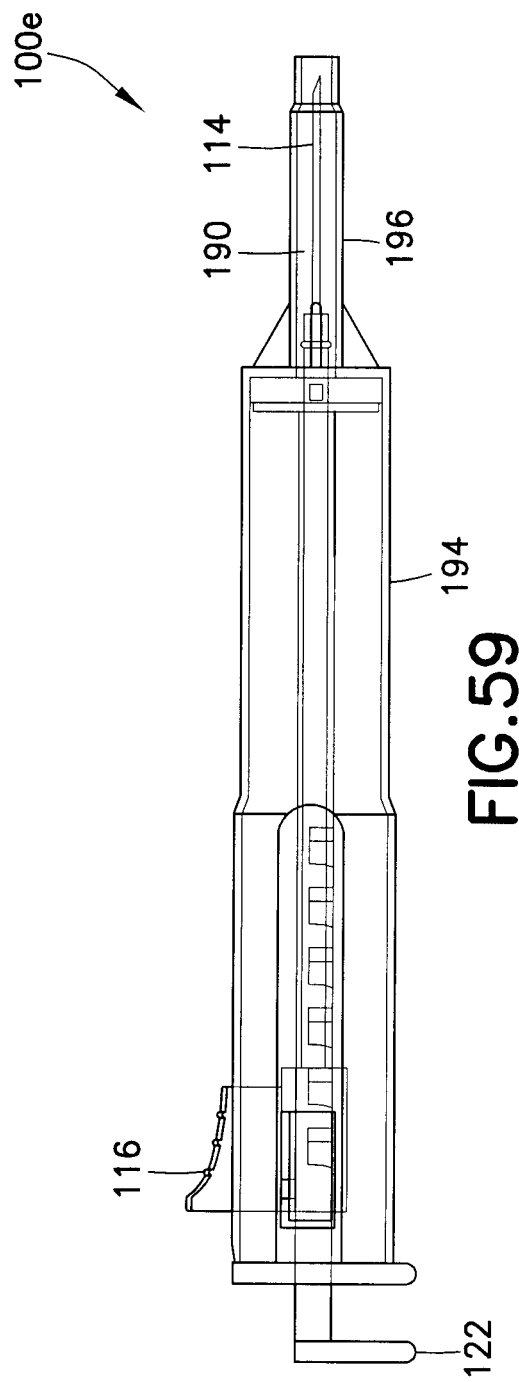

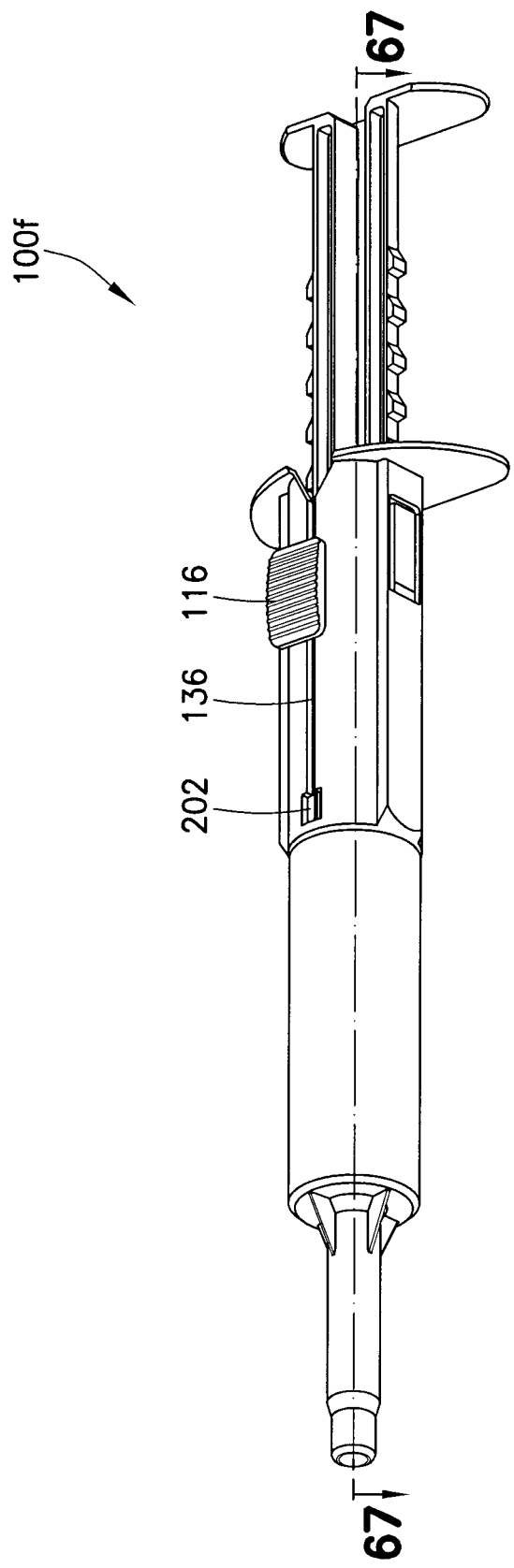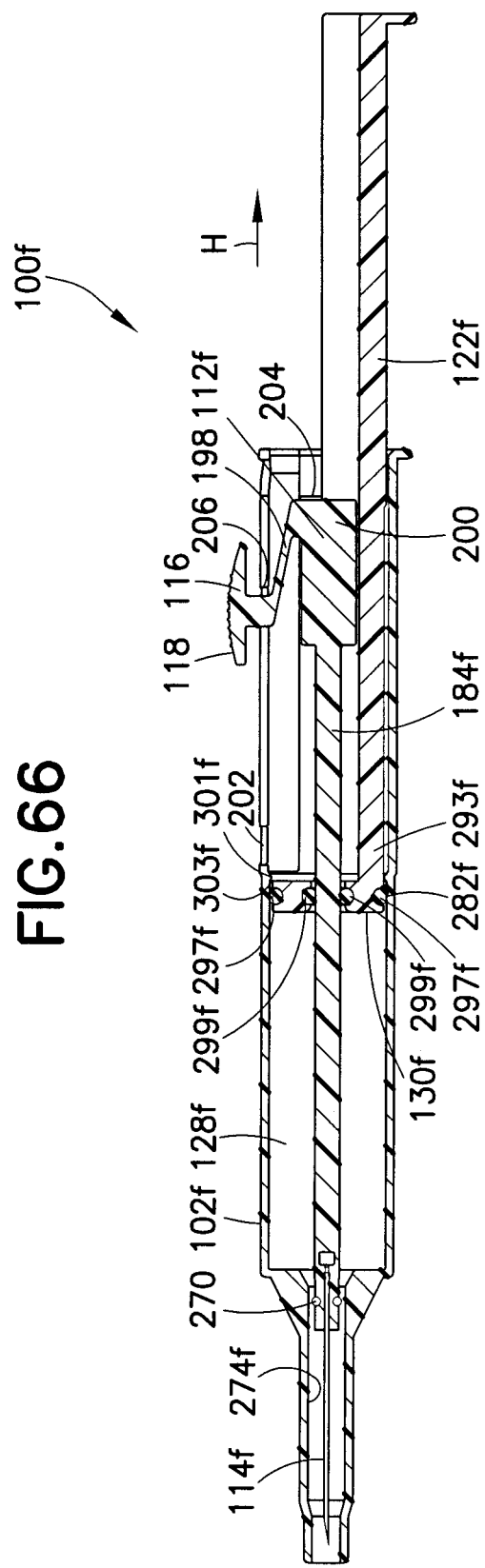

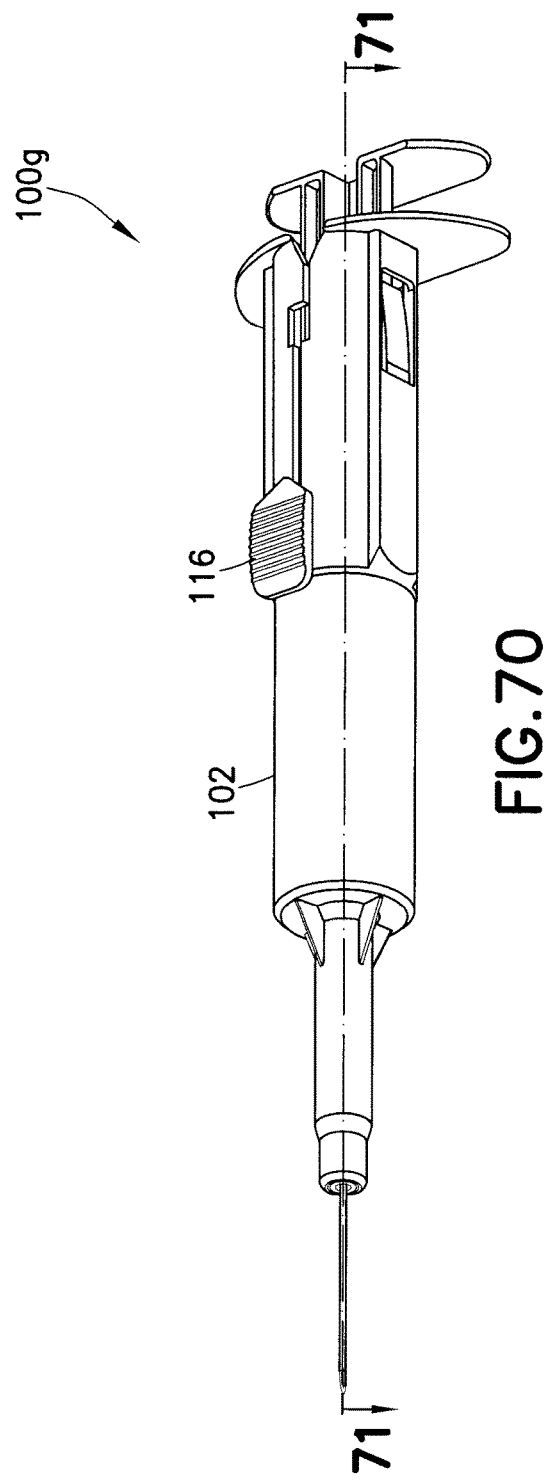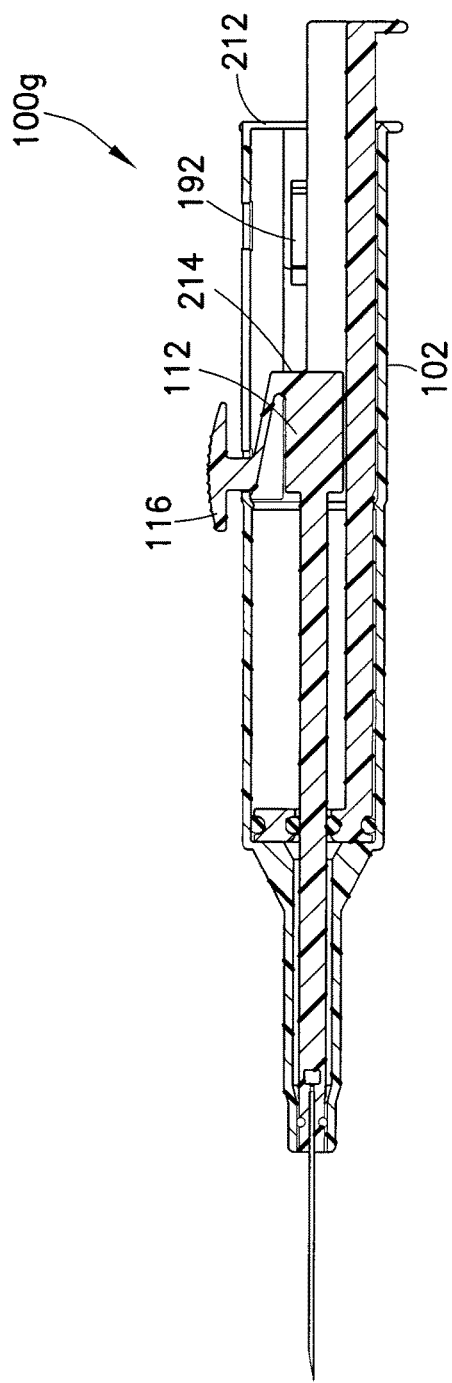
FIG.70
FIG.71

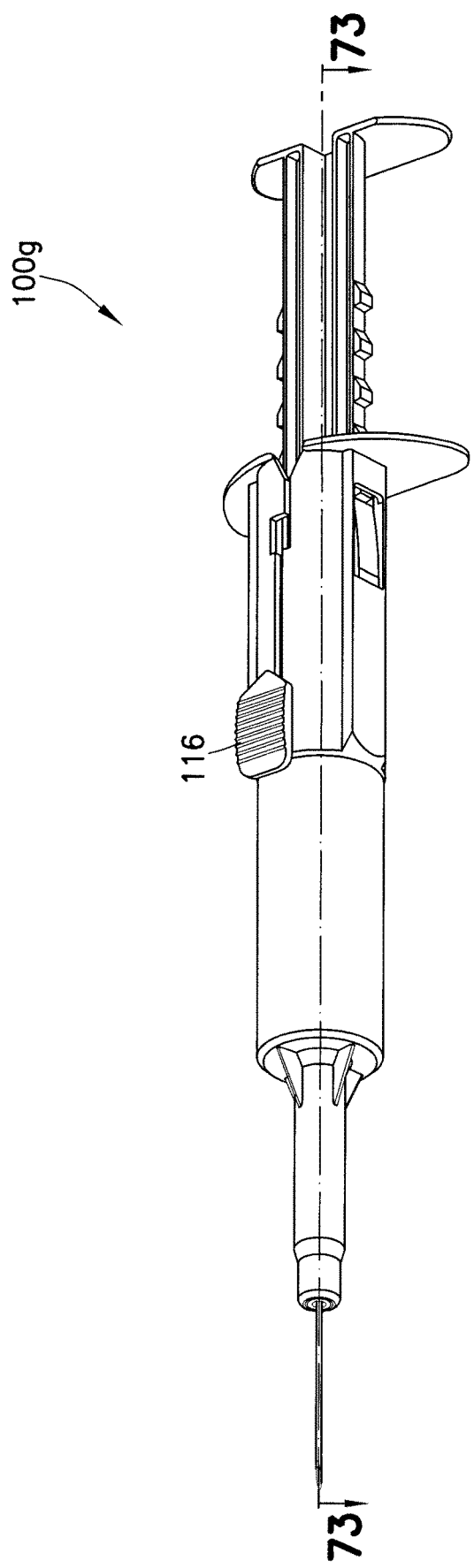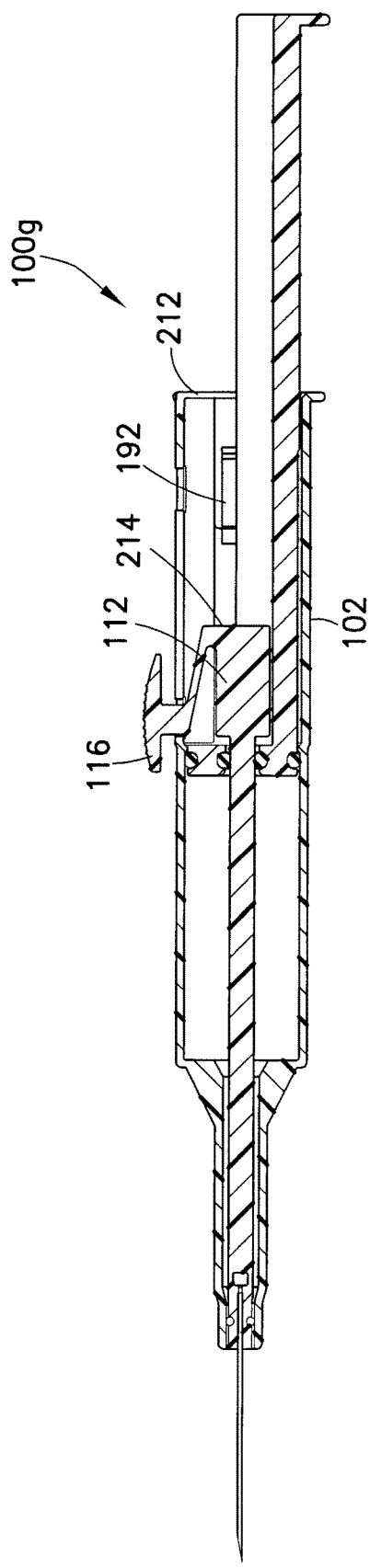
FIG.72
FIG.73

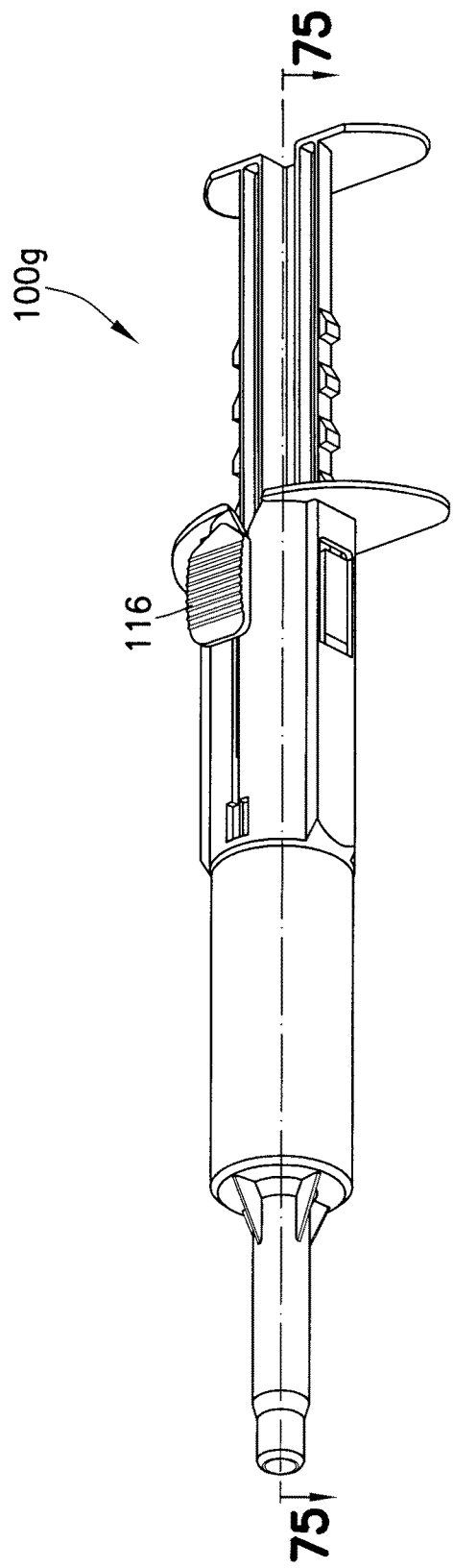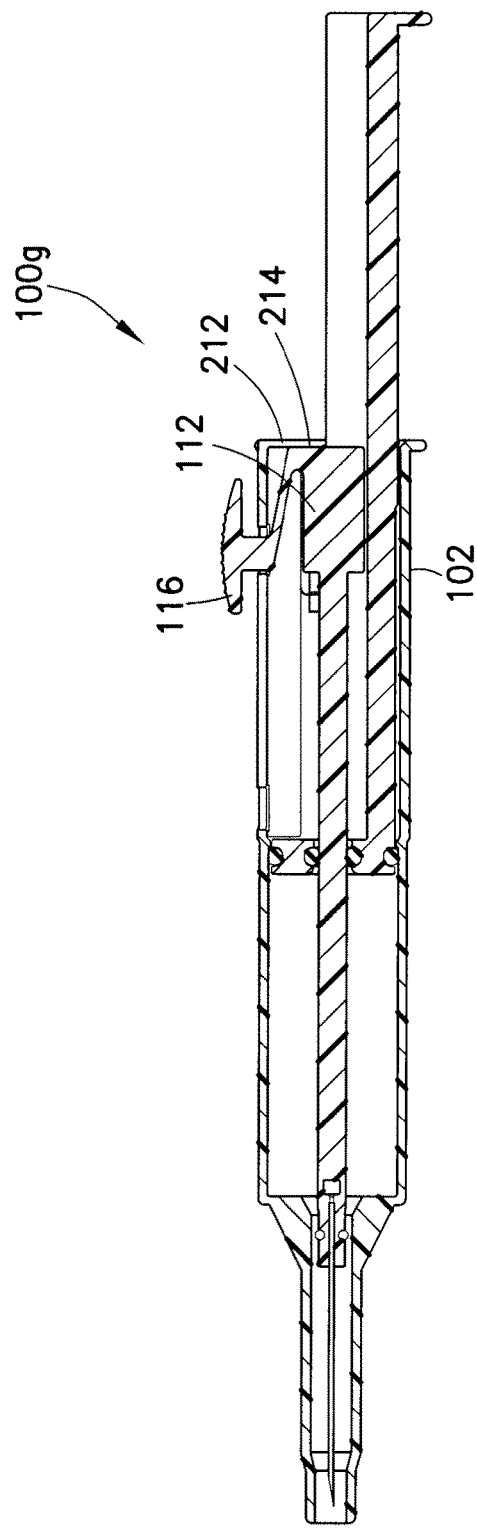
FIG.74
FIG.75

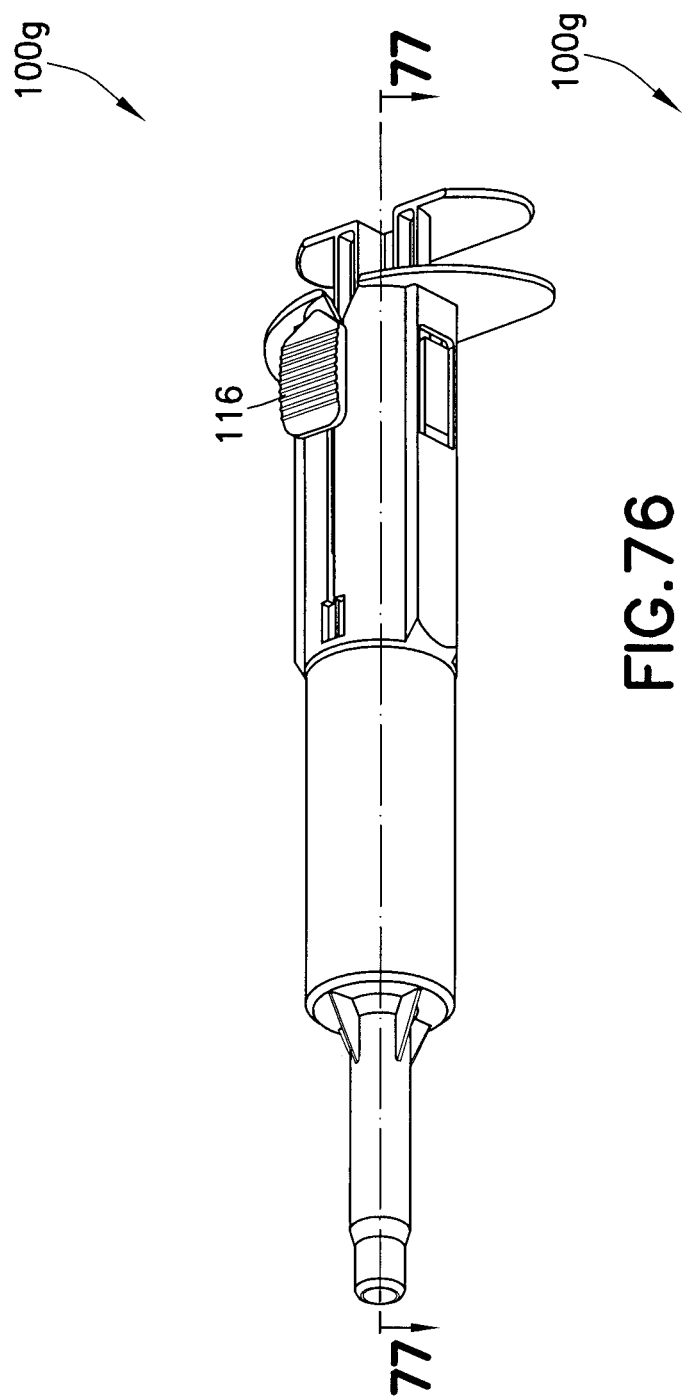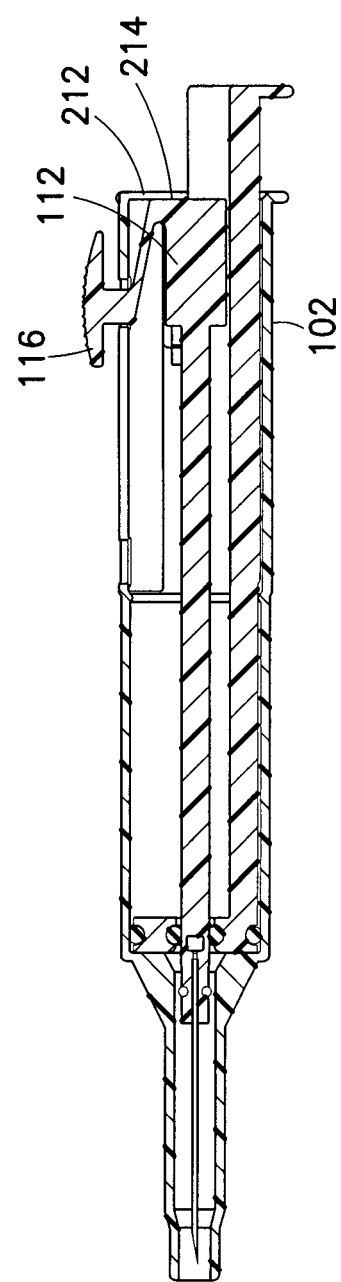
FIG. 76
FIG. 77

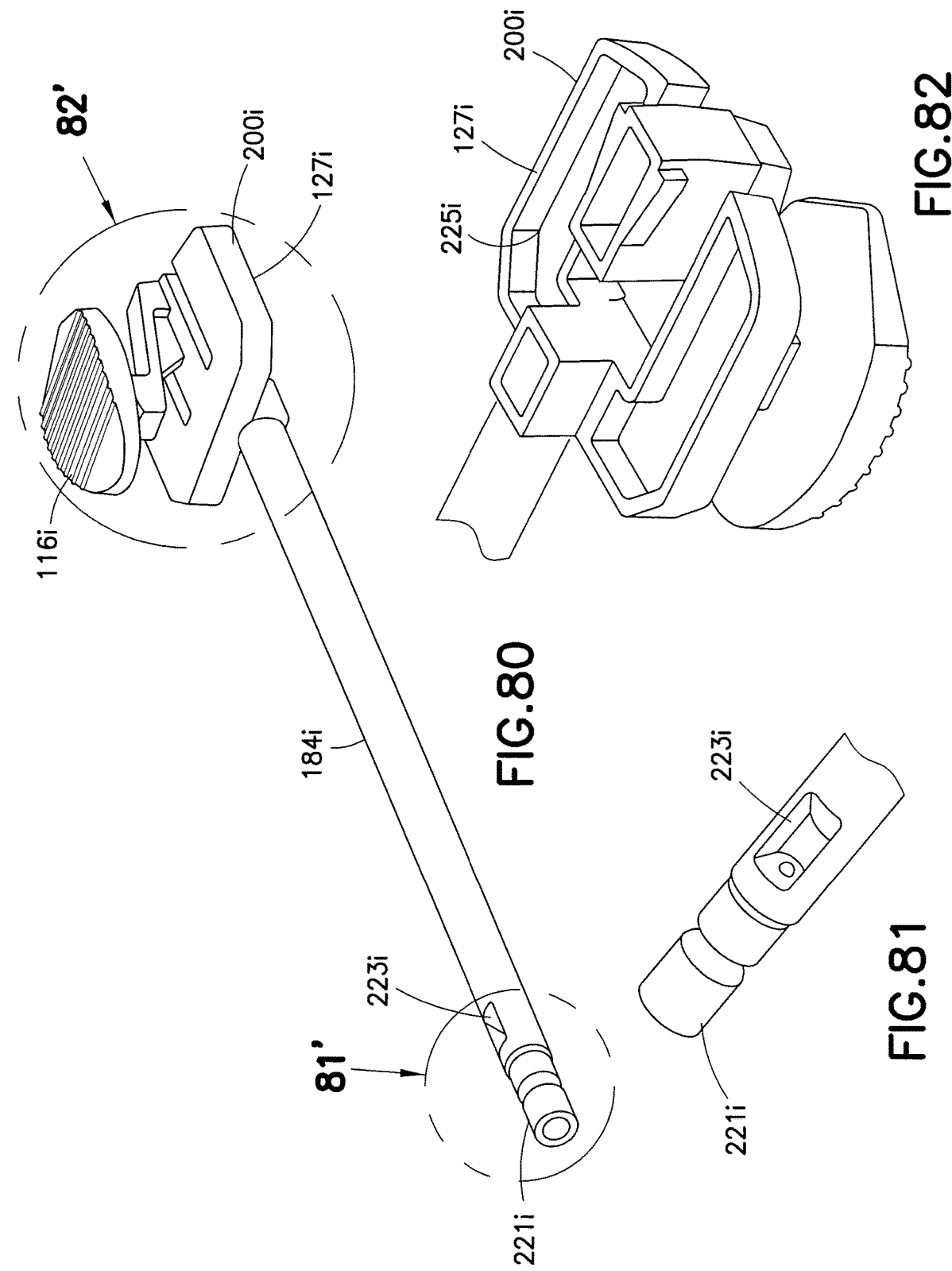

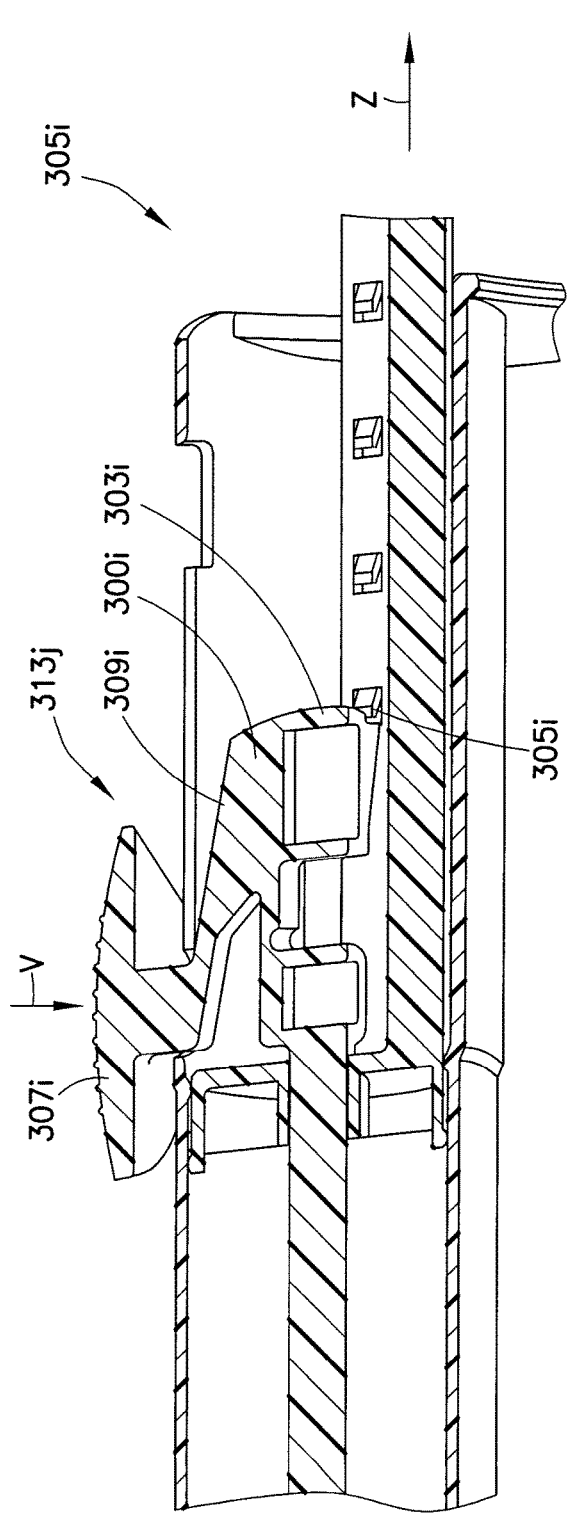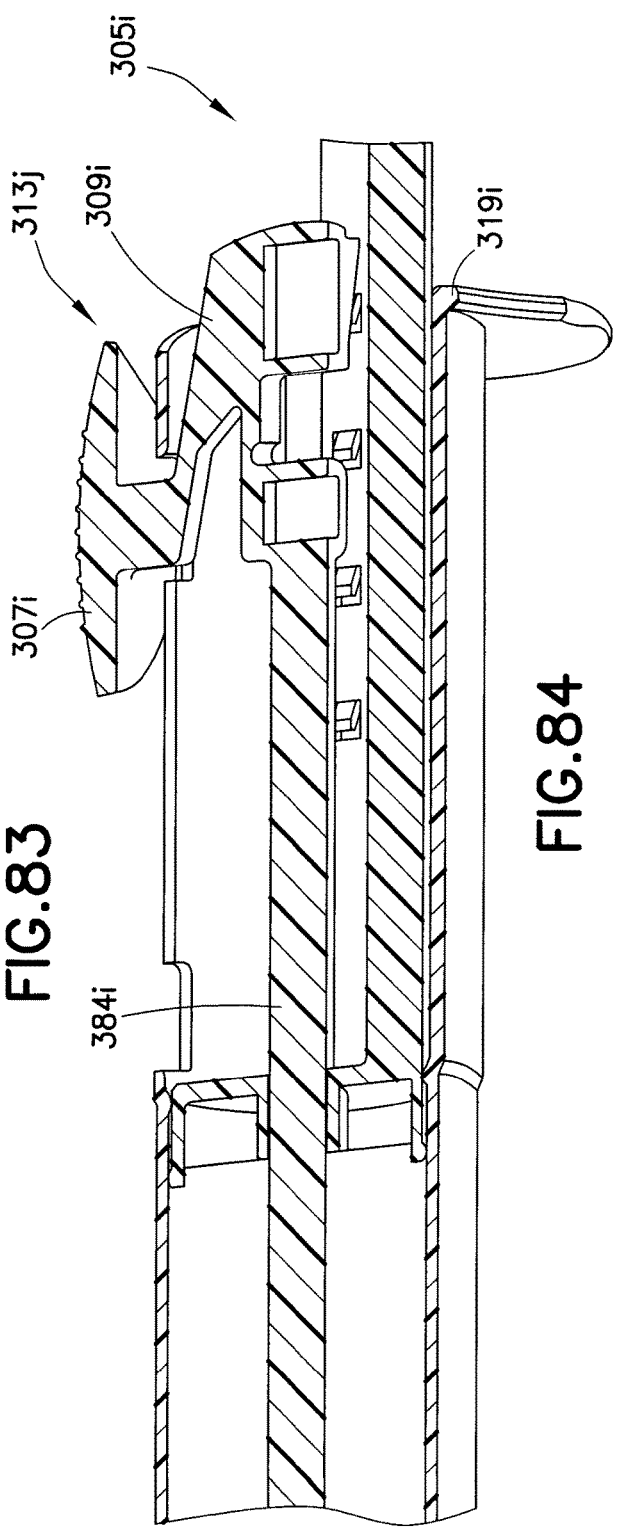

SAFETY SYRINGE HAVING A MANUALLY ACTIVATED RETRACTABLE NEEDLE

CROSS-REFERENCE TO RELATED APPLICATION

This application is a continuation of U.S. patent application Ser. No. 13/492,245 filed Jun. 8, 2012, which claims priority to U.S. Provisional Patent Application Ser. No. 61/494,615 filed Jun. 8, 2011, the entire disclosures of each of which are hereby incorporated by reference.

BACKGROUND OF THE INVENTION

Field of the Invention

The subject invention relates to a device for withdrawing a fluid specimen from a patient and subsequently dispensing the collected fluid into a collection container. More particularly, this invention relates to a safety syringe for withdrawing a fluid specimen, such as blood, from a patient, retracting the needle element of the device into the housing of the device, and subsequently dispensing the collected fluid into a separate collection container.

Description of Related Art

Hypodermic syringes are widely used in the medical arts for withdrawing fluid samples from a patient. Generally, hypodermic syringes have a metal needle that has a sharpened distal point for penetrating a patient's skin that is either fixedly or removably attached to a housing. With the recognition of fluid borne diseases that are transmitted by bodily fluids, and greater sensitivity of the need to protect healthcare workers from inadvertent contact with previously used needles (commonly referred to as "sharps"), as well as the need to reduce criminal misuse of improperly disposed needles and syringes, syringes that include provisions to better shield healthcare workers have been developed.

A variety of shielding mechanisms have also been developed to reduce the incidence of inadvertent exposure of healthcare workers to sharps, however, most of these devices can be compromised by an individual determined to obtain and misuse a hypodermic syringe after its intended use. As a result, further developments in the art of hypodermic syringes have resulted in the advent of hypodermic syringes having needles that withdraw into the body of the syringe once their intended use is completed.

Most of the conventional syringe assemblies in which the needle is withdrawn into the body of the syringe require manufacture and assembly of parts with tight tolerance requirements. Many of the designs depend upon a careful application of forces by the practitioner to draw and/or expel fluids from the syringe. In these assemblies, deviance from the tight tolerances of the multiple components of the device during manufacture and assembly may result in premature activation of the retraction function of the syringe. In addition, conventional syringe assemblies, including a retraction aspect, have been developed for the limited purpose of injecting a medication into a patient, and do not address the need for a syringe used for bodily fluid collection having a retraction element.

Current conventional syringes are used for a variety of different procedures involving both "one-shot" fill and inject procedures, as well as more complex mixing, measuring, and delivery functions. In order for a retractable syringe to displace these functional, utilitarian, and reliable conventional syringes, the new retractable syringe should not interfere with current practices, should be cost-effective, and must be substantially reliable. Current conventional syringes are often manufactured at rates of several hundred per minute and their cost is generally not a significant factor in their usage. One skilled in the art of high volume manufacturing recognizes that assembling hundreds of millions of complex retraction syringes having retraction elements contained in a small space, for example on the order of a one-quarter inch diameter bore, is a daunting task.

Accordingly, a need exists for a retractable syringe that is suitable for use as a bodily fluid collection device for subsequent transfer to a collection container. A need further exists for a retractable syringe that is capable of being manufactured at high volumes, and is sufficiently reliable in use when produced at high volume. Such a device is disclosed herein below. A still further need exists for a safety syringe that provides improved quality of sample transferred to a secondary container.

SUMMARY OF THE INVENTION

In accordance with an embodiment of the present invention, a retractable needle assembly for fluid collection includes a housing having a proximal end and a distal end and a sidewall defining a hollow bore extending between the proximal end and the distal end. The assembly also includes an elongate plunger having a proximal end and a distal end, with the distal end of the plunger forming a reservoir within the hollow bore for containing a fluid therein. The plunger is adapted for slideable movement within the hollow bore. The assembly further includes a hub disposed at least partially within the hollow bore and at least partially supporting a cannula therewith. The assembly also includes a needle retraction member engaged with the hub for manually selectable advancement with respect to a portion of the housing. The needle retraction member may be advanced from an initial position in which at least a portion of the needle is disposed outside the barrel, to a retracted position in which the needle is fully surrounded by the barrel. The elongate plunger may be advanced about at least a portion of the hub for extracting the fluid into the reservoir or expelling the fluid from the reservoir.

In one configuration, the assembly also includes an elastomeric stopper connected to the distal end of the elongate plunger and slideably advanceable within the hollow bore to form a substantially fluid-tight seal therewith. The stopper may be disposed within the hollow bore at a location distal to the hub. The needle retraction member may extend at least partially through a portion of the sidewall of the housing. In certain configurations, the hub and the needle retraction member are co-formed.

Optionally, the needle assembly may include a seal disposed within the hollow bore and positioned about a portion of the needle when the needle is in the initial position so as to form a fluid-tight chamber within the reservoir. The needle may include a break surrounded by the reservoir to allow for fluid entering the needle to pass into the reservoir.

In other configurations, retraction of the elongate plunger from an initial position in which the plunger is substantially disposed within the hollow bore, to a retracted position in which the plunger is substantially disposed exterior to the hollow bore, induces a vacuum within the reservoir to draw fluid therein. The transition of the needle retraction member from the initial position to the retracted position permits redeployment of the elongate plunger within the hollow bore to expel fluid from the reservoir. In specific configurations, the elongate plunger may include a pair of depending arms, with each arm including a protrusion slideably disposed within a corresponding groove defined within the sidewall of the housing.

The needle assembly may also include a lock for preventing re-deployment of the needle retraction member once the needle retraction member has been transitioned from the initial position to the retracted position. The elongate plunger may include a plurality of ramped stops disposed about a length of the plunger extending between the distal end and the proximal end. The proximal end of the housing may define at least one restraint adapted to receive a ramped stop therein, such that advancement of the plunger with respect to the proximal end of the housing in the proximal direction is permitted and advancement of the plunger with respect to the proximal end of the housing in the distal direction is restrained by the interaction of at least one ramped stop and at least one restraint.

The needle retraction member may also include at least one flange adapted to contact at least one protrusion when the elongate plunger is in a fully retracted position to permit re-deployment of the plunger within the hollow bore. Optionally, the distal end of the housing includes a flash chamber for indicating venous access.

In accordance with another embodiment of the present invention, a retractable needle assembly for fluid collection includes a housing having a proximal end and a distal end and a sidewall defining a hollow bore extending between the proximal end and the distal end. The assembly also includes an elongate plunger having a proximal end and a distal end, with the distal end of the plunger forming a reservoir within the hollow bore for containing a fluid therein. The plunger may be adapted for slideable movement within the hollow bore. The assembly also includes a hub disposed at least partially within the hollow bore and at least partially supporting a cannula therewith. A needle retraction member may be engaged with the hub for manually selectable advancement with respect to a portion of the housing. The elongate plunger is transitionable from an initial position in which the plunger is substantially disposed within the hollow bore, to a retracted position in which the plunger is substantially disposed exterior to the hollow bore. The needle retraction member is subsequently transitionable from an initial position in which at least a portion of the needle is disposed outside the barrel, to a retracted position in which the needle is fully surrounded by the barrel. Transition of the needle retraction member from the initial position to the retracted position permits re-deployment of the elongate plunger within the hollow bore.

In certain configurations, the transition of the elongate plunger from the initial position to the retracted position draws fluid into the reservoir, and re-deployment of the elongate plunger from the retracted position expels fluid from the reservoir.

In accordance with yet another embodiment of the present invention, a retractable needle assembly for fluid collection includes a housing having a proximal end and a distal end and a sidewall defining a hollow bore extending between the proximal end and the distal end. The assembly also includes an elongate plunger having a proximal end and a distal end, with the distal end of the plunger forming a reservoir within the hollow bore for containing a fluid therein. The plunger may be adapted for slideable movement within the hollow bore. The assembly also includes a hub disposed at least partially within the hollow bore and at least partially supporting a cannula therewith. A needle retraction member engaged with the hub for manually selectable advancement with respect to a portion of the housing is also provided, wherein the needle retraction member may be advanced from an initial position in which at least a portion of the needle is disposed outside the barrel, to a retracted position in which the needle is fully surrounded by the barrel. Movement of the elongate plunger is isolated from movement of the needle retraction member.

In certain configurations, the elongate plunger is moveable from an initial position in which the plunger is substantially disposed within the hollow bore, to a retracted position in which the plunger is substantially disposed exterior to the hollow bore. The elongate plunger may be subsequently re-deployed within the hollow bore. Optionally, the elongate plunger may be re-deployed subsequent to the advancement of the needle retraction member from the initial position to the retracted position.

Further details and advantages of the invention will become clear from the following detailed description when read in conjunction with the accompanying drawings.

BRIEF DESCRIPTION OF THE DRAWINGS

FIG. 4 is a perspective view of a syringe assembly in an initial position in accordance with an embodiment of the present invention.

FIG. 5 is an alternative perspective view of the syringe assembly of FIG. 4 in accordance with an embodiment of the present invention.

FIG. 6 is a side view of the syringe assembly of FIG. 4 in accordance with an embodiment of the present invention.

FIG. 7 is a top view of the syringe assembly of FIG. 4 in accordance with an embodiment of the present invention.

FIG. 10 is a perspective view of the syringe assembly of FIG. 4 having the plunger withdrawn from the body of the syringe in accordance with an embodiment of the present invention.

FIG. 11 is a side view of the syringe assembly of FIG. 10 in accordance with an embodiment of the present invention.

FIG. 12 is a top view of the syringe assembly of FIG. 10 in accordance with an embodiment of the present invention.

FIG. 13 is a perspective view of the syringe assembly of FIG. 10 having the needle retraction member in the retracted position in accordance with an embodiment of the present invention.

FIG. 16 is a perspective view of the syringe assembly of FIG. 13 having the plunger redeployed within the body of the syringe in accordance with an embodiment of the present invention.

FIG. 17 is a side view of the syringe assembly of FIG. 16 in accordance with an embodiment of the present invention.

FIG. 22 is a cross-sectional view of the syringe assembly of FIG. 19 taken along line 22-22 of FIG. 20 in accordance with an embodiment of the present invention.

FIG. 23 is a perspective view of the syringe assembly of FIG. 19 having the plunger withdrawn from the body of the syringe in accordance with an embodiment of the present invention.

FIG. 26 is a cross-sectional view of the syringe assembly of FIG. 23 taken along line 26-26 of FIG. 24 in accordance with an embodiment of the present invention.

FIG. 27 is a perspective view of the syringe assembly of FIG. 23 having the needle retraction member in the retracted position in accordance with an embodiment of the present invention.

FIG. 36 is a cross-sectional top view of a syringe assembly having a distal seal in the initial position in accordance with an embodiment of the present invention.

FIG. 37 is a cross-sectional top view of the syringe assembly of FIG. 36 having the plunger withdrawn from the body of the syringe in accordance with an embodiment of the present invention.

FIG. 38 is a cross-sectional top view of the syringe assembly of FIG. 36 having the needle retraction member in the retracted position in accordance with an embodiment of the present invention.

FIG. 39 is a cross-sectional top view of the syringe assembly of FIG. 36 having the plunger redeployed within the body of the syringe in accordance with an embodiment of the present invention.

FIG. 42 is a cross-sectional top view of a syringe assembly having a short needle and an extension chamber in the initial position in accordance with an embodiment of the present invention.

FIG. 43 is a cross-sectional top view of the syringe assembly of FIG. 40 having the plunger withdrawn from the syringe body in accordance with an embodiment of the present invention.

FIG. 48 is a top view of the syringe assembly of FIG. 46 in accordance with an embodiment of the present invention.

FIG. 49 is a cross-sectional view of the syringe assembly of FIG. 46 taken along line 49-49 of FIG. 48 in accordance with an embodiment of the present invention.

FIG. 50 is a perspective view of a syringe assembly having the plunger withdrawn from the syringe body in accordance with an embodiment of the present invention.

FIG. 51 is a side view of the syringe assembly of FIG. 50 in accordance with an embodiment of the present invention.

FIG. 56 is a top view of the syringe assembly of FIG. 54 in accordance with an embodiment of the present invention.

FIG. 57 is a cross-sectional view of the syringe assembly of FIG. 54 taken along line 57-57 of FIG. 56 in accordance with an embodiment of the present invention.

FIG. 58 is a perspective view of a syringe assembly having the plunger redeployed within the syringe body in accordance with an embodiment of the present invention.

FIG. 59 is a side view of the syringe assembly of FIG. 58 in accordance with an embodiment of the present invention.

FIG. 66 is a perspective view of the syringe assembly of FIG. 62 having the needle retraction member in the retracted position in accordance with an embodiment of the present invention.

FIG. 67 is a cross-sectional view of the syringe assembly of FIG. 66 taken along line 67-67 in accordance with an embodiment of the present invention.

FIG. 70 is a perspective view of a syringe assembly in an initial position in accordance with an embodiment of the present invention.

FIG. 71 is a cross-sectional view of the syringe assembly of FIG. 70 taken along line 71-71 in accordance with an embodiment of the present invention.

FIG. 72 is a perspective view of the syringe assembly of FIG. 70 having the plunger withdrawn from the syringe body in accordance with an embodiment of the present invention.

FIG. 73 is a cross-sectional view of the syringe assembly of FIG. 72 taken along line 73-73 in accordance with an embodiment of the present invention.

FIG. 74 is a perspective view of the syringe assembly of FIG. 70 having the needle retraction member in the retracted position in accordance with an embodiment of the present invention.

FIG. 75 is a cross-sectional view of the syringe assembly of FIG. 74 taken along line 75-75 in accordance with an embodiment of the present invention.

FIG. 76 is a perspective view of the syringe assembly of FIG. 70 having the plunger redeployed within the syringe body in accordance with an embodiment of the present invention.

FIG. 77 is a cross-sectional view of the syringe assembly of FIG. 76 taken along line 77-77 in accordance with an embodiment of the present invention.

FIG. 80 is a perspective view of a chamber extender and base coupled with a needle retraction member in accordance with an embodiment of the present invention.

FIG. 81 is a close up perspective top view of the distal end of the chamber extender taken along section 81' of FIG. 80 in accordance with an embodiment of the present invention.

FIG. 82 is a close up perspective bottom view of the proximal end of the base coupled with the needle retraction member taken along section 82' of FIG. 80 in accordance with an embodiment of the present invention.

FIG. 83 is a partial cross-sectional perspective view of a retractable needle assembly having a locking mechanism in an initial position in accordance with an embodiment of the present invention.

FIG. 84 is a partial cross-sectional perspective view of the retractable needle assembly of FIG. 83 having the locking mechanism in an extended position in accordance with an embodiment of the present invention.

DETAILED DESCRIPTION OF THE INVENTION

Figure 1:
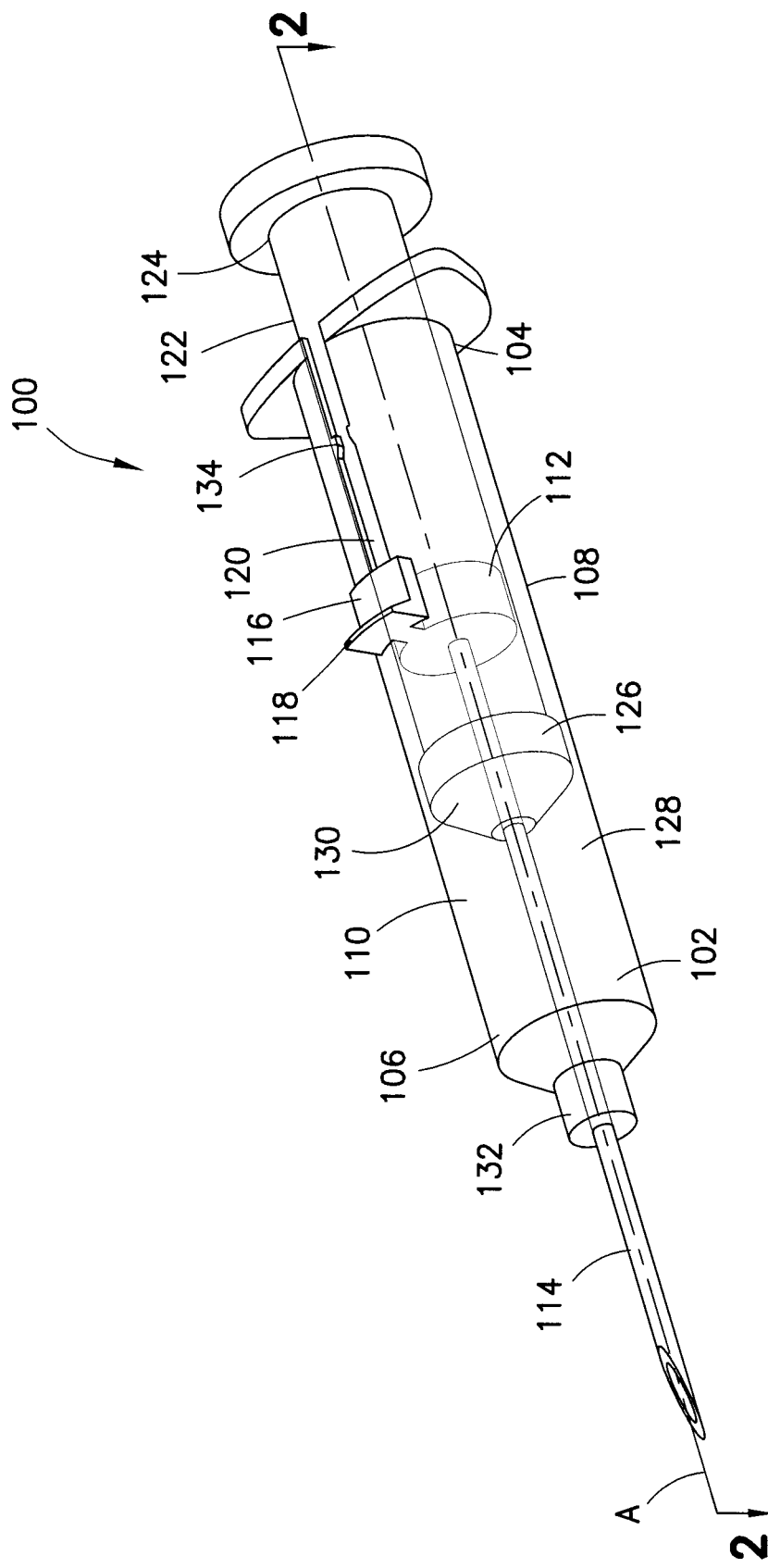
FIG. 1 is a perspective view of a syringe assembly in accordance with an embodiment of the present invention.

For purposes of the description hereinafter, the words "upper", "lower", "right", "left", "vertical", "horizontal", "top", "bottom", "lateral", "longitudinal", and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

Figure 2:
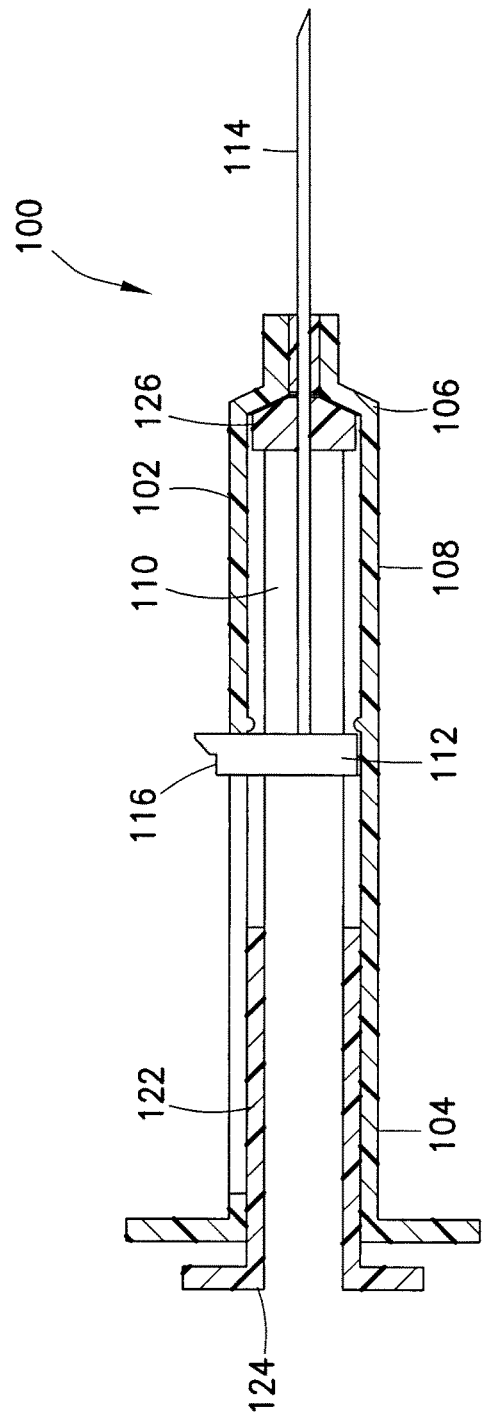
FIG. 2 is a cross-sectional side view of the syringe assembly of FIG. 1 in the initial position as taken along line 2-2 in accordance with an embodiment of the present invention.
Figure 3:
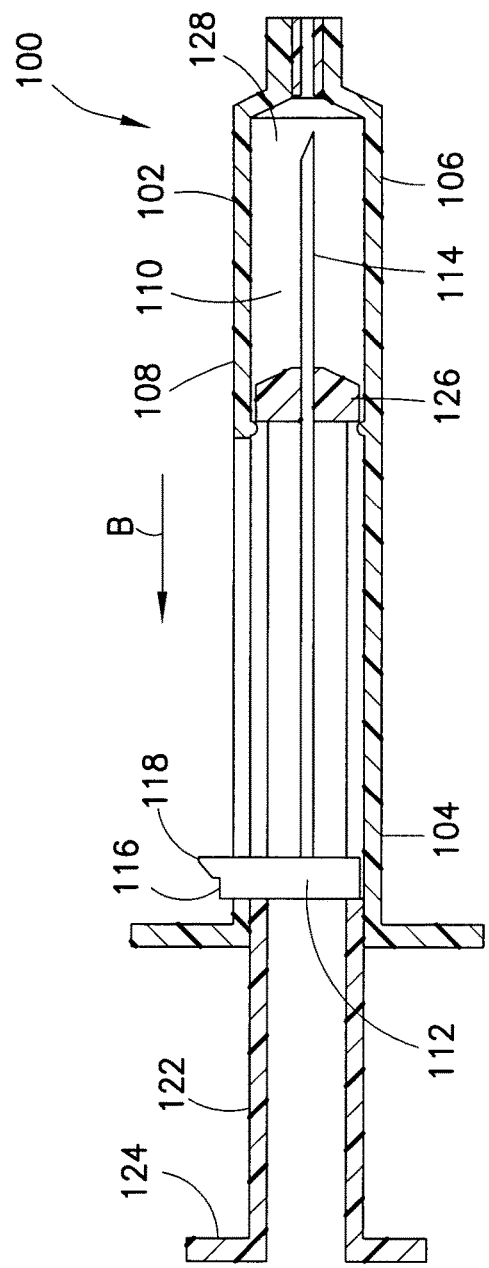
FIG. 3 is a cross-sectional side view of the syringe assembly of FIG. 1 in the retracted position in accordance with an embodiment of the present invention.
Figure 8:
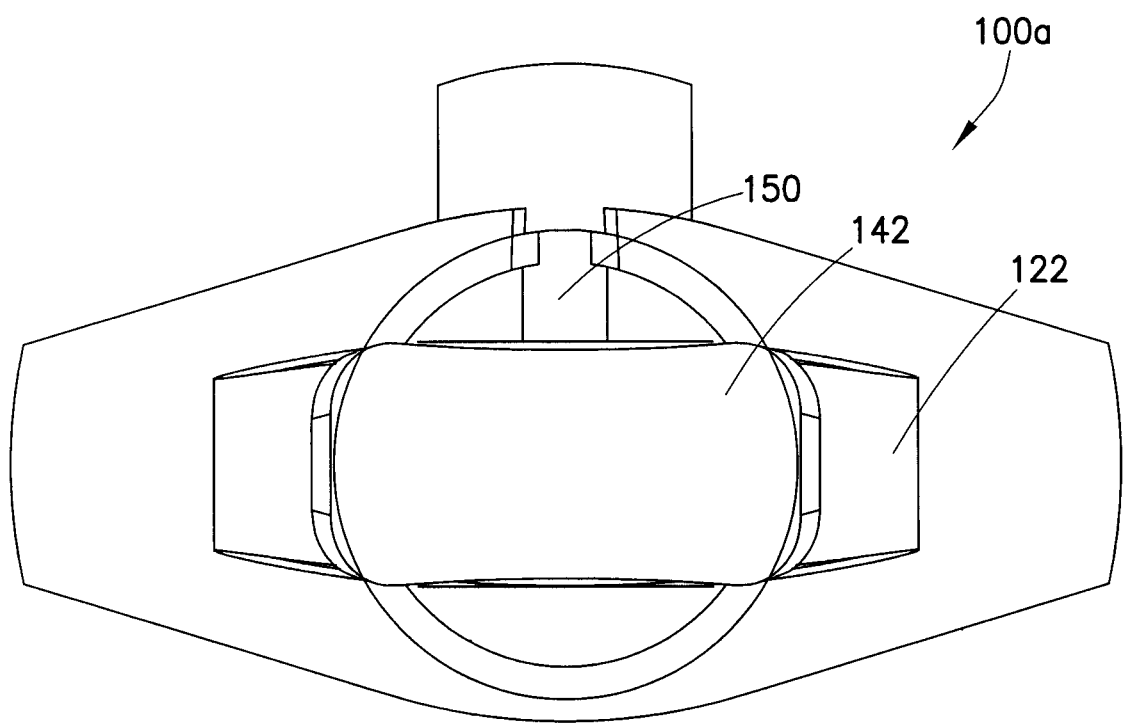
FIG. 8 is a back view of the syringe assembly of FIG. 4 in accordance with an embodiment of the present invention.
Figure 9:
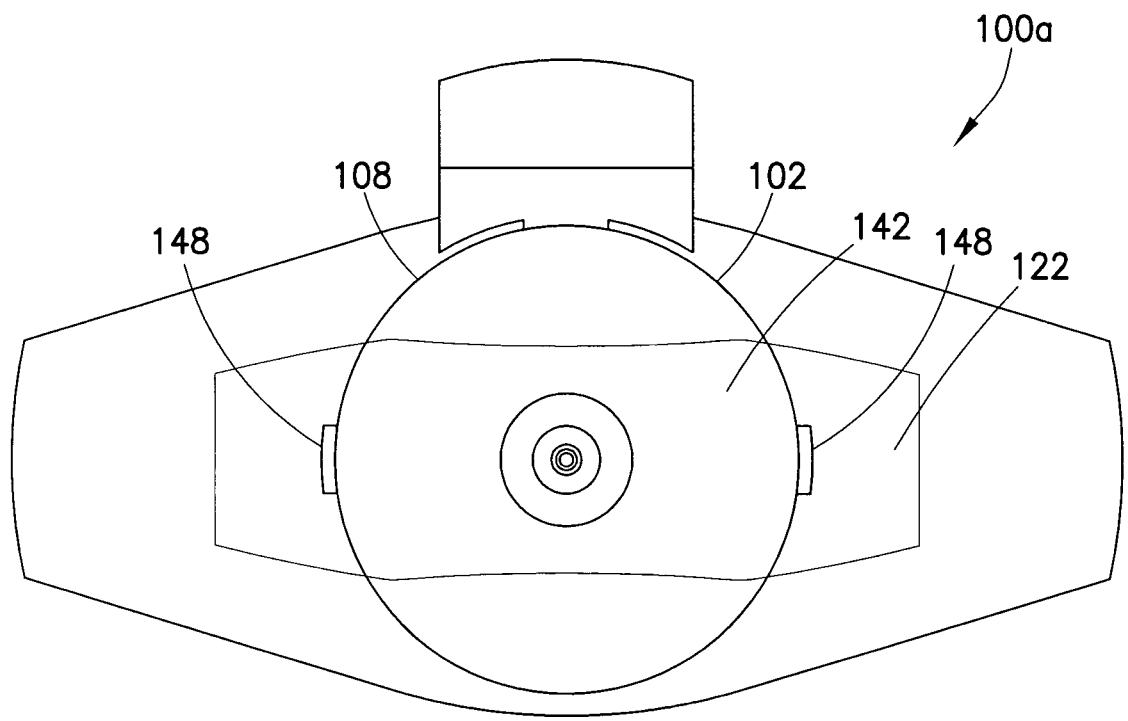
FIG. 9 is a front view of the syringe assembly of FIG. 4 in accordance with an embodiment of the present invention.

The present invention is directed to a syringe assembly, such as a hypodermic syringe, for the extraction of bodily fluids from a patient, and the subsequent transfer of the extracted fluid to a separate collection container. As shown in FIGS. 1-3, a retractable needle assembly 100 in accordance with an embodiment of the present invention includes a housing 102, such as an elongated cylindrical barrel, having a proximal end 104 and a distal end 106 and a sidewall 108 extending therebetween and defining a hollow bore 110 between the proximal end 104 and the distal end 106. A hub 112 is disposed at least partially within the hollow bore 110 and at least partially supports a needle cannula 114 extending along a longitudinal axis A of the retractable needle assembly 100.

An elongate plunger 122, having a proximal end 124 and a distal end 126, is disposed and sized to fit within the bore 110 of the housing 102 for a slidable movement therein. The plunger 122 and the sidewall 108 of the housing 102 are dimensioned to define a reservoir 128 for receiving and expelling fluids therefrom. In one embodiment, the plunger 122 includes a stopper 130 disposed at said distal end 126 to occlude an open end 132 of the reservoir 128, with the stopper 130 being sized and shaped to form a slidably substantially fluid tight seal with the bore 110 of the housing 102 for forming the reservoir 128. In an alternate embodiment, the stopper is integral to the plunger, such as through plastic stopper-seal technology.

The hub 112 is connected to a needle retraction member 116 which extends at least partially through a portion of the sidewall 108 of the housing 102 to allow a user to manually transition the needle cannula 114 from an initial position in which at least a portion of the needle cannula 114 extends from the distal end 106 of the housing 102, as shown in FIG. 1, to a retracted position in which the needle cannula 114 is fully shielded by the housing 102, as shown in FIG. 3. In certain configurations, the hub 112 and the needle retraction member 116 may be co-molded as a unitary component. In another embodiment, the hub 112 and the needle retraction member 116 may be separately formed and subsequently assembled.

In one embodiment, the needle retraction member 116 includes a tab or button 118 to allow a user to slide the needle retraction member 116 connected to the hub 112 along a groove 120 defined within the sidewall 108 of the housing 102 in the direction of the arrow B, as shown in FIG. 3, in order to retract the needle cannula 114 into the housing 102. In certain embodiments, transition of the needle cannula 114 from the retracted position to the initial position is prevented by a mechanical barrier, as will be discussed herein, in order to prevent inadvertent re-exposure of the needle cannula 114.

In use, a user of the retractable needle assembly 100 would insert the tip of the needle cannula 114 into a patient to withdraw a fluid sample, such as a blood specimen, and would pull the proximal end 124 of the plunger in the direction of arrow B, as shown in FIG. 3. A seal may be provided around the cannula 114 adjacent the distal end 106 of the housing 102 for forming a fluid tight seal within the reservoir 128 with the retractable needle assembly 100 in the initial position. As a vacuum is created in the hollow bore 110, the fluid sample from the patient is drawn into the reservoir 128. The cannula 114 may include a break, as described herein, to allow blood to enter the reservoir 128. Once the specimen draw is complete, the user slides the needle retraction member 116 in the direction of arrow B, as shown in FIG. 3, such as by sliding the button 118 along the groove 120 in the housing 102, to retract the needle cannula 114 into the housing 102. Once the needle cannula 114 is fully shielded by the housing 102, the user may push the plunger 122 in a direction opposite of arrow B, as shown in FIG. 3, to expel the collected fluid sample from the reservoir 128 into a secondary collection container (not shown). During the redeployment of the plunger 122 in order to expel the collected fluid from the reservoir 128, the hub 112 and the needle cannula 114 supported thereby, remain stationary within the bore 110 of the housing 102. In one embodiment, a lock out detent 134 restrains the needle retraction member 116 against a portion of the housing 102 to prevent the inadvertent advancement of the hub 112 and/or needle cannula 114 once transition from the initial position to the retracted position has occurred.

In accordance with another embodiment of the present invention, as shown in FIGS. 4-18, a retractable needle assembly 100a includes a housing 102 including a central longitudinal groove 136 disposed within the sidewall 108. The housing 102 may also include a pair of slide grooves 144, 146 disposed on opposing sides of the central longitudinal groove 136. The plunger 122 includes a pair of depending arms 138, 140 disposed within the housing 102 substantially on opposing sides of the longitudinal groove 136. Each of the depending arms 138, 140 may include a protrusion 148 adjacent the distal end 126 of the plunger 122 and provided within the corresponding slide grooves 144, 146 disposed within the housing 102. The plunger 122 may optionally include a user pull ring 142 adjacent the proximal end 124 of the plunger 122 to assist the user in retracting the plunger 122.

The needle retraction member 116 may include a central portion 150 disposed within the central longitudinal groove 136 of the housing 102, and opposing contact portions 152, 154 extending from the central portion 150 and engaging corresponding portions of the plunger 122 along the central longitudinal groove 136. The needle cannula 114 supported by the hub 112 includes a break 156 in the cannula 114 adjacent the distal end 106 of the housing when the retractable needle assembly 100a is in the initial position, as shown in FIG. 7. The break 156 in the cannula 114 allows for the fluid specimen collected from the patient to flow into the reservoir 128 defined between the stopper 130 of the plunger 122 and the sidewall 108 of the housing 102.

In use, the tip of the needle cannula 114 penetrates the skin of a patient while the retractable needle assembly 100a is in the initial position, as shown in FIGS. 4-9. Once the needle cannula 114 has accessed a fluid specimen of a patient, the user will retract the plunger 122 such as by pulling the pull ring 142 in the direction of arrow C, as shown in FIG. 10, to transition the retractable needle assembly 100a to the specimen draw position, as shown in FIGS. 10-12. During this phase, as the user advances the plunger 122 in the direction of arrow C, as shown in FIG. 10, each of the depending arms 138, 140 slide within the slide grooves 144, 146 of the housing, creating a vacuum in the reservoir 128 which draws the fluid sample from the patient into the reservoir 128. Fluid from the patient enters the reservoir 128 via the needle break 156 adjacent the distal end 106 of the housing 102 when the retractable needle assembly 100a is in the specimen draw position. When the protrusions 148 of the depending arms 138, 140 contact the proximal end of the corresponding slide grooves 144, 146, the plunger has been advanced to the maximum draw position.

Figure 14:
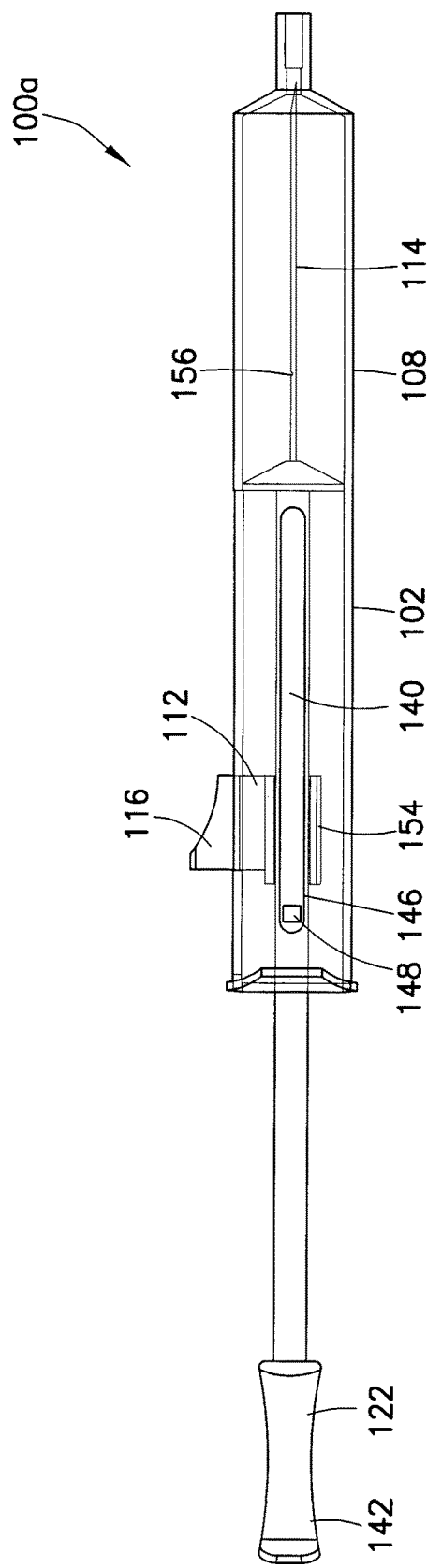
FIG. 14 is a side view of the syringe assembly of FIG. 13 in accordance with an embodiment of the present invention.
Figure 15:
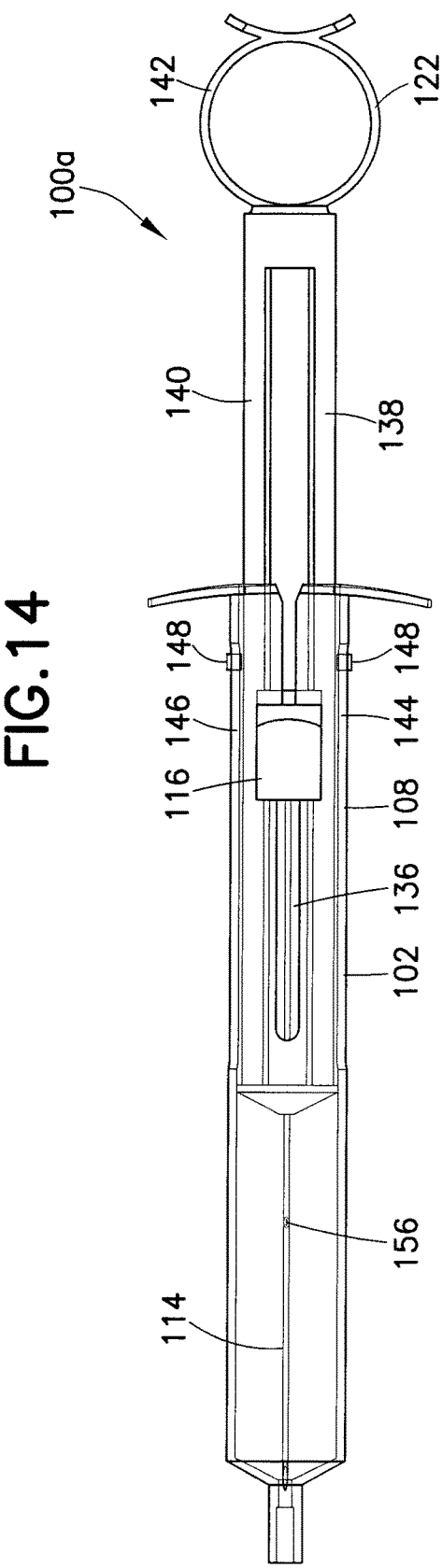
FIG. 15 is a top view of the syringe assembly of FIG. 13 in accordance with an embodiment of the present invention.

At this time, the user will transition the needle retraction member 116 to the retracted position, as shown in FIGS. 13-15, in which the needle cannula 114, connected to the needle retraction member 116 and hub 112, is fully shielded by the housing 102. In one embodiment, the user will slide the needle retraction member 116 along the longitudinal groove 136 of the housing in the direction of arrow D, as shown in FIG. 13, to transition the needle retraction member 116 to the retracted position. During this transition, the contact portions 152, 154 extending from the central portion 150 of the needle retraction member 116 slide along the corresponding portions of the plunger 122 extending along the longitudinal groove 136 until the needle retraction member 116 abuts the portion of the housing 102 surrounding the termination of the longitudinal groove adjacent the proximal end 104 of the housing 102. Optionally, the needle retraction member 116 may include a detent to allow for one-way snap engagement with the longitudinal groove 136 during assembly.

Figure 18:
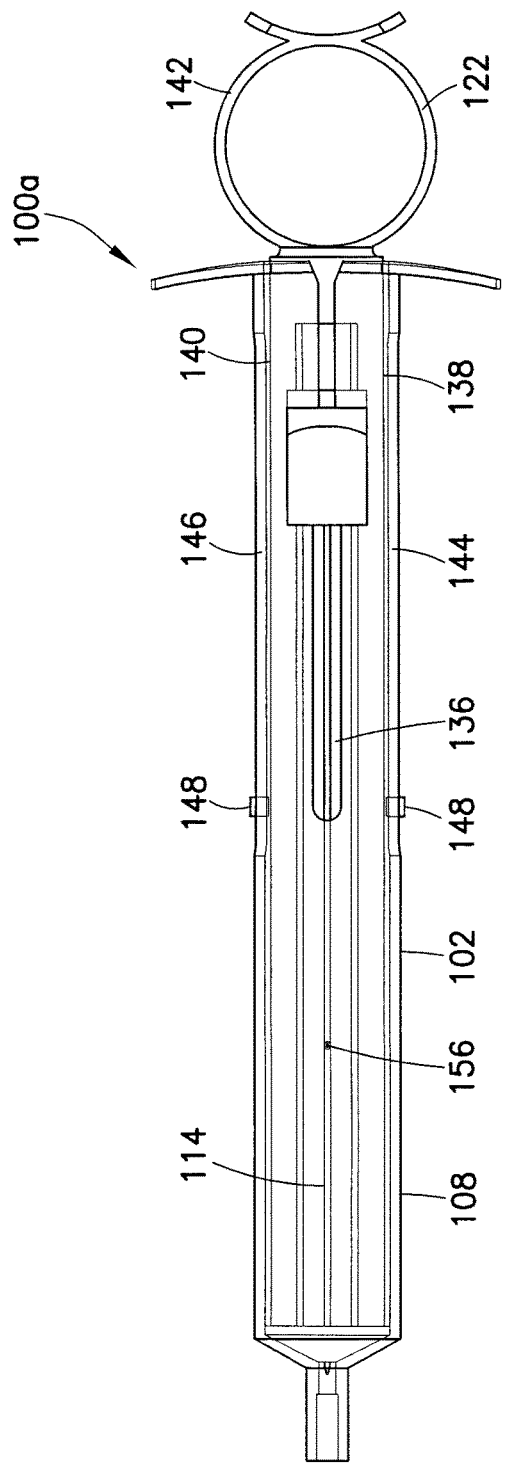
FIG. 18 is a top view of the syringe assembly of FIG. 16 in accordance with an embodiment of the present invention.
Figure 19:
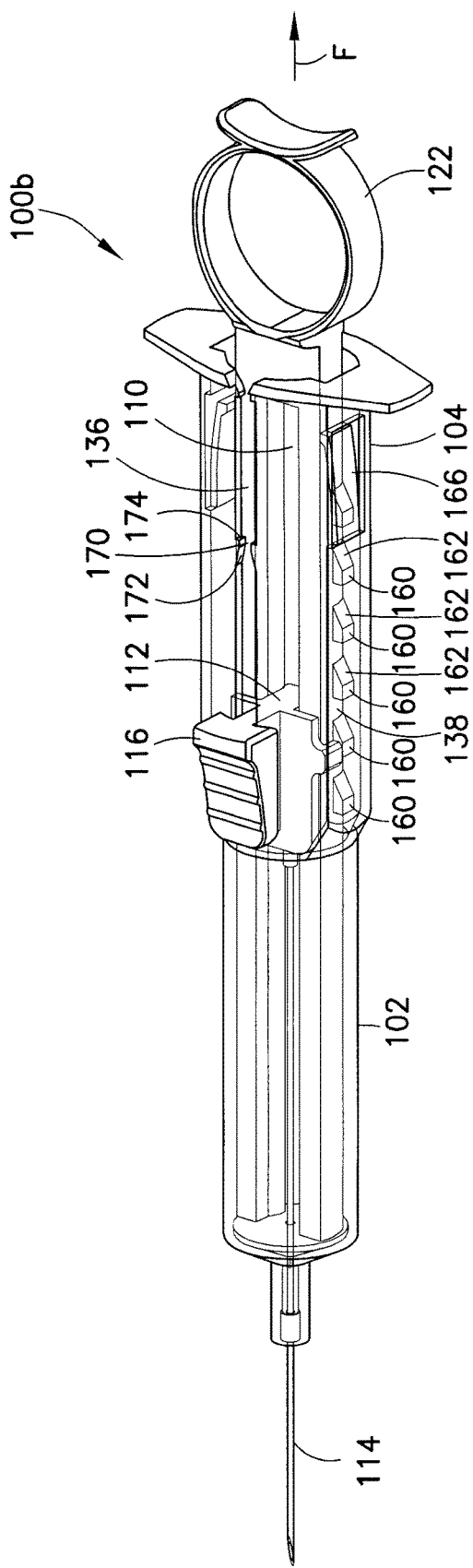
FIG. 19 is a perspective view of a syringe assembly in an initial position in accordance with an embodiment of the present invention.
Figure 20:
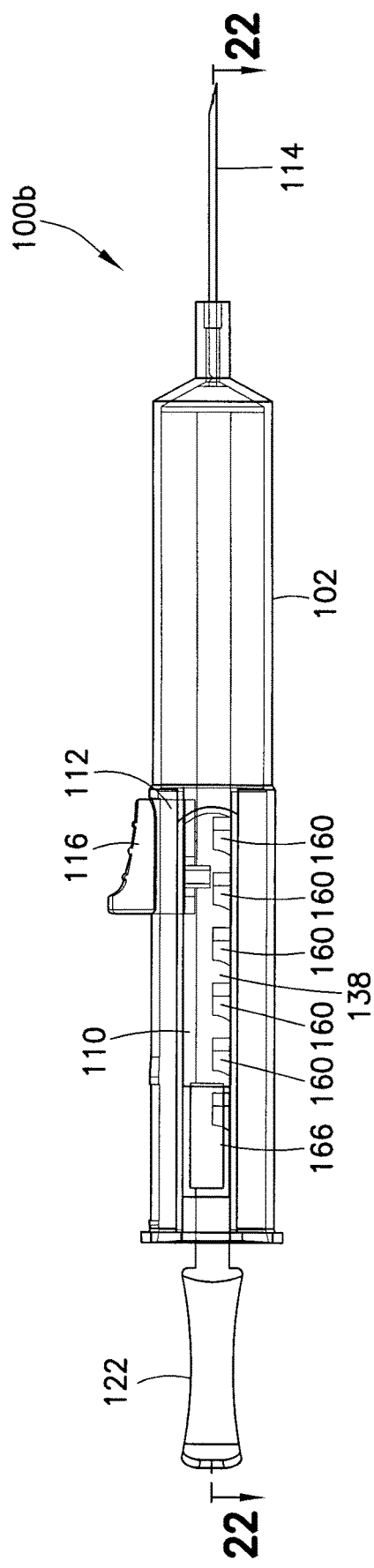
FIG. 20 is a side view of the syringe assembly of FIG. 19 in accordance with an embodiment of the present invention.
Figure 21:
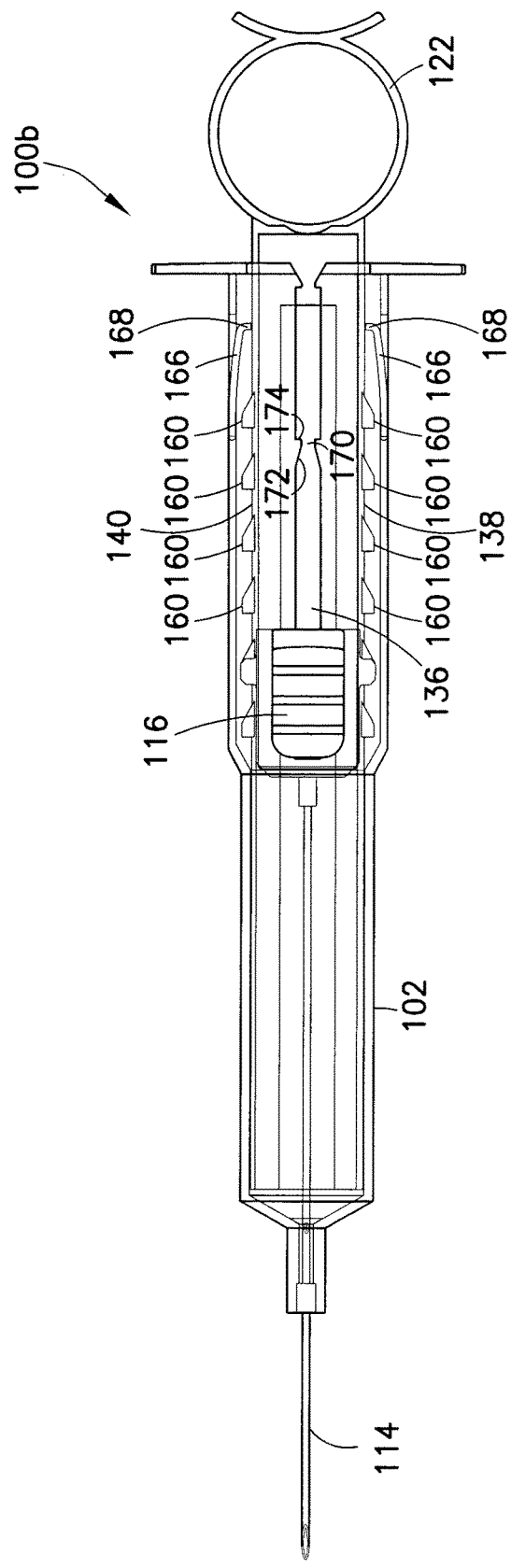
FIG. 21 is a top view of the syringe assembly of FIG. 19 in accordance with an embodiment of the present invention.
Figure 24:
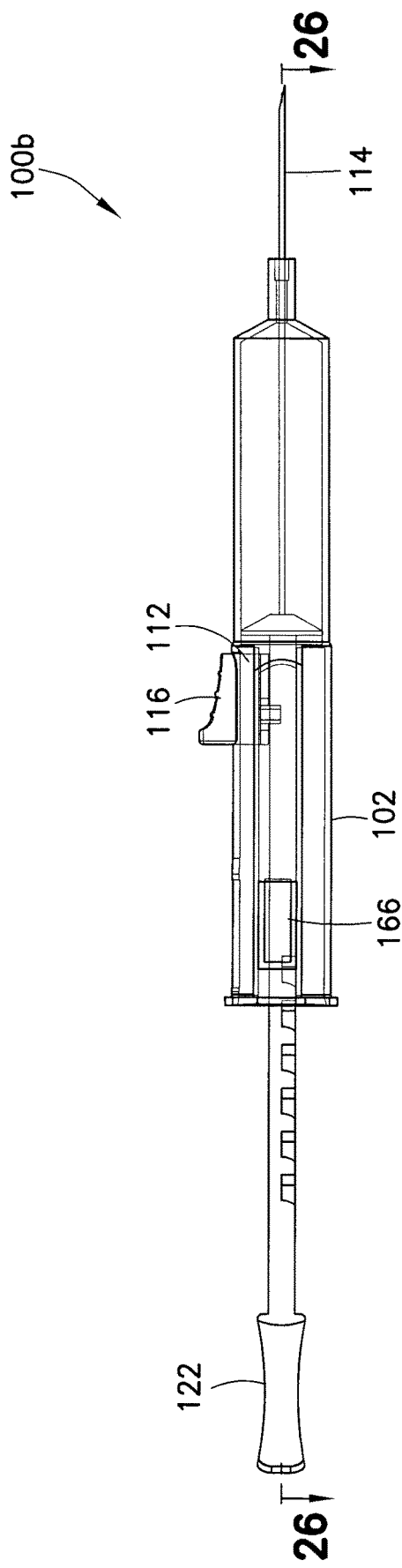
FIG. 24 is a side view of the syringe assembly of FIG. 23 in accordance with an embodiment of the present invention.

Once the retractable needle assembly 100a has been transitioned to the retracted position, the user may redeploy the plunger 122 in the direction of arrow E, as shown in FIG. 16, to expel the fluid specimen collected within the reservoir 128 during the specimen transfer position, as shown in FIGS. 16-18. During the specimen transfer, the user will advance the plunger 122 in the direction of arrow E, as shown in FIG. 16, and advance the depending arms 138, 140 along the slide grooves 144, 146 in the opposite direction from the specimen draw. As the plunger is redeployed, the stopper 130 is advanced in the distal direction and expels the collected specimen from within the reservoir 128 through an opening 158 vacated by the tip of the needle cannula 114. In certain configurations, the opening 158 may include a hydrophobic material to prevent the inadvertent escape of fluid specimen until a sufficient compressive force is applied to the reservoir 128 by the advancement of the plunger 122 in the distal direction during specimen transfer. It is noted herein that the use of hydrophobic material in the opening 158 must be carefully employed to balance the prevention of fluid from inadvertently escaping from the reservoir 128 with the desire for full specimen transfer during the specimen transfer phase. During the specimen transfer, the contents of the reservoir 128 may be expelled from the retractable needle assembly 100a into a separate collection container (not shown). During specimen transfer, the hub 112, needle cannula 114, and needle retraction member 116 remain stationary in the retracted position.

In accordance with another embodiment of the present invention, a retractable needle assembly 100b, as shown in FIGS. 19-34, includes a housing 102, a plunger 122, a needle cannula 114, a hub 112, and a needle retraction member 116 as described above with reference to the previous figures. In this configuration, each of the depending arms 138, 140 of the plunger 122 include a plurality of ramped stops 160 including a slanted proximal surface 162 and a vertical distal surface 164, as clearly shown in FIG. 22. It is contemplated herein that the vertical distal surface 164 may not be entirely vertical and may have a slight angle of several degrees to assist in a smooth retraction of the plunger 122 from the housing 102. Also in this configuration, the proximal end 104 of the housing 102 includes a pair of restraints 166 positioned on opposing sides of the longitudinal groove 136. Each of the restraints 166 includes a protrusion 168 extending into a portion of the hollow bore 110 of the housing 102. In certain configurations, each of the restraints 166 may have an inwardly directed spring bias causing the protrusions 168 to be directed further into the hollow bore 110 of the housing 102 in the at rest condition.

Also in accordance with this embodiment, the longitudinal groove 136 defined within the housing 102 may include a gap region 170 having a narrowed diameter. In one configuration, the surfaces of the housing 102 adjacent the gap region 170 may include a slanted distal surface 172 and a vertical proximal surface 174. In a further configuration, the gap region 170 may be provided toward the proximal end of the longitudinal groove 136.

Figure 25:
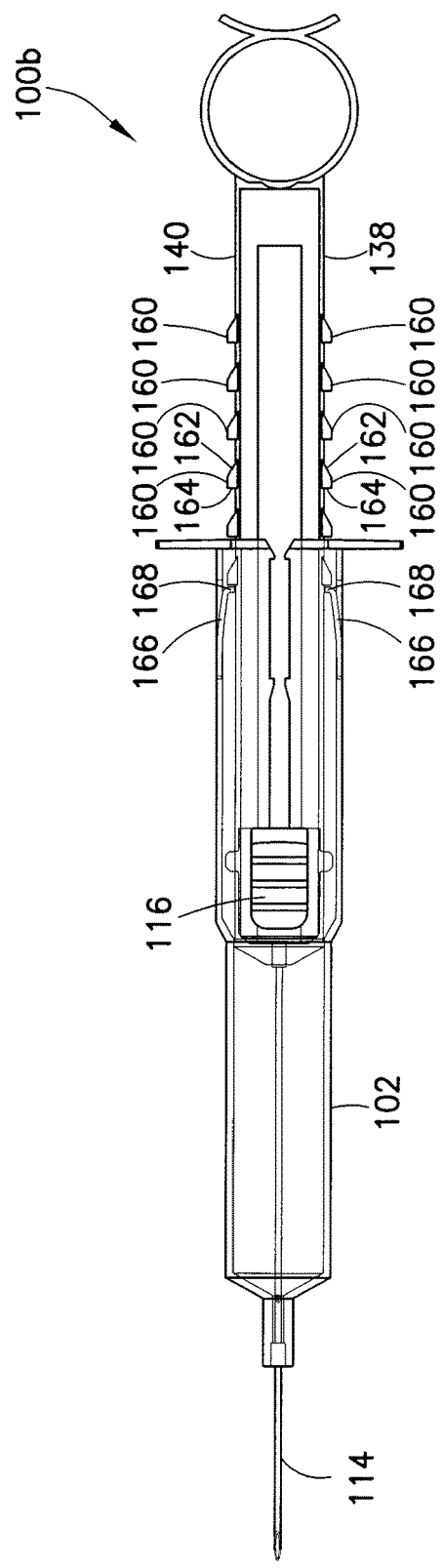
FIG. 25 is a top view of the syringe assembly of FIG. 23 in accordance with an embodiment of the present invention.
Figure 28:
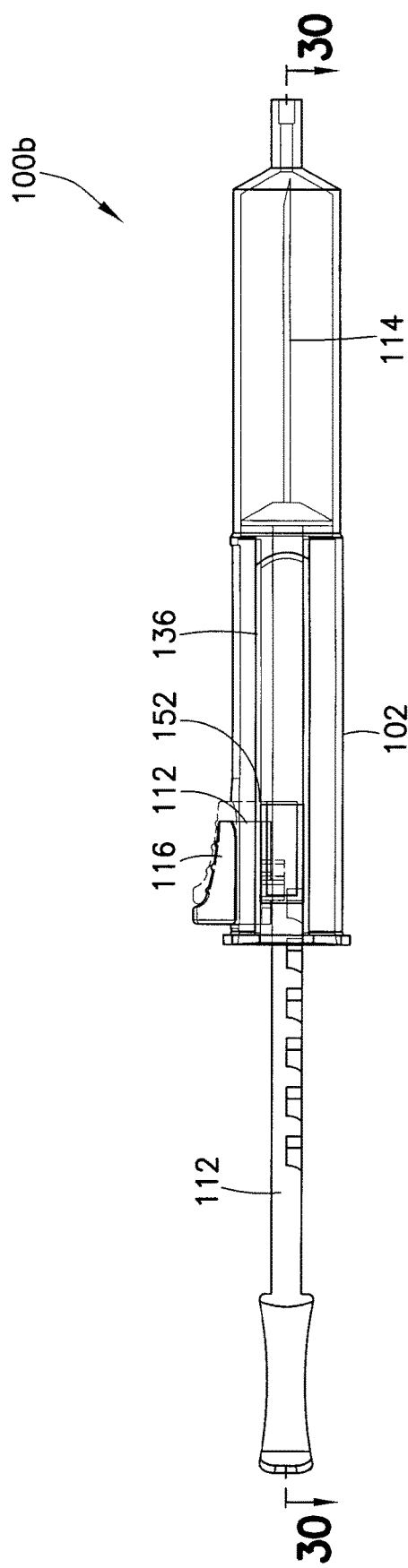
FIG. 28 is a side view of the syringe assembly of FIG. 27 in accordance with an embodiment of the present invention.

In use, the user transitions the retractable needle assembly 100b as described above, with reference to the previous figures, from the initial position, as shown in FIGS. 19-22, to the specimen draw position, as shown in FIGS. 23-26. During this transition, the plunger 122 is pulled in the proximal direction, as shown by arrow F of FIG. 19, and fluid specimen is collected within the reservoir 128 of the housing 102, through the break, as discussed above. As the plunger is advanced proximally, the ramped stops 160 of each of the depending arms 138, 140 are advanced past the restraints 166 formed integrally with the housing 102. As the ramped stop 160 is directed toward the restraint 166, the slanted proximal surface 162 of the ramped stop 160 allows the protrusion 168 of the restraint 166 to be deflected out of the path of the depending arms 138, 140, allowing the plunger to be advanced proximally in the direction of arrow F of FIG. 19. As shown in FIGS. 23 and 25-26, once the plunger 122 is fully extended to the maximum draw, the most distally positioned ramped stop 160 abuts the protrusion 168. In this configuration, the vertical distal surface 164 of the ramped stop 160 contacts the protrusion 168 and prevents movement of the plunger 122 in the distal direction. It is noted herein that even in the orientation of a partial specimen draw in which the plunger 122 is only partially withdrawn from the housing 102, the plunger 122 is still locked-out by the restraints 166 until the cannula 114 is retracted.

Once the plunger has been transitioned to the maximum specimen draw position, as shown in FIGS. 23-26, the user may transition the needle retraction member 116 from the initial position, as shown in FIGS. 19-26, to the retracted position, as shown in FIGS. 27-30. During this transition, the needle retraction member 116 is advanced along the longitudinal groove 136 and through the gap region 170 in order to retract the needle cannula 114 into the hollow bore 110 of the housing 102. As the needle retraction member 116 is advanced through the gap region 170, the contact portions 152, 154 of the needle retraction member 116 contact the slanted distal surface 172 (shown in FIG. 19) of the housing 102 adjacent the gap region 170 and cam thereagainst, allowing the needle retraction member 116 to pass through the gap region 170. Once the needle retraction member 116 has passed through the gap region 170, the contact portions 152, 154 abut the vertical proximal surface 174 of the housing 102 adjacent the gap region 170 preventing the redeployment of the needle retraction member 116 once the transition from the initial position to the retracted position has occurred.

Figure 29:
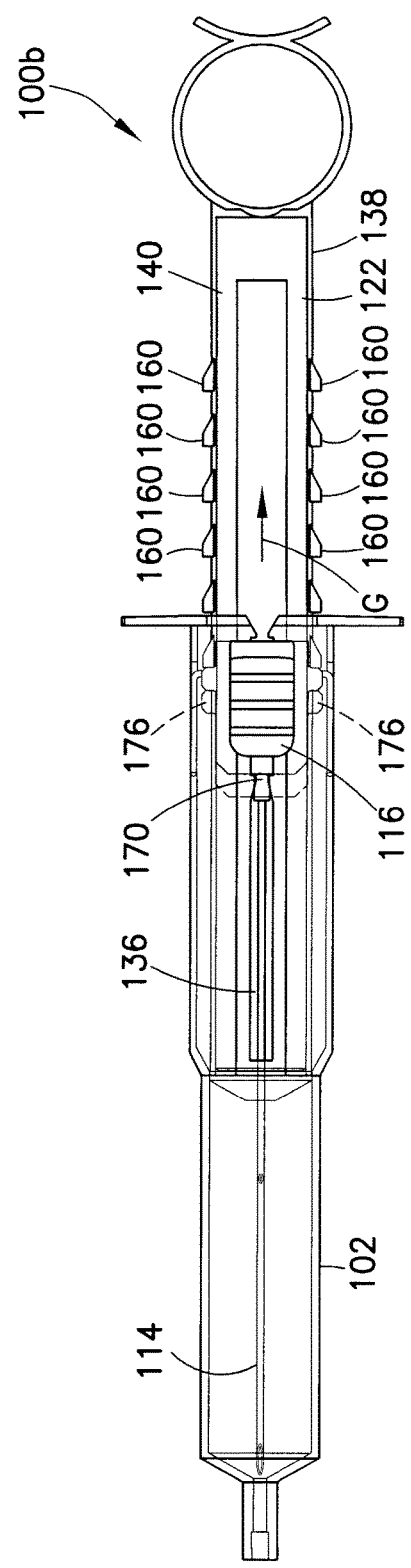
FIG. 29 is a top view of the syringe assembly of FIG. 27 in accordance with an embodiment of the present invention.
Figure 30:
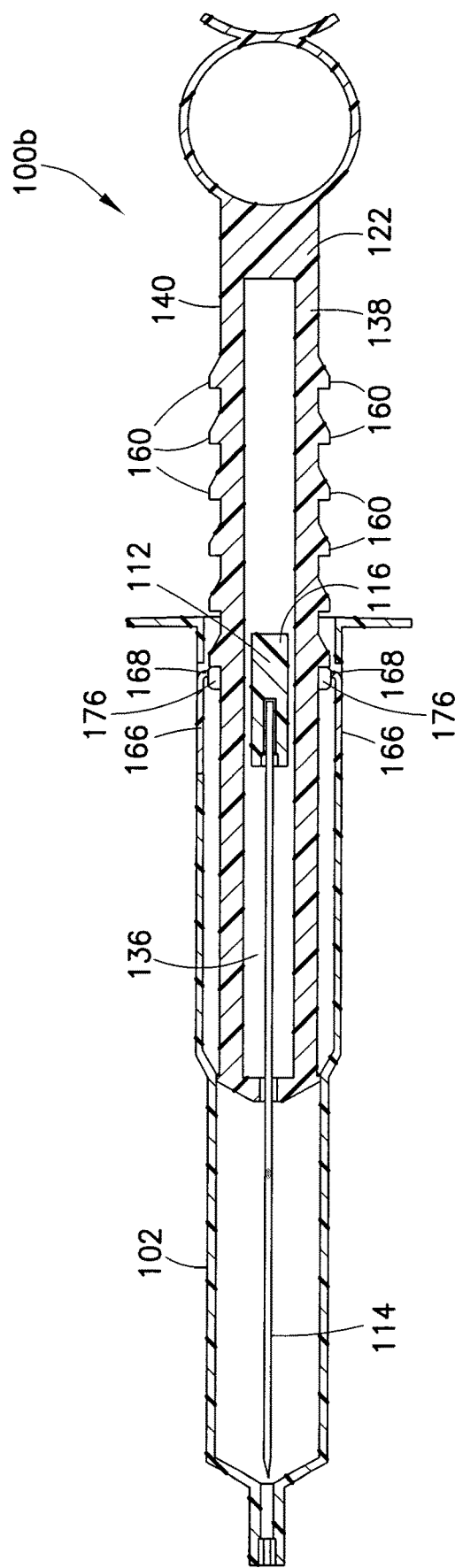
FIG. 30 is a cross-sectional view of the syringe assembly of FIG. 27 taken along line 30-30 of FIG. 28 in accordance with an embodiment of the present invention.
Figure 31:
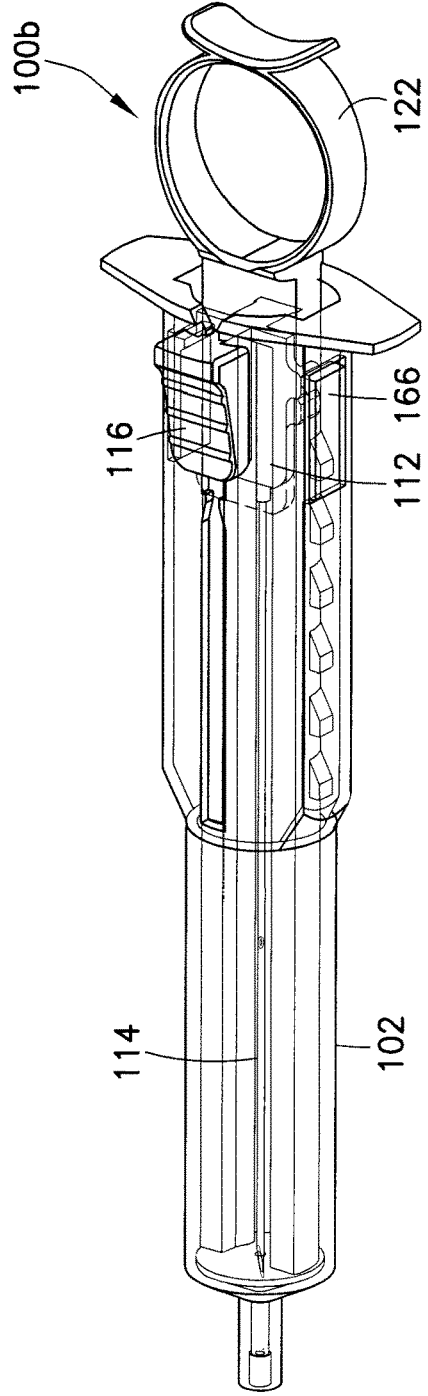
FIG. 31 is a perspective view of the syringe assembly of FIG. 27 having the plunger redeployed within the body of the syringe in accordance with an embodiment of the present invention.
Figure 32:
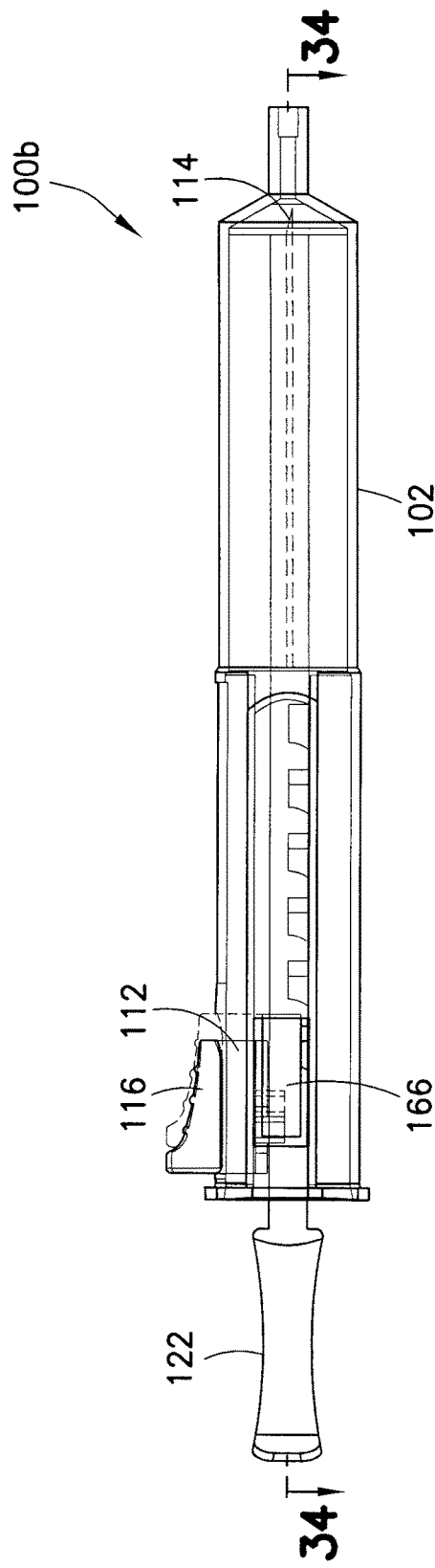
FIG. 32 is a side view of the syringe assembly of FIG. 31 in accordance with an embodiment of the present invention.
Figure 33:
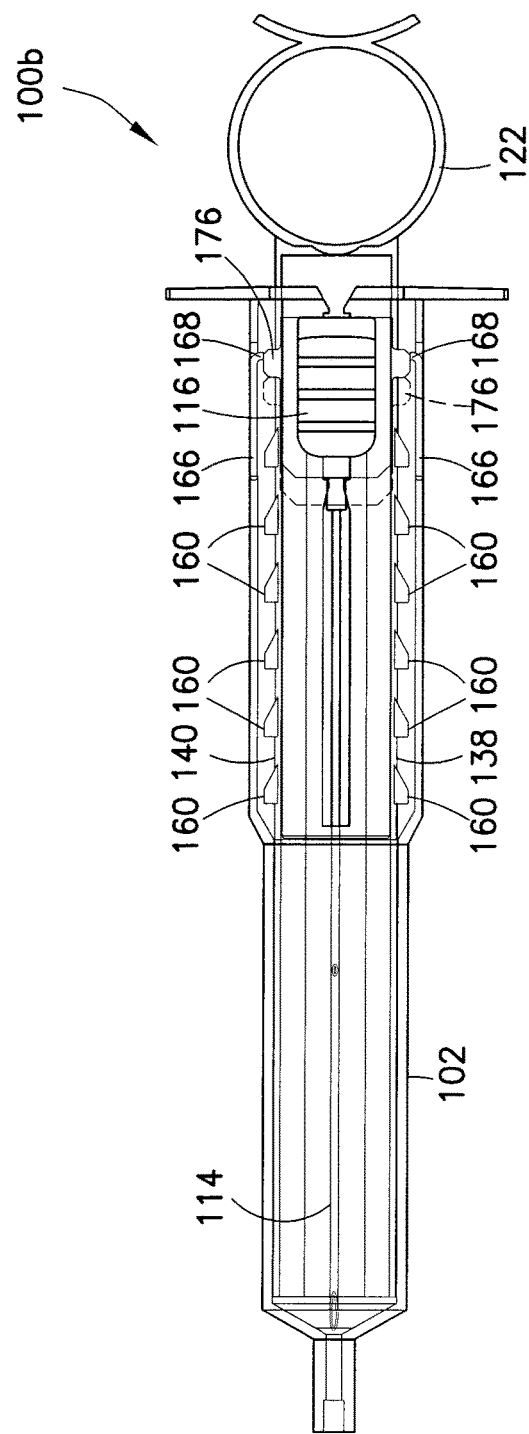
FIG. 33 is a top view of the syringe assembly of FIG. 31 in accordance with an embodiment of the present invention.

As shown specifically in FIGS. 29-30, the needle retraction member 116 may also include a pair of flanges 176 disposed on opposing sides and oriented in line with the ramped stops 160 of the depending arms 138, 140 of the plunger 122. As the needle retraction member 116 is advanced in the proximal direction as shown by arrow G of FIG. 29, the flanges 176 of the needle retraction member 116 contact the protrusions 168 of the restraints 166 pushing the restraints 166 in an outwardly direction. The contact of the flanges against the bias of the protrusions 168 of the restraints 166 opens the pathway for the plunger 122 (as shown in FIG. 33) to be redeployed into the housing to expel the collected specimen from the reservoir in the specimen dispensing position, as shown in FIGS. 31-34, and described above.

In accordance with a further embodiment of the present invention, as shown in FIGS. 35-39, a retractable needle assembly 100c may include an elastomeric plug 178 disposed about the needle cannula 114. In this configuration, the housing 102 may also include an inner barrel 180 ultrasonically welded to an outer barrel 182. In certain configurations, the inner barrel 180 and the outer barrel 182 may be co-formed as a unitary component. Fitted within the inner barrel 180 is a chamber extender 184 which abuts the elastomeric plug 178. The inner barrel 180 of the housing 102 may define a break 186 adjacent the distal end, allowing the proximal end of the cannula 114 and a portion of the elastomeric plug 178 to form a fluid pathway into the reservoir 128 of the hollow bore 110 to allow fluid specimen to enter the reservoir 128.

FIGS. 36-39 illustrate the transition of the retractable needle assembly 100c from the initial position, shown in FIG. 36, to the specimen draw position, shown in FIG. 37, to the retracted position, shown in FIG. 38, to the specimen dispensing position, shown in FIG. 39. As can be seen in FIGS. 36-39, the configuration of the housing 102 to include an inner barrel 180 and an outer barrel 182 with a chamber extender 184 disposed within the inner barrel 180 allows for the transition of the retractable needle assembly 100c as described above, but allows for the cannula 114 to be considerably shorter. In this embodiment, the needle retraction member (as discussed above) may be connected to the chamber extender 184 rather than to the cannula 114 itself.

As shown in FIG. 38, the placement of the break 186 adjacent the distal end of the housing 102 eliminates or greatly reduces the issue of backflow of fluid specimen through the break 186 when the plunger 122 is advanced in the distal direction to expel the collected fluid 188 from the reservoir 128.

In accordance with still a further embodiment of the present invention, as shown in FIGS. 40-45, a retractable needle assembly 100d includes a flash feature by which a user can determine whether a suitable vein has been accessed by the tip of the cannula 114 by the presence of a small amount of blood in the distal end of the housing 102 at a flash chamber 190, as shown in FIG. 43. In this configuration, an elastomeric plug 178, such as molded TPE, is provided about the distal tip of the housing 102. As shown in the initial position in FIG. 40 (in which the housing 102 includes a frustoconical portion about the stopper 130 of the plunger 122) and in FIG. 42 (in which the housing 102 includes a truncated portion about the stopper 130 of the plunger 122), the shortened cannula 114 and the chamber extender 184 form a flash chamber 190 therearound, allowing fluid to be drawn into the cannula 114, through the break 186, and into the flash chamber 190. As shown in FIG. 43, due to the small volumetric dimensioning of the flash chamber 190, the presence of even a minute amount of fluid specimen 188, such as blood, allows the user to immediately detect proper access of the cannula 114 when the plunger is transitioned to the specimen draw position. Referring again to FIG. 43, the flash chamber 190 communicates with the reservoir 128 such that fluid 188 flowing into the cannula 114 and through the break 186 ultimately fills the reservoir 128 as described above.

Figure 41:
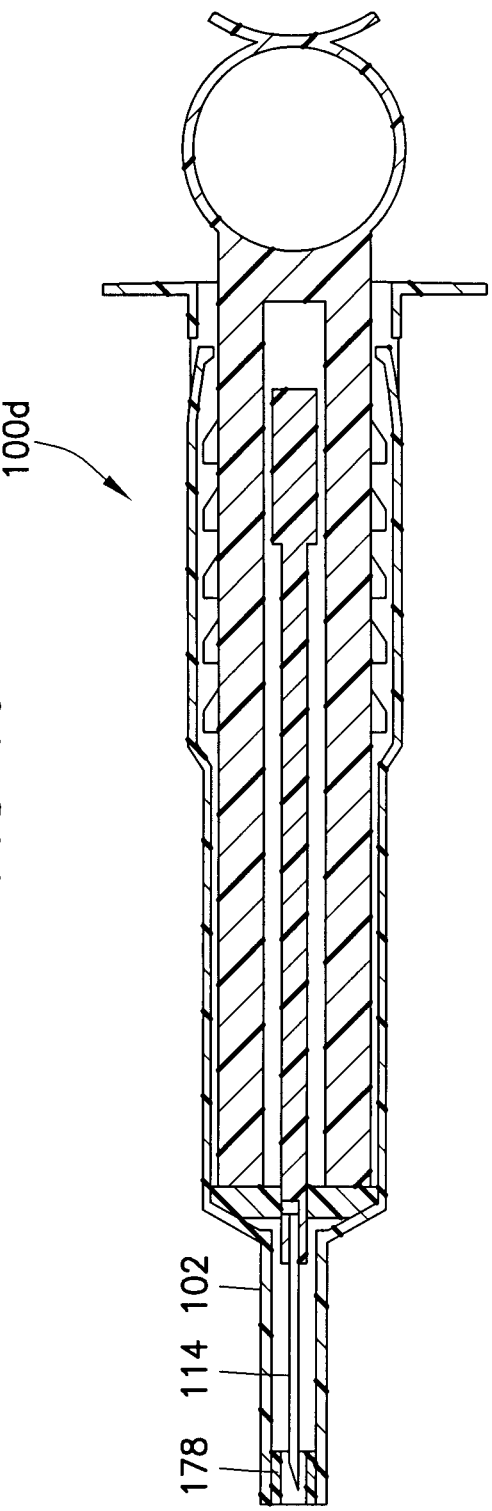
FIG. 41 is a cross-sectional top view of the syringe assembly of FIG. 40 having the plunger redeployed within the syringe barrel in accordance with an embodiment of the present invention.
Figure 44:
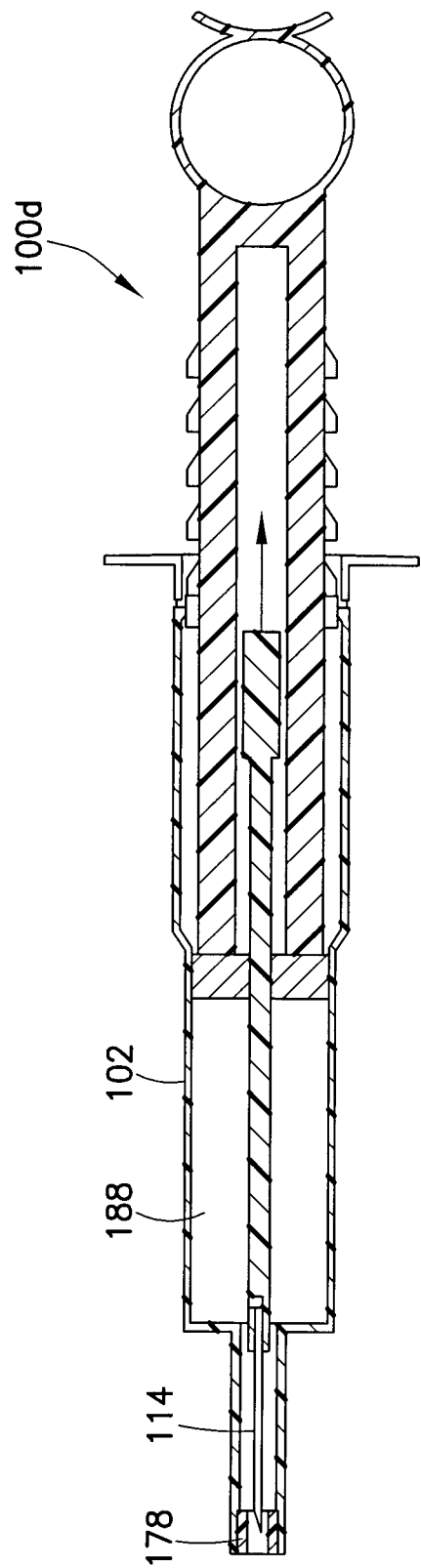
FIG. 44 is a cross-sectional top view of the syringe assembly of FIG. 40 having the needle retraction member in the retracted position in accordance with an embodiment of the present invention.
Figure 45:
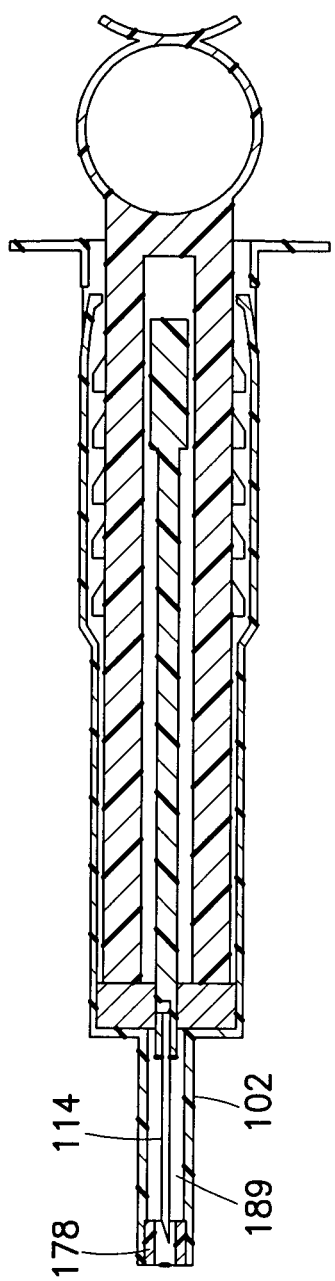
FIG. 45 is a cross-sectional top view of the syringe assembly of FIG. 40 having the plunger redeployed within the syringe barrel in accordance with an embodiment of the present invention.
Figure 46:
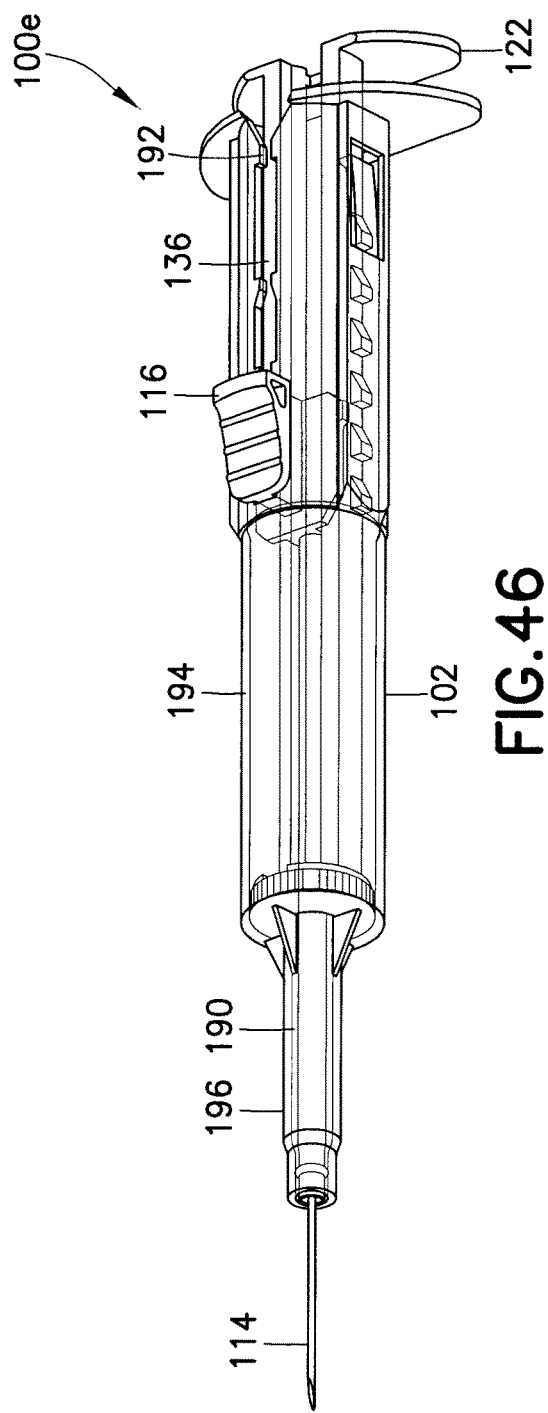
FIG. 46 is a perspective view of a syringe assembly in an initial position in accordance with an embodiment of the present invention.
Figure 47:
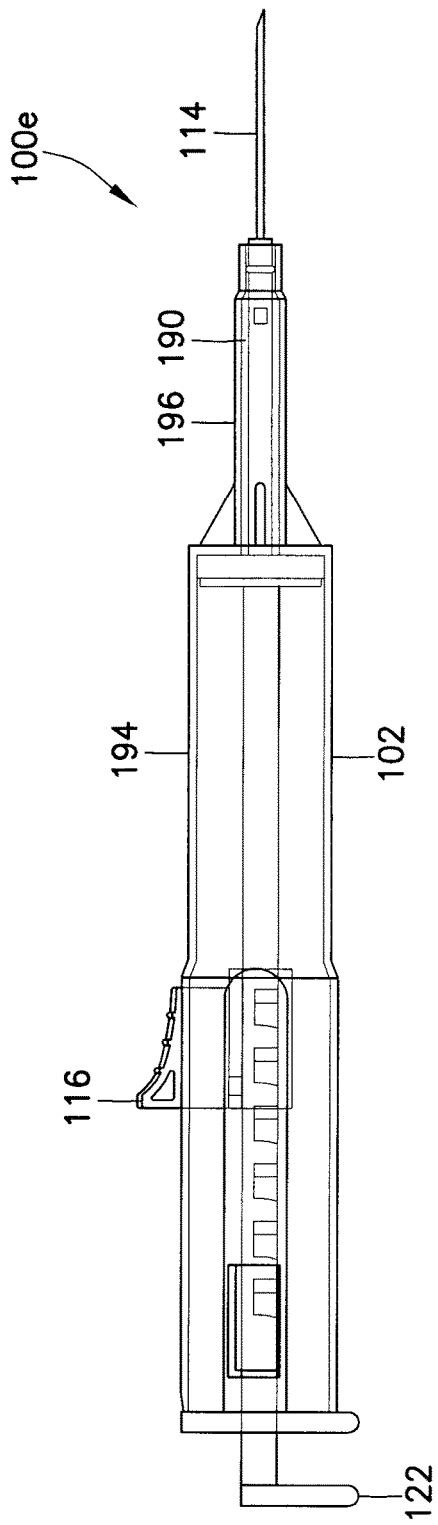
FIG. 47 is a side view of the syringe assembly of FIG. 46 in accordance with an embodiment of the present invention.
Figure 52:
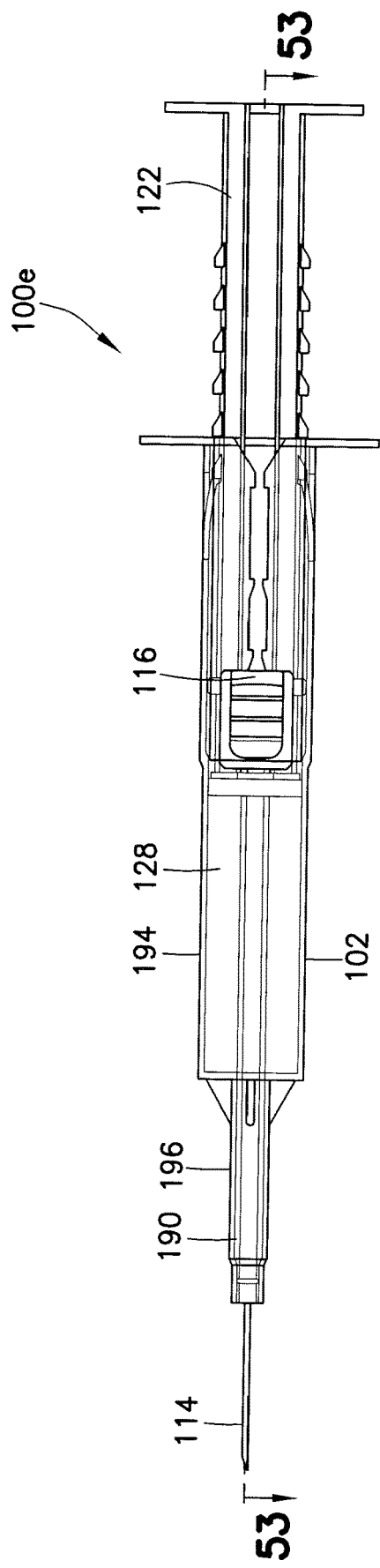
FIG. 52 is a top view of the syringe assembly of FIG. 50 in accordance with an embodiment of the present invention.
Figure 53:
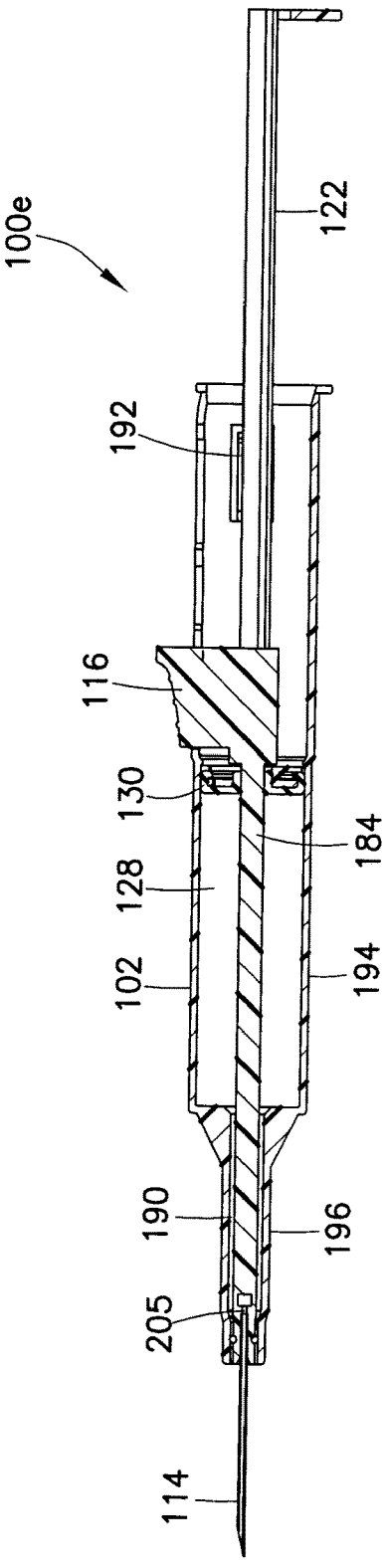
FIG. 53 is a cross-sectional view of the syringe assembly of FIG. 50 taken along line 53-53 of FIG. 52 in accordance with an embodiment of the present invention.
Figure 54:
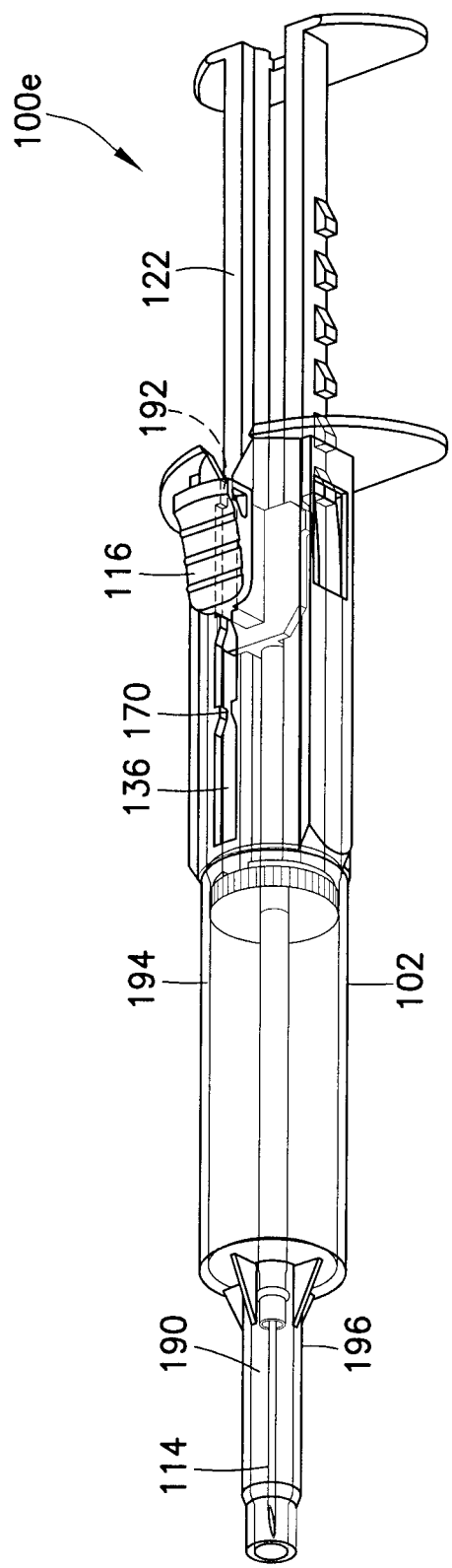
FIG. 54 is a perspective view of a syringe assembly having the needle retraction member in the retracted position in accordance with an embodiment of the present invention.
Figure 55:
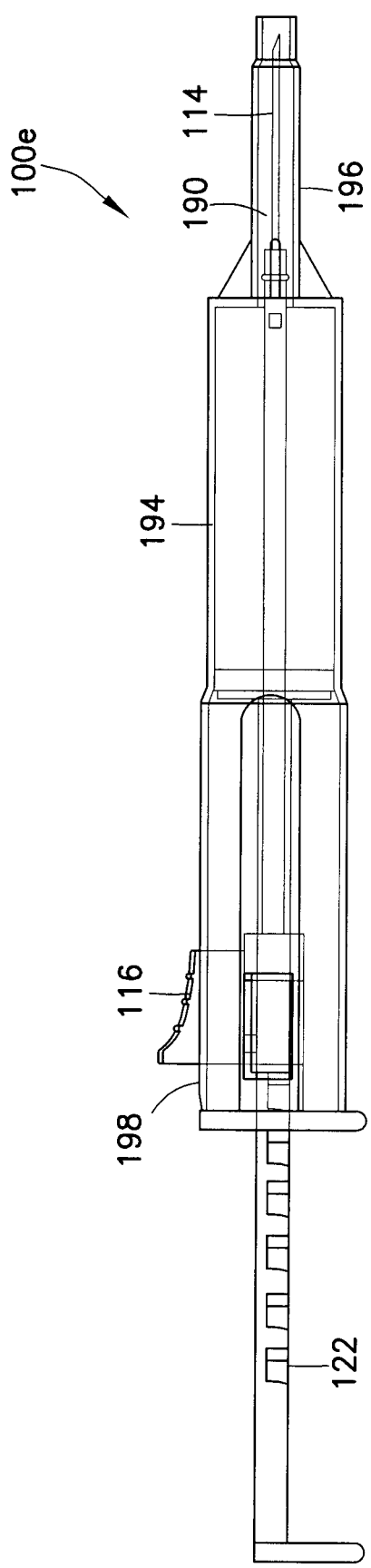
FIG. 55 is a side view of the syringe assembly of FIG. 54 in accordance with an embodiment of the present invention.
Figure 60:
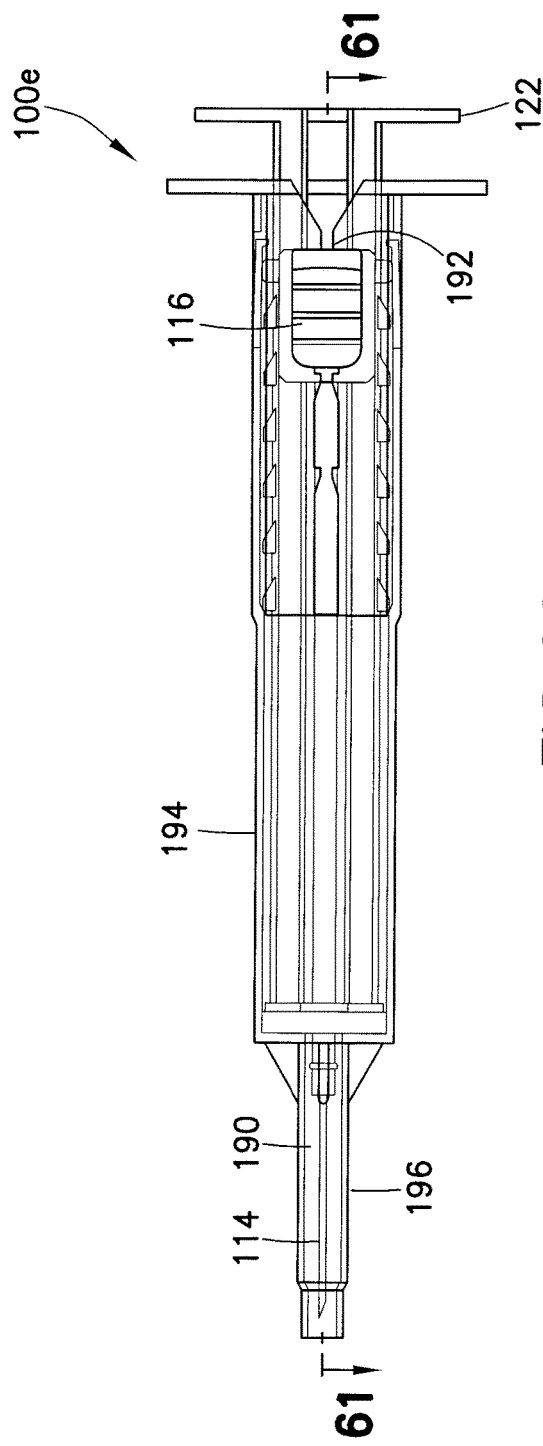
FIG. 60 is a top view of the syringe assembly of FIG. 58 in accordance with an embodiment of the present invention.
Figure 61:
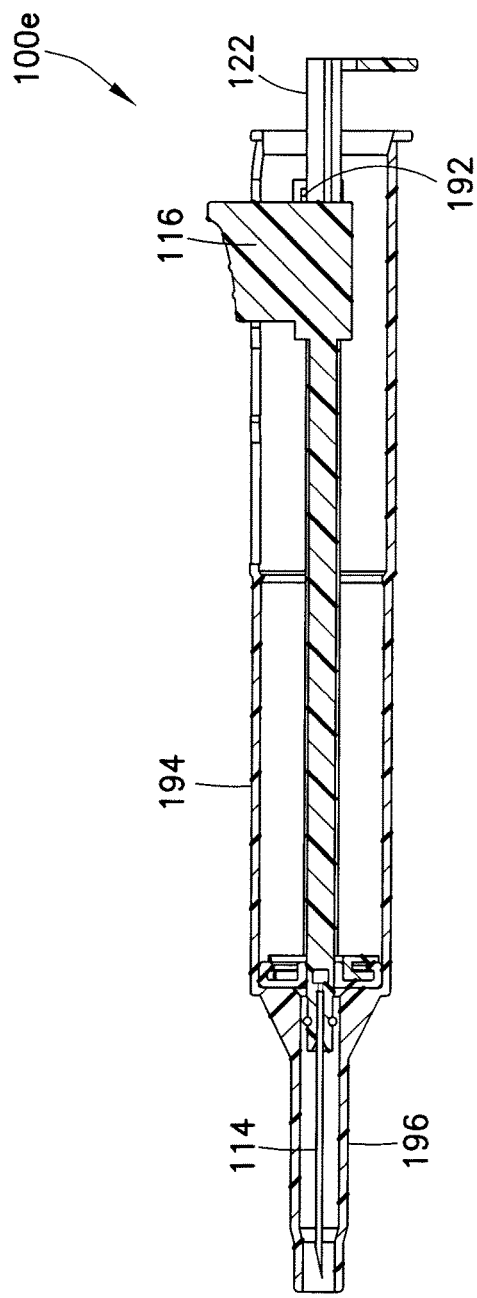
FIG. 61 is a cross-sectional view of the syringe assembly of FIG. 58 taken along line 61-61 of FIG. 60 in accordance with an embodiment of the present invention.

As shown in FIG. 44, transition of the retractable needle assembly 100d to the retracted position, in which the cannula 114 is fully surrounded by the housing 102, and the subsequent transition to the specimen dispensing position, as shown in FIGS. 41 and 45, occurs as described above with reference to the previous figures. In this configuration, backflow of specimen through the break in the cannula is substantially eliminated when the plunger is advanced.

A further embodiment of the present invention is shown in FIGS. 46-61 in which the retractable needle assembly 100e includes a different geometry to the longitudinal groove 136. In this configuration, the longitudinal groove 136 includes a detent snap 192 for restraining the needle retraction member 116 from exiting the proximal end of the housing 102 while allowing for easier assembly of the plunger 122 within the housing 102 prior to use. Similar to the embodiments described above, FIGS. 46-49 illustrate the retractable needle assembly 100e in the initial position in which the cannula 114 extends from the housing 102 and the plunger 122 is fully provided within the housing 102. The housing 102 includes a base portion 194 having the longitudinal groove 136 defined therein, and a flash portion 196 connected to the base portion 194 in which the flash chamber 190 is visible therethrough.

FIGS. 50-53 illustrate the retractable needle assembly 100e in the specimen draw position in which the plunger 122 has been withdrawn from the housing 102. In one configuration, a fluid tight seal may be provided about the stopper 130 between the plunger 122 and the housing 102, as will be discussed herein. As fluid specimen 188 is introduced into the cannula 114, it passes into the flash chamber 190 and subsequently into the reservoir 128, as discussed above. In this embodiment, there is no break in the cannula, but rather, a hole 205 defined in the hub to allow passage of fluid from the cannula into the reservoir. FIGS. 54-57 illustrate the retractable needle assembly 100e in the retracted position in which the needle cannula 114 is fully shielded by the housing 102. In this configuration, the needle retraction member 116 advances through the gap region 170, as described above, and engages the detent snap 192 so as to further restrain the needle retraction member 116 in the retracted position. An additional detent may be provided to prevent the cannula 114 from advancing in the distal direction. FIGS. 58-61 illustrate the retractable needle assembly 100e in the specimen expelling position in which the plunger 122 is redeployed into the housing 102 to expel the liquid from the reservoir 128. During the transition of the plunger 122, the needle retraction member 116 remains engaged with the detent snap 192 and restrained in a location that is proximal to the gap region 170. In certain configurations, the nose of the housing 102 may be stepped and the body of the housing 102 may also be stepped to allow for clearance during assembly, and also to allow clearance of the seal at the distal end 106 of the housing 102 during use.

In accordance with another embodiment of the present invention, the retractable needle assembly 100f of FIGS. 62-69, includes a needle retraction member 116 having a hub portion 112 and a button portion 118 attached to the hub portion 112 via a spring element 198. In one configuration, the button portion 118 includes a base region 200.

Figure 62:
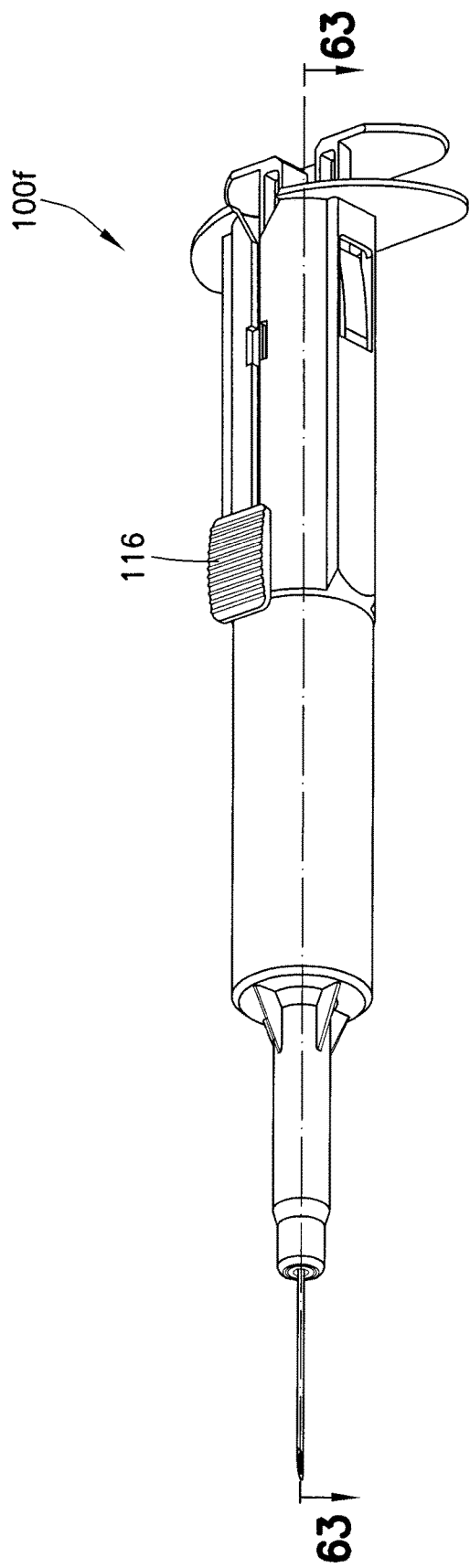
FIG. 62 is a perspective view of a syringe assembly in an initial position in accordance with an embodiment of the present invention.
Figure 63:
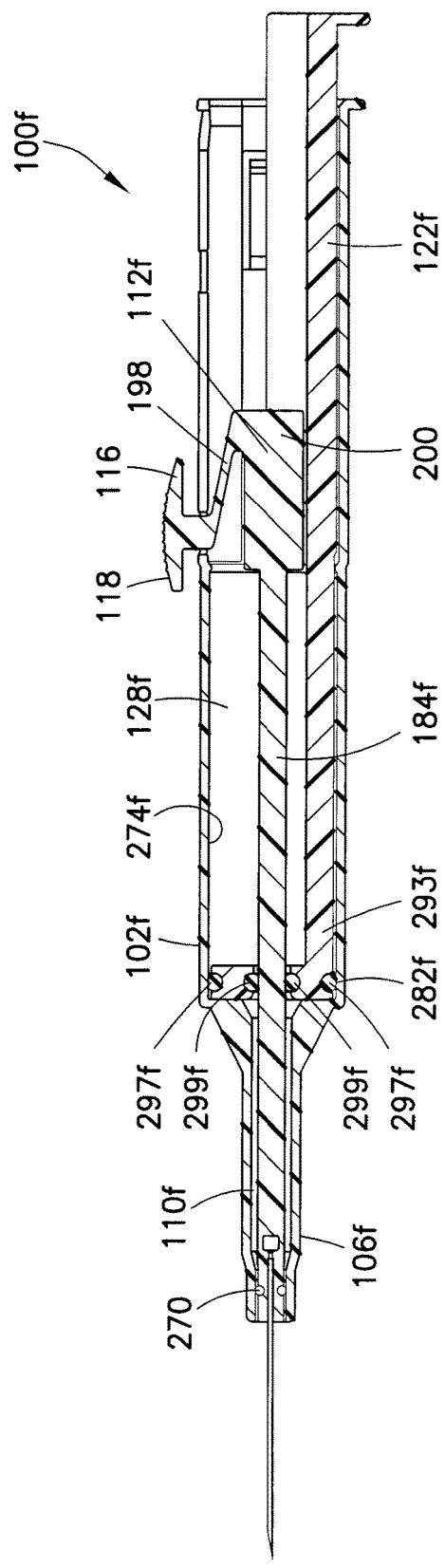
FIG. 63 is a cross-sectional view of the syringe assembly of FIG. 62 taken along line 63-63 in accordance with an embodiment of the present invention.
Figure 64:
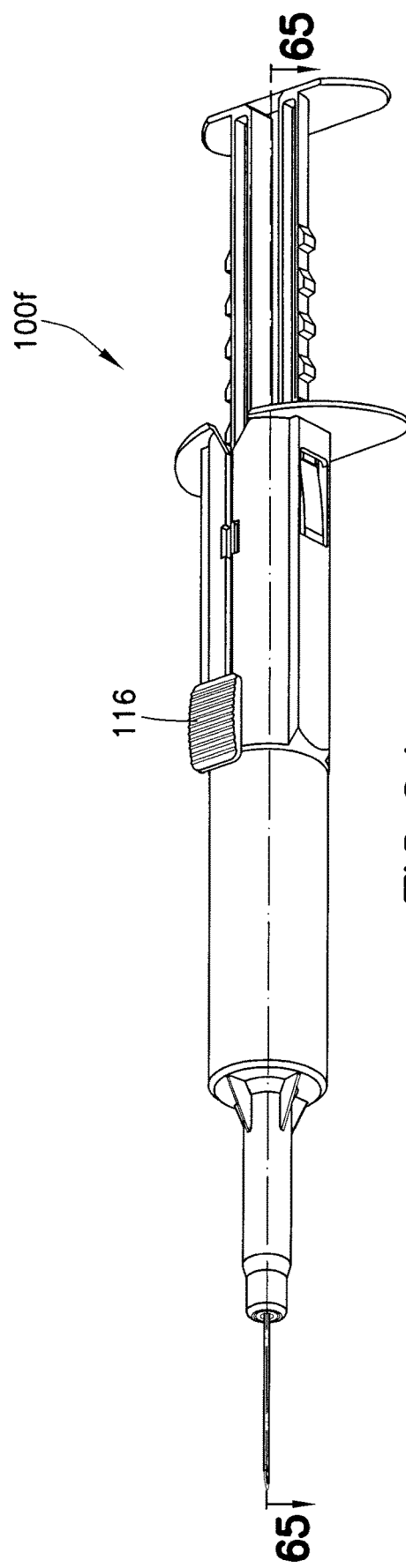
FIG. 64 is a perspective view of the syringe assembly of FIG. 62 having the plunger withdrawn from the syringe body in accordance with an embodiment of the present invention.
Figure 65:
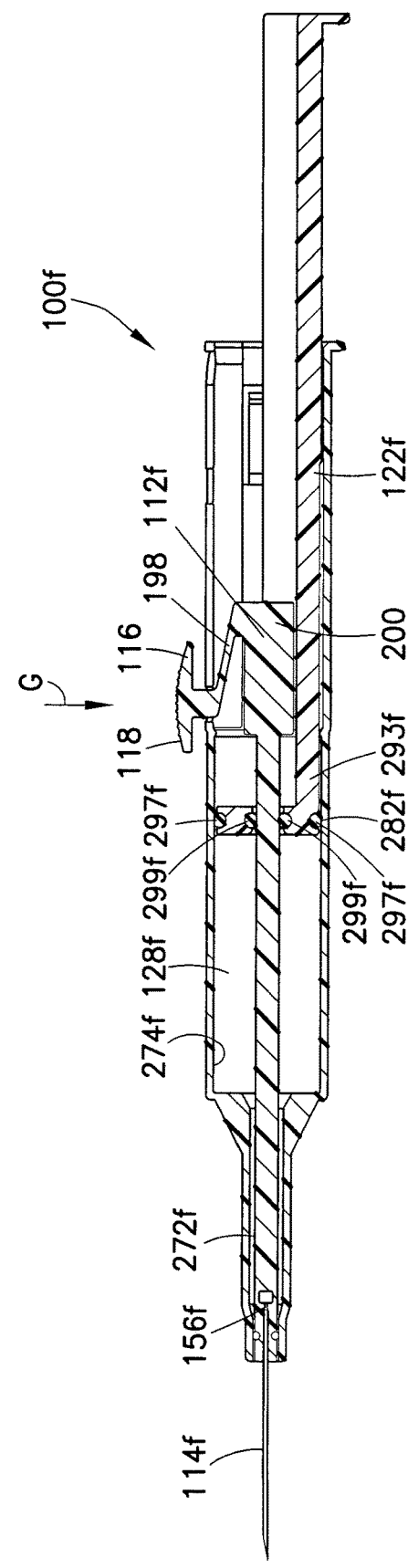
FIG. 65 is a cross-sectional view of the syringe assembly of FIG. 64 taken along line 65-65 in accordance with an embodiment of the present invention.
Figure 68:
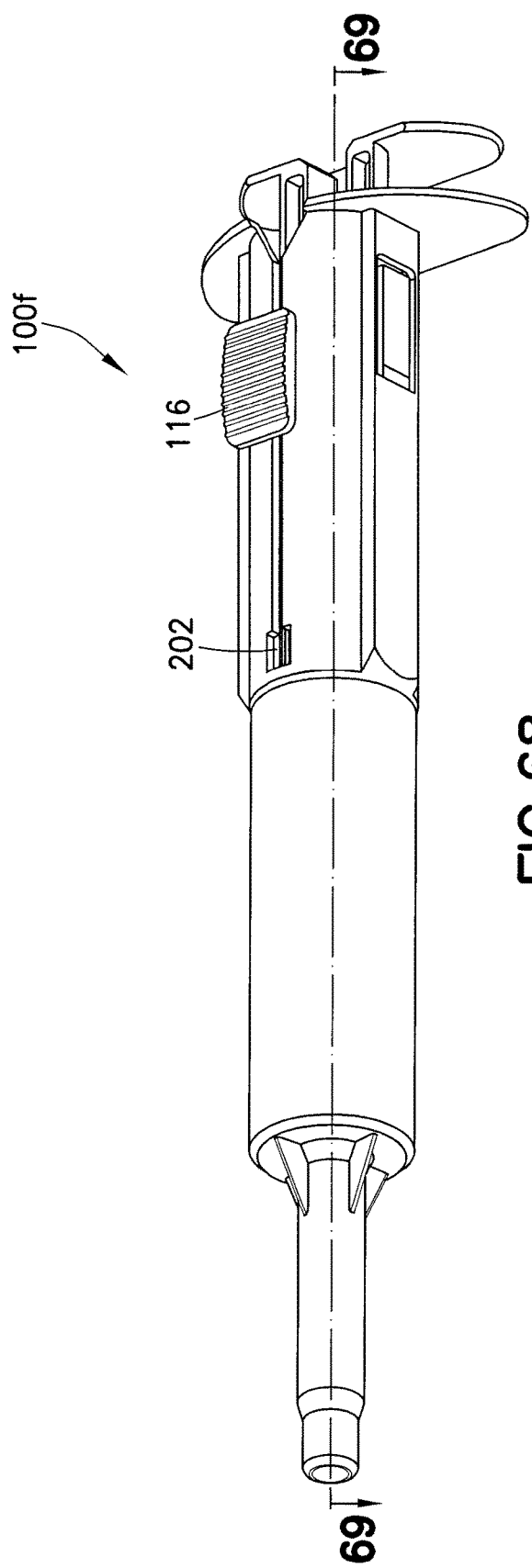
FIG. 68 is a perspective view of the syringe assembly of FIG. 62 having the plunger redeployed within the syringe body in accordance with an embodiment of the present invention.
Figure 69:
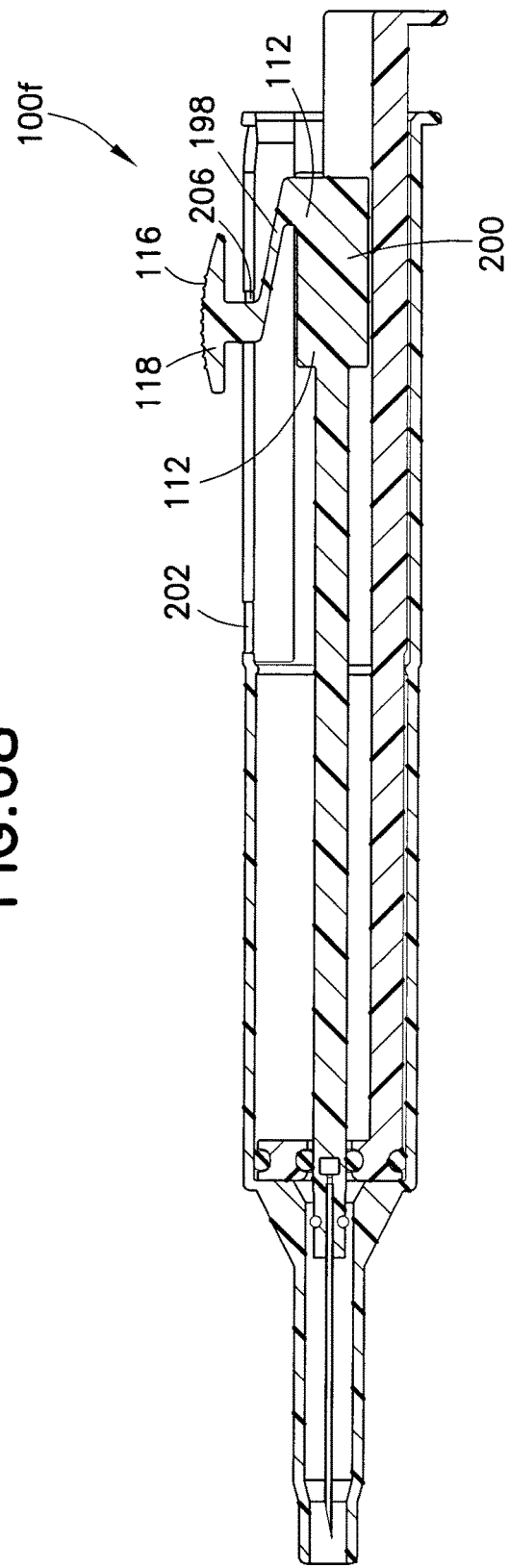
FIG. 69 is a cross-sectional view of the syringe assembly of FIG. 68 taken along line 69-69 in accordance with an embodiment of the present invention.

In use, a user transitions the retractable needle assembly 100f from the initial position, as shown in FIGS. 62-63, to the specimen draw position, as shown in FIGS. 64-65, and subsequently to the retracted position, as shown in FIGS. 66-67, prior to expelling the contents of the needle assembly 100f to a secondary collection container. During the transition to the retracted position, a user presses the button portion 118 in a downward direction as shown by arrow G of FIG. 65, disengaging the needle retraction member 116 from a first recess 202 within the longitudinal groove 136, as shown in FIG. 66. The user then slides the needle retraction member 116 in a proximal direction as shown by arrow H of FIG. 67 until the hub portion 112 contacts a stop 204 of the proximal end of the housing 102, and the button portion 118 engages a second recess 206 within the longitudinal groove 136. The second recess 206 restrains the needle retraction member 116 in the retracted position during transition of the retractable needle assembly 100f to the specimen transfer position, as shown in FIGS. 68-69 and described above.

Referring specifically to FIG. 63, it is shown that the hollow bore 110f may include a seal 270 adjacent the distal end 106f of the housing 102f. In certain configurations, the seal 270 may be an elastomeric O-ring seal. As shown in FIG. 63, the seal 270 seals the distal end of the hollow bore 110f from atmosphere in the initial position prior to specimen draw. As shown in FIG. 65, as the plunger 122f is withdrawn from the housing 102f in the proximal direction, fluid from the patient enters the cannula 114f and passes through break 156f into a distal flash chamber portion 272f of the reservoir 128f to provide the user with an immediate visual indication that proper access of the patient's blood vessel has been accomplished. Referring to FIG. 67, as the cannula 114f is withdrawn into the interior of the housing 102f in the retracted position, contact between the seal 270 and an interior wall 274f of the housing 102f is disrupted, leaving the reservoir 128f open to atmosphere.

Referring again to FIGS. 63, 65, and 67, in certain configurations, a secondary seal 282f may be provided between the interior wall 274f of the reservoir 128f and the plunger 122f to provide a fluid seal therearound. In another configuration, the secondary seal 282f may be connected to a distal end 293f of the plunger 122f such that the secondary seal 282f is advanced and retracted within the reservoir 128f with the movement of the plunger 122f. In still a further configuration, the secondary seal forms a sealing arrangement around a chamber extender 184f to provide a seal therearound during advancement and retraction of the plunger 122f within the reservoir 128f. In still a further configuration, the secondary seal 282f may include a first sealing member 297f disposed between the interior wall 274f of the reservoir 128f and the plunger 122f, and a second sealing member 299f between the plunger 122f and the hub 112f and/or the chamber extender 184f.

Referring again to FIG. 67, in certain configurations, the interior wall 274f of the reservoir 128f includes a restraining protrusion 301f extending from the interior wall 274f into the interior of the reservoir 128f for restraining a proximal end 303f of the stopper 130f thereagainst in a maximum draw position. Accordingly, the plunger 122f is restrained from advancing beyond the restraining protrusion 301f during the specimen draw phase. In certain configurations, the restraining protrusion 301*f* is positioned at a precise location along the interior wall 274*f* of the reservoir 128*f* to correspond to a specific volume of collected specimen fluid that may be collected within the reservoir 128*f* as the plunger is advanced in the proximal direction.

In accordance with a further embodiment of the present invention, the retractable needle assembly 100*g*, as shown in FIGS. 70-77, is similarly structured to the retractable needle assembly 100*f* described above, with the exception of the rear abutment of the needle retraction member 116 against a proximal end 212 of the housing 102. In use, a user transitions the retractable needle assembly 100*g* from the initial position, as shown in FIGS. 70-71, to the specimen draw position, as shown in FIGS. 72-73, and subsequently to the retracted position, as shown in FIGS. 74-75. During transition to the specimen transfer position, the needle retraction member 116 engages the detent snap 192 such that a rear surface 214 of the hub 112 contacts and rests against the perimeter surface of the proximal end 212 of the housing 102.

Figure 78:
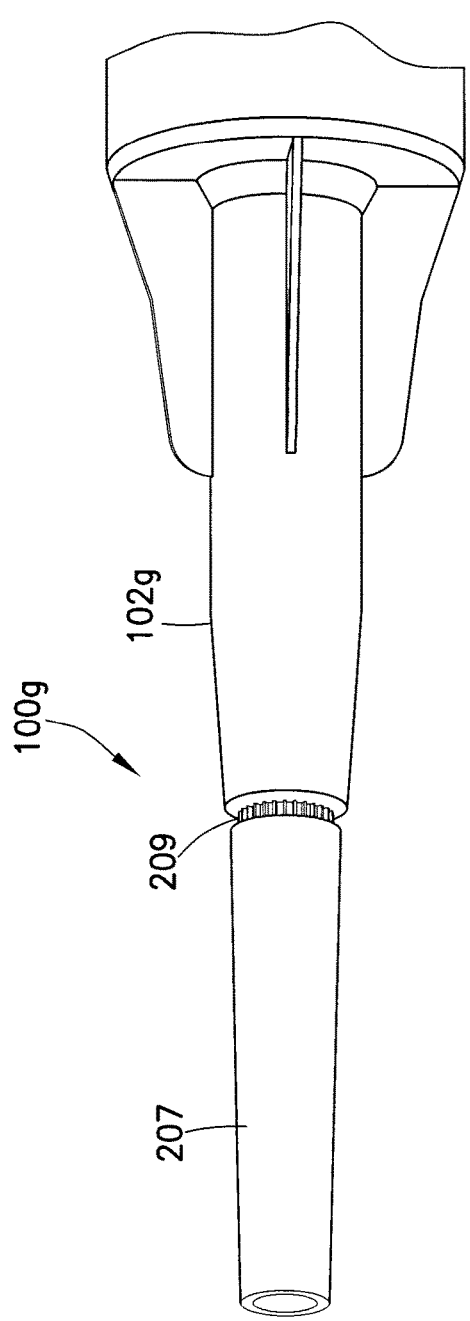
FIG. 78 is a partial perspective view of a syringe assembly having a removable IV shield disposed therewith in accordance with an embodiment of the present invention.

It is noted herein that the retractable needle assembly 100*g* may also include an IV shield 207 removably connected to the distal end of the housing 102*g*, as shown in FIG. 78, at connection 209. As shown in FIG. 78, the IV shield may be provided to initially shield the cannula and may be removed by applying rotational force to the IV shield to sever the connection 209 with the housing 102*g*.

Figure 34:
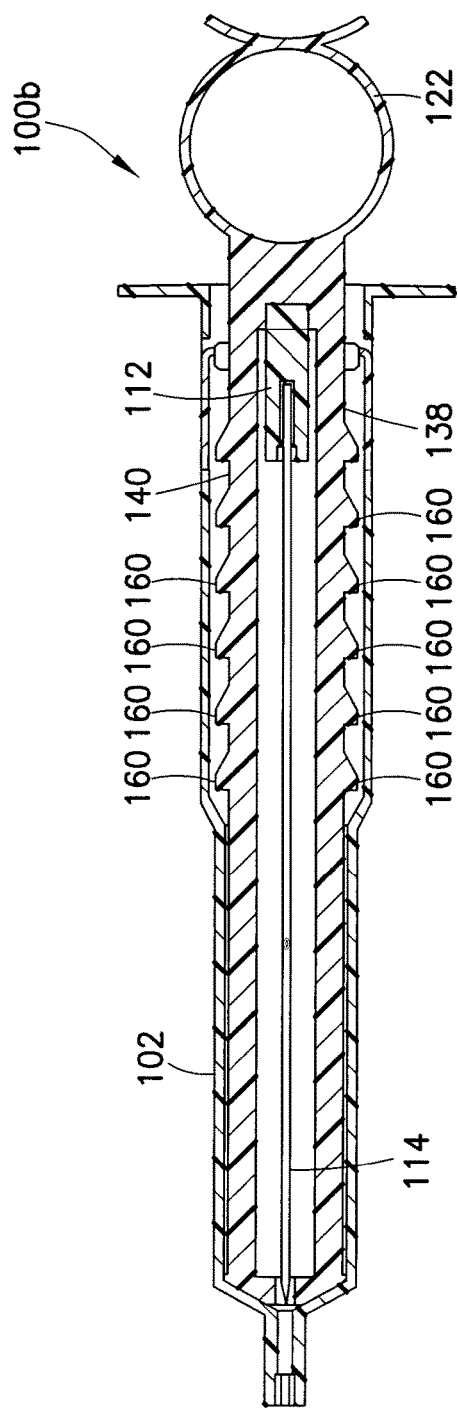
FIG. 34 is a cross-sectional view of the syringe assembly of FIG. 31 taken along line 34-34 of FIG. 32 in accordance with an embodiment of the present invention.
Figure 35:
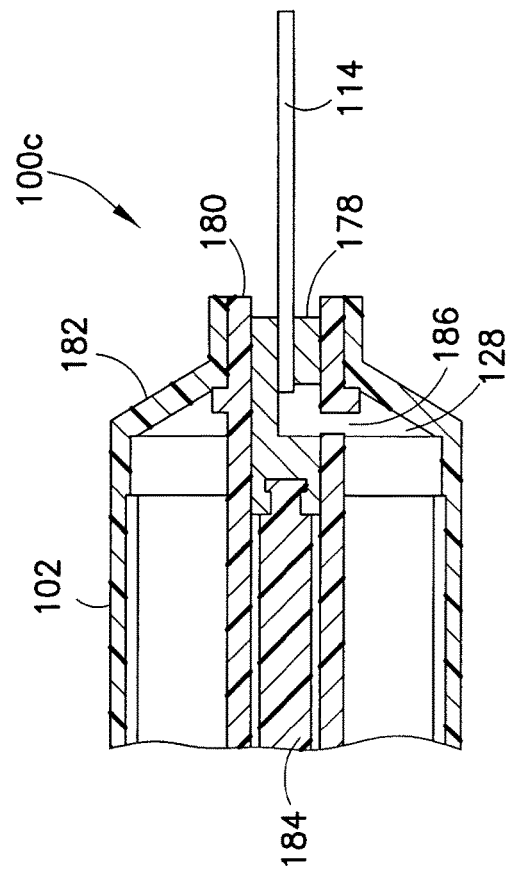
FIG. 35 is a partial cross-sectional top view of the distal end of a syringe assembly having a distal seal in accordance with an embodiment of the present invention.
Figure 40:
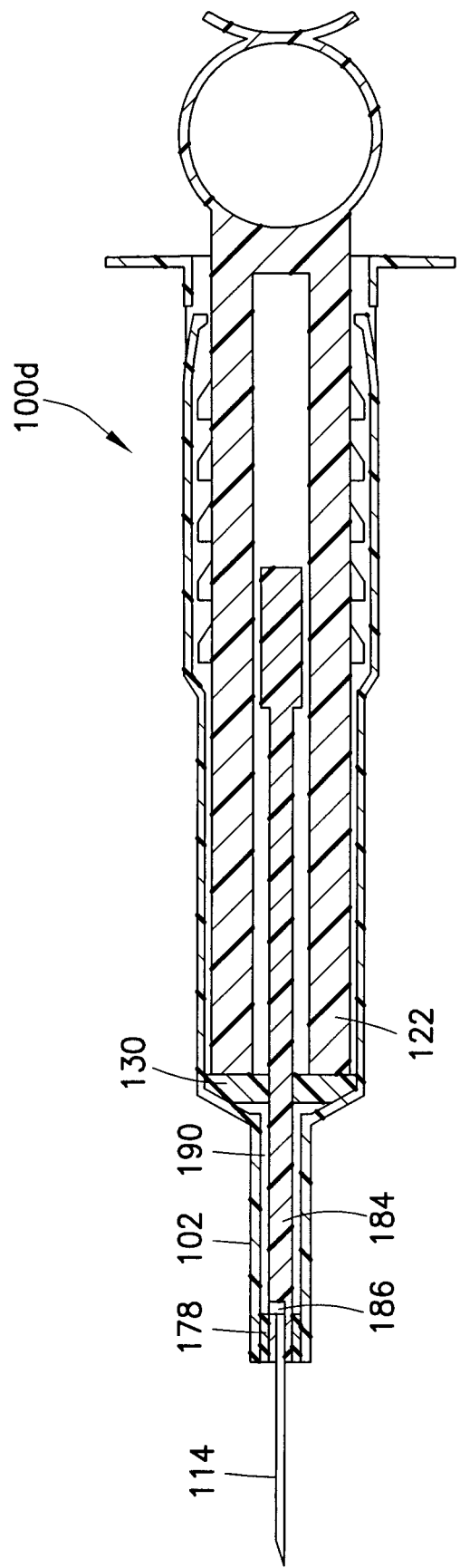
FIG. 40 is a cross-sectional top view of a syringe assembly having a short needle and an extension chamber in the initial position in accordance with an embodiment of the present invention.
Figure 79:
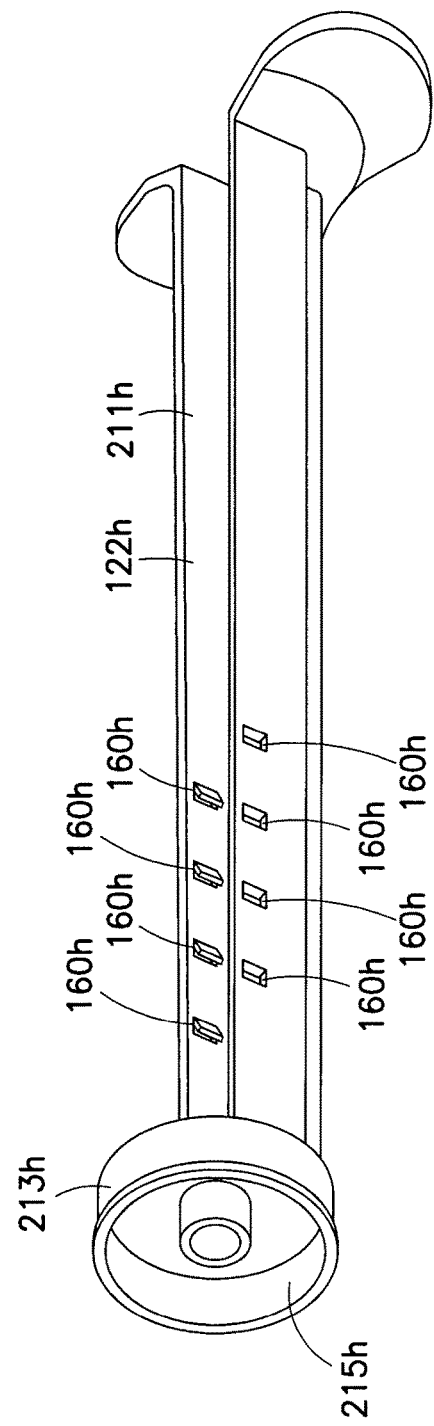
FIG. 79 is a perspective view of a plunger rod in accordance with an embodiment of the present invention.

In a further modified design, as shown in FIG. 79, the plunger 122*h* may include the plurality of ramped stops 160*h*, described in detail with reference to FIG. 34 above, on an interior surface 211*h* of the plunger 122*h*. Each of the ramped stops 160*h* are adapted to engage a corresponding restraint (not shown) disposed on a portion of the housing (also not shown), as described above. Also shown in FIG. 79, the distal end 213*h* of the plunger 122*h* may include a recessed pocket 215*h* for defining an air pocked within the chamber to cushion the fluid sample container therein in an effort to further reduce hemolysis of the fluid sample disposed within the needle assembly. This configuration essentially creates an air pocket proximal to the fluid sample.

Referring to FIGS. 80-82, a chamber extender 184*i* and base region 200*i* form an alternate needle retraction member 116*i* in accordance with an embodiment of the present invention. In this configuration, the distal end 221*i* of the chamber extender 184*i* includes a flashback hole 223*i* for allowing improved visibility of flash phenomenon, as described herein. The base region 200*i* also includes a chamfer 225*i* disposed within a bottom surface 227*i* to further reduce the potential for hemolysis within the needle assembly, as is described herein.

Referring to FIGS. 83-84, an alternate locking mechanism 313*j* is shown. In this configuration, in the initial position, as shown in FIG. 83, the base region 300*i* includes an initial ramp stop 303*i* engaged with an initial lock member 305*i* which restrains the needle assembly 305*i* in an initial position in which the needle cannula is exposed, as described elsewhere herein. Once a specimen collection procedure is complete, a user may transition the device from the initial position, as shown in FIG. 83, to the extended position, as shown in FIG. 84, in which the needle cannula is shielded by the housing, as described elsewhere herein. In order to transition the needle assembly 305*i*, the user must depress the button feature 307*i* of the needle retraction member 309*i* in a downward direction, as shown by arrow V in FIG. 83 in order to disengage the initial ramp stop 303*i* from the initial lock member 305*i*. Once disengaged from the initial lock member 305*i*, the base region 300*i*, and chamber extender 384*i* associated therewith, may be advanced in a proximal direction by applying a force to the button feature 307*i* in the direction of arrow Z, as shown in FIG. 83. In this configuration, the base region 300*i* and the chamber extender 384*i* may be advanced within the housing of the needle assembly, as described herein, to transition the needle assembly to the extended position in which the needle cannula is shielded by the housing. Once a user advances the button feature 307*i*, and structure associated therewith, in the proximal direction a sufficient distance to shield the needle cannula within the housing, the base region 300*i* may be restrained by a second lock member 319*i* disposed proximally to the initial lock member 305*i*. Both the initial lock member 305*i* and the second lock member 319*i* may be disposed along the plunger or a portion of the housing, as described herein. The initial lock member 305*i* and the second lock member 319*i* may include ramped surfaces as described herein permitting one way transmission of the base region 300*i* and the chamber extender 384*i*, as also described herein. The base region 300*i* may include an appropriate recess adapted to contain at least a portion of the initial lock member 305*i* and/or the second lock member 319*i* when a user is not applying a force in the direction of arrow V to the button feature 307*i*. It is intended herein that the embodiment shown in FIGS. 83-84 is similar to the embodiments described above with the addition of the feature that the user must deploy a force in the direction of both arrows V and Z in order to transition the retractable needle assembly from the initial use position to the extended shielded position.

In certain embodiments, the present invention described herein, requires that the cannula be withdrawn into the housing prior to the expulsion of blood from within the needle assembly to a secondary collection container. By requiring that the cannula be fully shielded by the housing prior to transfer of the specimen, the incidence of inadvertent needle stick injuries may be greatly reduced. In addition, the device of the present invention eliminates the issue of specimen transfer through a cannula, which is believed to contribute to hemolysis in conventional syringe assemblies.

While the present invention is described with reference to several distinct embodiments of a retractable needle assembly and method of use, those skilled in the art may make modifications and alterations without departing from the scope and spirit. Accordingly, the above detailed description is intended to be illustrative rather than restrictive.

What is claimed is:

1. A retractable needle assembly for fluid collection, comprising:
   a housing having a proximal end and a distal end and a sidewall extending therebetween and defining a hollow bore extending between the proximal end and the distal end, wherein the housing further comprises at least one groove extending along at least a portion of the sidewall and at least one restraint extending at least partially into the hollow bore;
   an elongate plunger having a proximal end and a distal end, the distal end of the plunger forming a reservoir within the hollow bore, the reservoir for containing a fluid, the plunger adapted for slidable movement within the hollow bore;
   a hub disposed at least partially within the hollow bore and, the hub at least partially supporting a cannula;
   a needle retraction member separate from the plunger and engaged with the hub for manually selectable advancement of the needle retraction member with respect to a portion of the housing; and at least one mechanical barrier positionable within the at least one groove, wherein the needle retraction member extends at least partially through a portion of the sidewall of the housing such that the needle retraction member and the hub are slidable along at least a portion of the housing, wherein the elongate plunger is transitionable from an initial position in which the plunger is at least partially disposed within the hollow bore, to a retracted position in which the plunger is at least partially disposed exterior to the hollow bore with the at least one restraint being configured to retain the elongate plunger in the retracted position, and the needle retraction member is subsequently transitionable from an initial position in which at least a portion of the cannula is disposed outside the housing, to a retracted position in which the cannula is fully surrounded by the housing, wherein, upon transition of the needle retraction member from the initial position to the retracted position, the needle retraction member engages with the at least one restraint to permit re-deployment of the elongate plunger within the hollow bore in a direction of the distal end, and wherein the at least one mechanical barrier is configured to prevent the needle cannula and the hub from advancing to the initial position once the transition from the initial position to the retracted position has occurred.

2. The retractable needle assembly of claim 1, wherein transition of the elongate plunger from the initial position to the retracted position draws fluid into the reservoir, and wherein re-deployment of the elongate plunger from the retracted position expels fluid from the reservoir.

3. The retractable needle assembly of claim 1, wherein the needle retraction member is disposed external with respect to the housing.

4. The retractable needle assembly of claim 1, wherein the needle retraction member and the hub are a unitary component.

5. The retractable needle assembly of claim 4, wherein the needle retraction member and the hub are co-molded as the unitary component.

6. The retractable needle assembly of claim 4, wherein the needle retraction member and the hub are assembled together as the unitary component.

7. The retractable needle assembly of claim 1, wherein, during transition of the plunger from the retracted position to the initial position, and the needle retraction member from the initial position to the retracted position, the needle cannula remains disposed on a longitudinal axis.

8. The retractable needle assembly of claim 1, wherein the at least one mechanical barrier comprises at least one lock out detent.

9. The retractable needle assembly of claim 8, wherein the at least one lock out detent is formed in the at least one groove of the housing.

* * * * *